(12) United States Patent
Thorne

(10) Patent No.: US 8,690,874 B2
(45) Date of Patent: Apr. 8, 2014

(54) COMPOSITION AND PROCESS FOR BONE GROWTH AND REPAIR

(75) Inventor: Kevin J. Thorne, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 20 days.

(21) Appl. No.: 12/849,414

(22) Filed: Aug. 3, 2010

(65) Prior Publication Data

US 2011/0165199 A1 Jul. 7, 2011

Related U.S. Application Data

(63) Continuation of application No. 11/383,309, filed on May 15, 2006, now abandoned, which is a continuation-in-part of application No. 09/746,921, filed on Dec. 22, 2000, now abandoned.

(51) Int. Cl.
| | | |
|---|---|---|
| *A61B 17/56* | (2006.01) | |
| *A61B 17/58* | (2006.01) | |
| *A61F 2/28* | (2006.01) | |
| *A61F 2/00* | (2006.01) | |

(52) U.S. Cl.
USPC .......... 606/53; 606/60; 606/86; 523/114; 523/115; 623/16.11; 424/423; 424/426

(58) Field of Classification Search
USPC ........... 424/423, 426; 623/16.11; 606/53, 60, 606/86; 523/114, 115
See application file for complete search history.

(56) References Cited

U.S. PATENT DOCUMENTS

| | | |
|---|---|---|
| 2,471,598 A | 5/1949 | Wilt et al. |
| 3,368,911 A | 2/1968 | Kuntz et al. |
| 3,393,080 A | 7/1968 | Erdi et al. |
| 3,443,261 A | 5/1969 | Battista et al. |
| 3,471,598 A | 10/1969 | Battista |
| 3,767,437 A | 10/1973 | Cruz, Jr. |

(Continued)

FOREIGN PATENT DOCUMENTS

| | | |
|---|---|---|
| AU | 2007334213 | 8/2012 |
| AU | 2007334213 B2 | 8/2012 |

(Continued)

OTHER PUBLICATIONS

Clarke et al. Investigation Into the Formation and Mechanical Properties of a Bioactive Material Based on Collagen and Calcium Phosphate; Journal of materials Science Materials in Medicine 4, (1993) 107-110.*

(Continued)

*Primary Examiner* — Patricia Leith
(74) *Attorney, Agent, or Firm* — Schwegman Lundberg & Woessner, P.A.

(57) ABSTRACT

A composition for the induction of bone growth is disclosed. The composition includes a substrate, bone growth protein, and sources of calcium and phosphate. The composition is acidic which promotes high activity of the bone growth protein. The calcium and phosphate sources can be provided as an acidic calcium phosphate salt. Also disclosed are methods of the making the composition and methods of using it.

20 Claims, 26 Drawing Sheets

(56) References Cited

U.S. PATENT DOCUMENTS

| | | | |
|---|---|---|---|
| 3,919,723 A | 11/1975 | Heimke et al. |
| 3,949,073 A | 4/1976 | Daniels et al. |
| 3,968,567 A | 7/1976 | Nevins |
| 4,066,083 A | 1/1978 | Ries |
| 4,131,597 A | 12/1978 | Bluethgen et al. |
| 4,146,936 A | 4/1979 | Aoyagi et al. |
| 4,191,747 A | 3/1980 | Scheicher |
| 4,192,021 A | 3/1980 | Deibig et al. |
| 4,202,055 A | 5/1980 | Reiner et al. |
| 4,233,360 A | 11/1980 | Luck et al. |
| 4,237,559 A | 12/1980 | Borom |
| 4,273,705 A | 6/1981 | Kato |
| 4,294,753 A | 10/1981 | Urist |
| 4,356,572 A | 11/1982 | Guillemin et al. |
| 4,389,487 A | 6/1983 | Ries |
| 4,394,370 A | 7/1983 | Jefferies |
| 4,412,947 A | 11/1983 | Cioca |
| 4,429,691 A | 2/1984 | Niwa et al. |
| 4,430,760 A | 2/1984 | Smestad |
| 4,440,680 A | 4/1984 | Cioca |
| 4,440,750 A | 4/1984 | Glowacki et al. |
| 4,451,397 A | 5/1984 | Huc et al. |
| 4,455,256 A | 6/1984 | Urist |
| 4,472,840 A | 9/1984 | Jefferies |
| 4,485,097 A | 11/1984 | Bell |
| 4,497,075 A | 2/1985 | Niwa et al. |
| 4,516,276 A | 5/1985 | Mittelmeier et al. |
| 4,557,764 A | 12/1985 | Chu |
| 4,563,350 A | 1/1986 | Nathan et al. |
| 4,563,489 A | 1/1986 | Urist |
| 4,596,574 A | 6/1986 | Urist |
| 4,600,533 A | 7/1986 | Chu |
| 4,606,910 A | 8/1986 | Sawyer |
| 4,609,551 A | 9/1986 | Caplan et al. |
| 4,619,655 A | 10/1986 | Hanker et al. |
| 4,619,989 A | 10/1986 | Urist |
| 4,620,327 A | 11/1986 | Caplan et al. |
| 4,623,553 A | 11/1986 | Ries et al. |
| 4,629,464 A | 12/1986 | Takata et al. |
| 4,637,931 A | 1/1987 | Schmitz |
| 4,642,120 A | 2/1987 | Nevo et al. |
| 4,656,130 A | 4/1987 | Shoshan |
| 4,668,295 A | 5/1987 | Bajpai |
| 4,689,399 A | 8/1987 | Chu |
| 4,693,986 A | 9/1987 | Vit et al. |
| 4,698,326 A | 10/1987 | Sauk et al. |
| 4,703,108 A | 10/1987 | Silver et al. |
| 4,725,671 A | 2/1988 | Chu et al. |
| 4,743,229 A | 5/1988 | Chu |
| 4,761,471 A | 8/1988 | Urist |
| 4,774,227 A | 9/1988 | Piez et al. |
| 4,774,228 A | 9/1988 | Seyedin et al. |
| 4,774,322 A | 9/1988 | Seyedin et al. |
| 4,776,890 A | 10/1988 | Chu |
| 4,780,450 A | 10/1988 | Sauk et al. |
| 4,789,663 A | 12/1988 | Wallace et al. |
| 4,789,732 A | 12/1988 | Urist |
| 4,795,467 A * | 1/1989 | Piez et al. ............... 424/423 |
| 4,795,804 A | 1/1989 | Urist |
| 4,804,744 A | 2/1989 | Sen |
| 4,810,691 A | 3/1989 | Seyedin et al. |
| 4,839,215 A | 6/1989 | Starling et al. |
| 4,843,063 A | 6/1989 | Seyedin et al. |
| 4,843,112 A | 6/1989 | Gerhart et al. |
| 4,846,838 A | 7/1989 | Takai et al. |
| 4,863,732 A | 9/1989 | Nathan et al. |
| 4,863,856 A | 9/1989 | Dean, Jr. et al. |
| 4,865,602 A | 9/1989 | Smestad et al. |
| 4,888,366 A | 12/1989 | Chu et al. |
| 4,891,359 A | 1/1990 | Saferstein et al. |
| 4,919,670 A | 4/1990 | Dale et al. |
| 4,948,540 A | 8/1990 | Nigam |
| 4,950,483 A | 8/1990 | Ksander et al. |
| 4,970,298 A | 11/1990 | Silver et al. |
| 4,975,526 A | 12/1990 | Kuberasampath et al. |
| 4,975,527 A | 12/1990 | Koezuka et al. |
| 4,992,226 A * | 2/1991 | Piez et al. ............... 264/109 |
| 4,997,446 A | 3/1991 | Thoma |
| 5,001,169 A | 3/1991 | Nathan et al. |
| 5,011,691 A | 4/1991 | Oppermann et al. |
| 5,024,841 A | 6/1991 | Chu et al. |
| 5,028,695 A | 7/1991 | Eckmayer et al. |
| 5,034,059 A | 7/1991 | Constantz |
| 5,035,715 A | 7/1991 | Smestad et al. |
| 5,047,031 A | 9/1991 | Constantz |
| 5,053,212 A | 10/1991 | Constantz et al. |
| 5,061,286 A | 10/1991 | Lyle |
| 5,069,905 A | 12/1991 | Lidor et al. |
| 5,071,434 A | 12/1991 | Tsuzuki et al. |
| 5,071,436 A | 12/1991 | Huc et al. |
| 5,073,373 A | 12/1991 | O'Leary et al. |
| 5,084,051 A | 1/1992 | Tormala et al. |
| 5,085,861 A | 2/1992 | Gerhart et al. |
| 5,090,815 A | 2/1992 | Bohle |
| 5,106,748 A | 4/1992 | Wozney et al. |
| 5,108,436 A | 4/1992 | Chu et al. |
| 5,108,753 A | 4/1992 | Kuberasampath et al. |
| 5,110,604 A | 5/1992 | Chu et al. |
| 5,118,667 A | 6/1992 | Adams et al. |
| 5,123,923 A | 6/1992 | Pommier et al. |
| 5,123,925 A | 6/1992 | Smestad et al. |
| 5,133,755 A | 7/1992 | Brekke et al. |
| 5,137,534 A | 8/1992 | Sumita |
| 5,152,836 A | 10/1992 | Hirano et al. |
| 5,154,931 A | 10/1992 | Kruger et al. |
| 5,158,934 A | 10/1992 | Ammann et al. |
| 5,162,114 A | 11/1992 | Kuberasampath et al. |
| 5,169,837 A | 12/1992 | Lagarde et al. |
| 5,171,574 A | 12/1992 | Kuberasampath et al. |
| 5,171,579 A | 12/1992 | Ron et al. |
| 5,204,382 A | 4/1993 | Wallace et al. |
| 5,206,023 A | 4/1993 | Hunziker |
| 5,207,710 A | 5/1993 | Chu et al. |
| 5,208,219 A | 5/1993 | Ogawa et al. |
| 5,231,169 A | 7/1993 | Constantz et al. |
| 5,236,456 A | 8/1993 | O'Leary et al. |
| 5,236,704 A | 8/1993 | Fujioka et al. |
| 5,246,457 A | 9/1993 | Piez et al. |
| 5,258,029 A | 11/1993 | Chu et al. |
| 5,262,166 A | 11/1993 | Liu et al. |
| 5,263,985 A | 11/1993 | Bao et al. |
| 5,270,300 A | 12/1993 | Hunziker |
| 5,273,964 A | 12/1993 | Lemons |
| 5,274,078 A | 12/1993 | Wada et al. |
| 5,279,831 A | 1/1994 | Constantz et al. |
| 5,290,494 A | 3/1994 | Coombes et al. |
| 5,290,558 A | 3/1994 | O'Leary et al. |
| 5,290,763 A | 3/1994 | Poser et al. |
| 5,304,577 A | 4/1994 | Nagata et al. |
| 5,306,303 A | 4/1994 | Lynch |
| 5,314,476 A | 5/1994 | Prewett et al. |
| 5,320,844 A | 6/1994 | Liu |
| 5,332,802 A | 7/1994 | Kelman et al. |
| 5,336,264 A | 8/1994 | Constanz et al. |
| 5,338,772 A | 8/1994 | Bauer et al. |
| 5,344,654 A | 9/1994 | Rueger et al. |
| 5,352,715 A | 10/1994 | Wallace et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,498 A | 11/1994 | Brannan et al. |
| 5,366,508 A | 11/1994 | Brekke et al. |
| 5,366,756 A | 11/1994 | Chesterfield et al. |
| 5,368,858 A | 11/1994 | Hunziker |
| 5,371,191 A | 12/1994 | Poser et al. |
| 5,376,375 A | 12/1994 | Rhee et al. |
| 5,393,739 A | 2/1995 | Bentz et al. |
| 5,397,572 A | 3/1995 | Coombes et al. |
| 5,399,361 A | 3/1995 | Song et al. |
| 5,405,390 A | 4/1995 | O'Leary et al. |
| 5,413,989 A | 5/1995 | Ogawa et al. |
| 5,417,975 A | 5/1995 | Lussi et al. |
| 5,422,340 A | 6/1995 | Ammann et al. |
| 5,425,770 A | 6/1995 | Piez et al. |

(56) References Cited

U.S. PATENT DOCUMENTS

| | | |
|---|---|---|
| 5,426,769 A | 6/1995 | Pawloski |
| 5,428,022 A | 6/1995 | Palefsky et al. |
| 5,433,751 A | 7/1995 | Christel et al. |
| 5,443,531 A | 8/1995 | Ripamonti |
| 5,455,231 A * | 10/1995 | Constantz et al. ........... 514/16.7 |
| 5,466,462 A | 11/1995 | Rosenthal et al. |
| 5,475,052 A | 12/1995 | Rhee et al. |
| 5,484,601 A | 1/1996 | O'Leary et al. |
| 5,492,697 A | 2/1996 | Boyan et al. |
| 5,496,552 A | 3/1996 | Kuberasampath et al. |
| 5,507,813 A | 4/1996 | Dowd et al. |
| 5,508,267 A | 4/1996 | Czernuszka et al. |
| 5,510,396 A | 4/1996 | Prewett et al. |
| 5,522,893 A | 6/1996 | Chow et al. |
| 5,522,894 A | 6/1996 | Draenert et al. |
| 5,531,791 A | 7/1996 | Wolfinbarger, Jr. |
| 5,532,217 A | 7/1996 | Silver et al. |
| 5,543,394 A | 8/1996 | Wozney et al. |
| 5,547,378 A | 8/1996 | Linkow |
| 5,549,671 A | 8/1996 | Waybright et al. |
| 5,552,454 A | 9/1996 | Kretschmann et al. |
| 5,563,124 A | 10/1996 | Damien et al. |
| 5,565,502 A | 10/1996 | Glimcher et al. |
| 5,573,771 A | 11/1996 | Geistlich et al. |
| 5,599,552 A | 2/1997 | Dunn et al. |
| 5,604,204 A | 2/1997 | Ammann et al. |
| 5,618,339 A | 4/1997 | Ito |
| 5,618,549 A | 4/1997 | Patat et al. |
| 5,639,402 A | 6/1997 | Barlow et al. |
| 5,645,591 A | 7/1997 | Kuberasampath et al. |
| 5,650,176 A | 7/1997 | Lee et al. |
| 5,661,007 A | 8/1997 | Wozney et al. |
| 5,670,483 A | 9/1997 | Zhang et al. |
| 5,674,290 A | 10/1997 | Li et al. |
| 5,674,292 A | 10/1997 | Tucker et al. |
| 5,674,521 A | 10/1997 | Gehrke et al. |
| 5,676,146 A | 10/1997 | Scarborough |
| 5,676,699 A | 10/1997 | Gogolewski |
| 5,677,284 A | 10/1997 | Li |
| 5,679,723 A | 10/1997 | Cooper |
| 5,681,873 A | 10/1997 | Norton et al. |
| 5,683,459 A | 11/1997 | Brekke |
| 5,683,461 A | 11/1997 | Lee et al. |
| 5,686,425 A | 11/1997 | Lee |
| 5,691,397 A | 11/1997 | Glimcher et al. |
| RE35,694 E | 12/1997 | Seyedin et al. |
| 5,703,043 A | 12/1997 | Celeste et al. |
| 5,707,442 A | 1/1998 | Fogel et al. |
| 5,707,962 A | 1/1998 | Chen et al. |
| 5,709,934 A | 1/1998 | Bell et al. |
| 5,711,957 A | 1/1998 | Patat et al. |
| 5,728,679 A | 3/1998 | Celeste et al. |
| 5,733,337 A | 3/1998 | Carr, Jr. et al. |
| 5,739,286 A | 4/1998 | Silver et al. |
| 5,741,329 A | 4/1998 | Agrawal et al. |
| 5,750,146 A | 5/1998 | Jones et al. |
| 5,755,792 A | 5/1998 | Brekke |
| 5,756,457 A | 5/1998 | Wang et al. |
| 5,769,895 A | 6/1998 | Ripamonti |
| 5,769,897 A | 6/1998 | Harle |
| 5,776,193 A | 7/1998 | Kwan et al. |
| 5,811,094 A | 9/1998 | Caplan et al. |
| 5,814,604 A | 9/1998 | Oppermann et al. |
| 5,824,084 A | 10/1998 | Muschler |
| 5,824,087 A | 10/1998 | Aspden et al. |
| 5,830,340 A | 11/1998 | Iljitch et al. |
| 5,830,493 A | 11/1998 | Yokota et al. |
| 5,837,752 A | 11/1998 | Shastri et al. |
| 5,840,325 A | 11/1998 | Kuberasampath et al. |
| 5,846,312 A | 12/1998 | Ison et al. |
| 5,854,207 A | 12/1998 | Lee et al. |
| 5,899,939 A | 5/1999 | Boyce et al. |
| 5,904,717 A | 5/1999 | Brekke et al. |
| 5,904,718 A | 5/1999 | Jefferies |
| 5,906,827 A | 5/1999 | Khouri et al. |
| 5,910,315 A | 6/1999 | Stevenson et al. |
| 5,910,492 A | 6/1999 | Hoshino et al. |
| 5,916,553 A | 6/1999 | Schmidt |
| 5,916,870 A | 6/1999 | Lee et al. |
| 5,919,408 A | 7/1999 | Muller et al. |
| 5,922,025 A | 7/1999 | Hubbard |
| 5,928,635 A | 7/1999 | Schmidt |
| 5,932,207 A | 8/1999 | Schmidt |
| 5,935,594 A | 8/1999 | Ringeisen et al. |
| 5,948,426 A | 9/1999 | Jefferies |
| 5,948,428 A | 9/1999 | Lee et al. |
| 5,948,429 A | 9/1999 | Bell et al. |
| 5,952,010 A | 9/1999 | Constantz |
| 5,955,438 A | 9/1999 | Pitaru et al. |
| 5,955,529 A | 9/1999 | Imai et al. |
| 5,958,430 A | 9/1999 | Campbell et al. |
| 5,958,441 A | 9/1999 | Oppermann et al. |
| 5,964,805 A | 10/1999 | Stone |
| 5,972,368 A | 10/1999 | McKay |
| 5,990,381 A | 11/1999 | Nishihara |
| 5,997,895 A | 12/1999 | Narotam et al. |
| 6,005,161 A | 12/1999 | Brekke et al. |
| 6,013,853 A | 1/2000 | Athanasiou et al. |
| 6,013,856 A | 1/2000 | Tucker et al. |
| 6,018,095 A | 1/2000 | Lerch et al. |
| 6,027,742 A | 2/2000 | Lee et al. |
| 6,027,743 A | 2/2000 | Khouri et al. |
| 6,028,242 A | 2/2000 | Tucker et al. |
| 6,033,438 A | 3/2000 | Bianchi et al. |
| 6,037,519 A | 3/2000 | McKay |
| 6,039,762 A | 3/2000 | McKay |
| 6,048,964 A | 4/2000 | Lee et al. |
| 6,071,982 A | 6/2000 | Wise et al. |
| 6,077,988 A | 6/2000 | Kuberasampath et al. |
| 6,090,996 A | 7/2000 | Li |
| 6,110,482 A | 8/2000 | Khouri et al. |
| 6,118,043 A | 9/2000 | Nies et al. |
| 6,123,731 A | 9/2000 | Boyce et al. |
| 6,123,957 A | 9/2000 | Jernberg |
| 6,132,463 A | 10/2000 | Lee et al. |
| 6,132,468 A | 10/2000 | Mansmann |
| 6,136,029 A | 10/2000 | Johnson et al. |
| 6,136,030 A | 10/2000 | Lin et al. |
| 6,139,578 A | 10/2000 | Lee et al. |
| 6,165,487 A | 12/2000 | Ashkar et al. |
| 6,168,801 B1 | 1/2001 | Heil, Jr. et al. |
| 6,177,406 B1 | 1/2001 | Wang et al. |
| 6,180,605 B1 | 1/2001 | Chen et al. |
| 6,180,606 B1 | 1/2001 | Chen et al. |
| 6,183,515 B1 | 2/2001 | Barlow et al. |
| 6,183,737 B1 | 2/2001 | Zaleske et al. |
| 6,187,046 B1 | 2/2001 | Yamamoto et al. |
| 6,187,047 B1 | 2/2001 | Kwan et al. |
| 6,187,329 B1 | 2/2001 | Agrawal et al. |
| 6,187,742 B1 | 2/2001 | Wozney et al. |
| 6,189,537 B1 | 2/2001 | Wolfinbarger, Jr. |
| 6,201,039 B1 | 3/2001 | Brown et al. |
| 6,203,573 B1 | 3/2001 | Walter et al. |
| 6,203,574 B1 | 3/2001 | Kawamura |
| 6,206,924 B1 | 3/2001 | Timm |
| 6,206,931 B1 | 3/2001 | Cook et al. |
| 6,214,049 B1 | 4/2001 | Gayer et al. |
| 6,214,368 B1 | 4/2001 | Lee et al. |
| 6,221,109 B1 | 4/2001 | Geistlich et al. |
| 6,241,771 B1 | 6/2001 | Gresser et al. |
| 6,261,565 B1 | 7/2001 | Empie et al. |
| 6,261,586 B1 | 7/2001 | McKay |
| 6,264,701 B1 | 7/2001 | Brekke |
| 6,277,151 B1 | 8/2001 | Lee et al. |
| 6,280,191 B1 | 8/2001 | Gordon |
| 6,280,474 B1 | 8/2001 | Cassidy et al. |
| 6,281,195 B1 | 8/2001 | Rueger et al. |
| 6,287,341 B1 | 9/2001 | Lee et al. |
| 6,287,816 B1 | 9/2001 | Rosen et al. |
| 6,294,041 B1 | 9/2001 | Boyce et al. |
| 6,294,187 B1 | 9/2001 | Boyce et al. |
| 6,296,667 B1 | 10/2001 | Johnson et al. |
| 6,297,213 B1 | 10/2001 | Oppermann et al. |
| 6,299,650 B1 | 10/2001 | Van Blitterswijk et al. |

(56) References Cited

U.S. PATENT DOCUMENTS

| | | |
|---|---|---|
| 6,300,315 B1 | 10/2001 | Liu |
| 6,302,913 B1 | 10/2001 | Ripamonti et al. |
| 6,306,169 B1 | 10/2001 | Lee et al. |
| 6,309,422 B1 | 10/2001 | Farrington et al. |
| 6,309,909 B1 | 10/2001 | Ohgiyama |
| 6,311,690 B1 | 11/2001 | Jefferies |
| 6,326,018 B1 | 12/2001 | Gertzman et al. |
| 6,331,312 B1 | 12/2001 | Lee et al. |
| 6,335,007 B1 | 1/2002 | Shimizu et al. |
| 6,340,648 B1 | 1/2002 | Imura et al. |
| 6,346,123 B1 | 2/2002 | McKay |
| 6,352,972 B1 | 3/2002 | Nimni et al. |
| 6,371,985 B1 | 4/2002 | Goldberg |
| 6,372,257 B1 | 4/2002 | Marchosky |
| 6,376,211 B1 | 4/2002 | Little, II et al. |
| 6,379,385 B1 | 4/2002 | Kalas et al. |
| 6,383,519 B1 | 5/2002 | Sapieszko et al. |
| 6,384,196 B1 | 5/2002 | Weis et al. |
| 6,384,197 B1 | 5/2002 | Weis et al. |
| 6,395,036 B1 | 5/2002 | Czernuszka et al. |
| 6,406,498 B1 | 6/2002 | Tormala et al. |
| 6,417,166 B2 | 7/2002 | Liu |
| 6,419,708 B1 | 7/2002 | Hall et al. |
| 6,423,095 B1 | 7/2002 | Van Hoeck et al. |
| 6,425,949 B1 | 7/2002 | Lemaitre et al. |
| 6,426,332 B1 | 7/2002 | Rueger et al. |
| 6,432,919 B1 | 8/2002 | Wang et al. |
| 6,440,444 B2 | 8/2002 | Boyce et al. |
| 6,444,222 B1 | 9/2002 | Asculai et al. |
| 6,454,787 B1 | 9/2002 | Maddalo et al. |
| 6,461,630 B1 | 10/2002 | Tucker et al. |
| 6,468,308 B1 | 10/2002 | Kuberasampath et al. |
| 6,471,993 B1 | 10/2002 | Shastri et al. |
| 6,478,825 B1 | 11/2002 | Winterbottom et al. |
| 6,479,065 B2 | 11/2002 | Jaworowicz et al. |
| 6,479,565 B1 | 11/2002 | Stanley |
| 6,504,079 B2 | 1/2003 | Tucker et al. |
| 6,506,217 B1 | 1/2003 | Arnett |
| 6,511,510 B1 | 1/2003 | de Bruijn et al. |
| 6,511,958 B1 | 1/2003 | Atkinson et al. |
| 6,514,514 B1 | 2/2003 | Atkinson et al. |
| 6,521,246 B2 | 2/2003 | Sapieszko et al. |
| 6,524,345 B1 | 2/2003 | Valimaa et al. |
| 6,540,784 B2 | 4/2003 | Barlow et al. |
| 6,541,023 B1 | 4/2003 | Andre et al. |
| 6,544,290 B1 | 4/2003 | Lee et al. |
| 6,547,866 B1 | 4/2003 | Edwards et al. |
| 6,548,002 B2 | 4/2003 | Gresser et al. |
| 6,551,355 B1 | 4/2003 | Lewandrowski et al. |
| 6,551,995 B1 | 4/2003 | Oppermann et al. |
| 6,576,015 B2 | 6/2003 | Geistlich et al. |
| 6,576,249 B1 | 6/2003 | Gendler et al. |
| 6,582,471 B1 | 6/2003 | Bittmann et al. |
| 6,589,590 B2 | 7/2003 | Czernuszka et al. |
| 6,602,294 B1 | 8/2003 | Sittinger et al. |
| 6,645,250 B2 | 11/2003 | Schulter |
| 6,679,918 B1 | 1/2004 | Benedict et al. |
| 6,696,073 B2 | 2/2004 | Boyce et al. |
| 6,712,822 B2 | 3/2004 | Re et al. |
| 6,736,799 B1 | 5/2004 | Erbe et al. |
| 6,764,517 B2 | 7/2004 | Yamamoto et al. |
| 6,840,961 B2 | 1/2005 | Tofighi et al. |
| 6,846,327 B2 | 1/2005 | Khandkar et al. |
| 6,884,621 B2 | 4/2005 | Liao et al. |
| 6,899,107 B2 | 5/2005 | Lewandrowski et al. |
| 6,902,584 B2 | 6/2005 | Kwan et al. |
| 6,903,146 B2 | 6/2005 | Matsushima et al. |
| 6,911,046 B2 | 6/2005 | Schulter |
| 6,911,212 B2 | 6/2005 | Gertzman et al. |
| 6,921,412 B1 | 7/2005 | Black et al. |
| 6,933,326 B1 | 8/2005 | Griffey et al. |
| 6,953,594 B2 | 10/2005 | Lee et al. |
| 6,974,862 B2 | 12/2005 | Ringeisen et al. |
| 6,991,803 B2 | 1/2006 | Sapieszko et al. |
| 7,026,292 B1 | 4/2006 | Lee et al. |
| 7,045,141 B2 | 5/2006 | Merboth et al. |
| 7,052,517 B2 | 5/2006 | Murphy et al. |
| 7,077,866 B2 | 7/2006 | Gresser et al. |
| 7,105,182 B2 | 9/2006 | Szymaitis |
| 7,122,057 B2 | 10/2006 | Beam et al. |
| 7,132,110 B2 | 11/2006 | Kay et al. |
| 7,153,938 B2 | 12/2006 | Kikuchi et al. |
| 7,156,880 B2 | 1/2007 | Evans et al. |
| 7,163,691 B2 | 1/2007 | Knaack et al. |
| 7,163,965 B2 | 1/2007 | Sotome et al. |
| 7,166,133 B2 | 1/2007 | Evans et al. |
| 7,172,629 B2 | 2/2007 | McKay |
| 7,175,858 B2 | 2/2007 | Constantz et al. |
| 7,189,263 B2 | 3/2007 | Erbe et al. |
| 7,189,392 B1 | 3/2007 | Kim et al. |
| 7,229,545 B2 | 6/2007 | Sewing et al. |
| 7,235,107 B2 | 6/2007 | Evans et al. |
| 7,241,316 B2 | 7/2007 | Evans et al. |
| 7,250,550 B2 | 7/2007 | Overby et al. |
| 7,252,685 B2 | 8/2007 | Bindseil et al. |
| 7,252,841 B2 | 8/2007 | Constantz |
| 7,303,814 B2 | 12/2007 | Lamberti et al. |
| 7,318,840 B2 | 1/2008 | McKay |
| 7,318,841 B2 | 1/2008 | Tofighi et al. |
| 7,358,284 B2 | 4/2008 | Griffey et al. |
| 7,473,678 B2 | 1/2009 | Lynch |
| 7,485,617 B1 | 2/2009 | Pohl et al. |
| 7,494,950 B2 | 2/2009 | Armitage et al. |
| 7,498,040 B2 | 3/2009 | Masinaei et al. |
| 7,498,041 B2 | 3/2009 | Masinaei et al. |
| 7,517,539 B1 | 4/2009 | Lee et al. |
| 7,531,004 B2 | 5/2009 | Bagga et al. |
| 7,534,264 B2 | 5/2009 | Fischer |
| 7,534,451 B2 | 5/2009 | Erbe et al. |
| 7,621,963 B2 | 11/2009 | Simon et al. |
| 7,628,851 B2 | 12/2009 | Armitage et al. |
| 7,670,378 B2 | 3/2010 | Bloemer et al. |
| 7,670,384 B2 | 3/2010 | Kumar et al. |
| 7,686,239 B2 | 3/2010 | Tofighi et al. |
| 7,718,616 B2 | 5/2010 | Thorne |
| 7,722,895 B1 | 5/2010 | McKay et al. |
| 7,771,741 B2 | 8/2010 | Drapeau et al. |
| 7,776,100 B2 | 8/2010 | Brekke et al. |
| 7,780,994 B2 | 8/2010 | Lynn et al. |
| 7,785,617 B2 | 8/2010 | Shakesheff et al. |
| 7,799,767 B2 | 9/2010 | Lamberti et al. |
| 7,811,608 B2 | 10/2010 | Kay et al. |
| 7,824,702 B2 | 11/2010 | Wironen et al. |
| 7,833,278 B2 | 11/2010 | Evans et al. |
| 7,857,860 B2 | 12/2010 | Saini et al. |
| 7,887,598 B2 | 2/2011 | Evans et al. |
| 7,887,831 B2 | 2/2011 | Yayon |
| 7,892,291 B2 | 2/2011 | Evans et al. |
| 7,897,722 B2 | 3/2011 | Chung et al. |
| 7,910,690 B2 | 3/2011 | Ringeisen et al. |
| 7,951,200 B2 | 5/2011 | Heinz |
| 7,959,941 B2 | 6/2011 | Knaack et al. |
| 7,963,997 B2 | 6/2011 | Brekke et al. |
| 8,029,575 B2 | 10/2011 | Borden |
| 8,497,236 B2 | 7/2013 | Benedict et al. |
| 2001/0004225 A1 | 6/2001 | Nicholls et al. |
| 2001/0005797 A1 | 6/2001 | Barlow et al. |
| 2001/0008980 A1 | 7/2001 | Gresser et al. |
| 2001/0010023 A1 | 7/2001 | Schwartz et al. |
| 2001/0012968 A1 | 8/2001 | Preissman |
| 2001/0014662 A1 | 8/2001 | Rueger et al. |
| 2001/0014667 A1 | 8/2001 | Chen et al. |
| 2001/0014830 A1 | 8/2001 | Kwan et al. |
| 2001/0014831 A1 | 8/2001 | Scarborough |
| 2001/0016646 A1 | 8/2001 | Rueger et al. |
| 2001/0016772 A1 | 8/2001 | Lee et al. |
| 2001/0018614 A1 | 8/2001 | Bianchi |
| 2001/0018797 A1 | 9/2001 | Shepherd |
| 2001/0020476 A1 | 9/2001 | Gan et al. |
| 2001/0031799 A1 | 10/2001 | Shimp |
| 2001/0037014 A1 | 11/2001 | Liu |
| 2001/0039453 A1 | 11/2001 | Gresser et al. |
| 2001/0041792 A1 | 11/2001 | Donda et al. |
| 2001/0041942 A1 | 11/2001 | Ylanen et al. |

(56) References Cited

U.S. PATENT DOCUMENTS

| | | |
|---|---|---|
| 2001/0043940 A1 | 11/2001 | Boyce et al. |
| 2001/0044413 A1 | 11/2001 | Pierce et al. |
| 2001/0049141 A1 | 12/2001 | Fike et al. |
| 2001/0051834 A1 | 12/2001 | Frondoza et al. |
| 2001/0053937 A1 | 12/2001 | Johnson et al. |
| 2001/0055622 A1 | 12/2001 | Burrell et al. |
| 2002/0013626 A1 | 1/2002 | Geistlich et al. |
| 2002/0013627 A1 | 1/2002 | Geistlich et al. |
| 2002/0018796 A1 | 2/2002 | Wironen |
| 2002/0018797 A1 | 2/2002 | Cui et al. |
| 2002/0018798 A1 | 2/2002 | Sewing et al. |
| 2002/0022883 A1 | 2/2002 | Burg |
| 2002/0022885 A1 | 2/2002 | Ochi |
| 2002/0034532 A1 | 3/2002 | Brodbeck et al. |
| 2002/0034533 A1 | 3/2002 | Peterson et al. |
| 2002/0037309 A1 | 3/2002 | Jaworowicz et al. |
| 2002/0042657 A1 | 4/2002 | Pugh et al. |
| 2002/0045582 A1 | 4/2002 | Margolin et al. |
| 2002/0053937 A1 | 5/2002 | Lloyd |
| 2002/0054901 A1 | 5/2002 | Gainey et al. |
| 2002/0055143 A1 | 5/2002 | Bell et al. |
| 2002/0058622 A1 | 5/2002 | Igari et al. |
| 2002/0061328 A1 | 5/2002 | Gertzman et al. |
| 2002/0072804 A1 | 6/2002 | Donda |
| 2002/0076429 A1 | 6/2002 | Wironen et al. |
| 2002/0082220 A1 | 6/2002 | Hoemann et al. |
| 2002/0082594 A1 | 6/2002 | Hata et al. |
| 2002/0082694 A1 | 6/2002 | McKay |
| 2002/0082697 A1 | 6/2002 | Damien |
| 2002/0082700 A1 | 6/2002 | Bianchi et al. |
| 2002/0085994 A1 | 7/2002 | Ceres et al. |
| 2002/0090725 A1 | 7/2002 | Simpson et al. |
| 2002/0098222 A1 | 7/2002 | Wironen et al. |
| 2002/0106393 A1 | 8/2002 | Bianchi et al. |
| 2002/0106394 A1 | 8/2002 | Tucker et al. |
| 2002/0114795 A1 | 8/2002 | Thorne et al. |
| 2002/0128722 A1 | 9/2002 | Jefferies |
| 2002/0192263 A1 | 12/2002 | Merboth et al. |
| 2003/0009235 A1 | 1/2003 | Manrique et al. |
| 2003/0036797 A1 | 2/2003 | Malaviya et al. |
| 2003/0143207 A1 | 7/2003 | Livesey et al. |
| 2003/0152606 A1 | 8/2003 | Gerber |
| 2003/0232071 A1 | 12/2003 | Gower et al. |
| 2003/0236573 A1 | 12/2003 | Evans et al. |
| 2004/0002558 A1 | 1/2004 | McKay |
| 2004/0062816 A1 | 4/2004 | Atkinson et al. |
| 2004/0081704 A1 | 4/2004 | Benedict et al. |
| 2004/0131562 A1 | 7/2004 | Gower et al. |
| 2004/0181232 A1 | 9/2004 | Re et al. |
| 2004/0197311 A1 | 10/2004 | Brekke et al. |
| 2004/0220680 A1 | 11/2004 | Yamamoto et al. |
| 2005/0053638 A1 | 3/2005 | Tanaka et al. |
| 2005/0079201 A1 | 4/2005 | Rathenow et al. |
| 2005/0089579 A1 | 4/2005 | Li et al. |
| 2005/0199156 A1 | 9/2005 | Khairoun et al. |
| 2005/0217538 A1 | 10/2005 | Reinstorf et al. |
| 2005/0249773 A1 | 11/2005 | Maspero et al. |
| 2005/0251266 A1 | 11/2005 | Maspero et al. |
| 2005/0261767 A1 | 11/2005 | Anderson et al. |
| 2005/0283255 A1 | 12/2005 | Geremakis et al. |
| 2005/0288795 A1 | 12/2005 | Bagga et al. |
| 2006/0030627 A1 | 2/2006 | Yamamoto et al. |
| 2006/0030948 A1 | 2/2006 | Manrique et al. |
| 2006/0039951 A1 | 2/2006 | Sapieszko et al. |
| 2006/0093670 A1 | 5/2006 | Mizushima et al. |
| 2006/0147547 A1 | 7/2006 | Yayon |
| 2006/0184131 A1 | 8/2006 | Murphy et al. |
| 2006/0204544 A1 | 9/2006 | Sunwoo et al. |
| 2006/0204580 A1 | 9/2006 | Gower et al. |
| 2006/0204581 A1 | 9/2006 | Gower et al. |
| 2006/0216321 A1 | 9/2006 | Lyu et al. |
| 2006/0233851 A1 | 10/2006 | Simon et al. |
| 2006/0246150 A1 | 11/2006 | Thorne |
| 2006/0251729 A1 | 11/2006 | Kay et al. |
| 2006/0270037 A1 | 11/2006 | Kato et al. |
| 2006/0292350 A1 | 12/2006 | Kawamura et al. |
| 2007/0003593 A1 | 1/2007 | Wironen et al. |
| 2007/0071791 A1 | 3/2007 | Fischer |
| 2007/0088437 A1 | 4/2007 | Betz et al. |
| 2007/0093912 A1 | 4/2007 | Borden |
| 2007/0128249 A1 | 6/2007 | McKay |
| 2007/0129807 A1 | 6/2007 | Lynch et al. |
| 2007/0134285 A1 | 6/2007 | Lynn et al. |
| 2007/0154563 A1 | 7/2007 | Behnam et al. |
| 2007/0178158 A1 | 8/2007 | Knaack et al. |
| 2007/0191963 A1 | 8/2007 | Winterbottom et al. |
| 2007/0202148 A1 | 8/2007 | Ringeisen et al. |
| 2007/0231788 A1 | 10/2007 | Behnam et al. |
| 2007/0233272 A1 | 10/2007 | Boyce et al. |
| 2007/0248575 A1 | 10/2007 | Connor et al. |
| 2007/0276489 A1 | 11/2007 | Bindseil et al. |
| 2008/0015692 A1 | 1/2008 | Heinz |
| 2008/0015709 A1 | 1/2008 | Evans et al. |
| 2008/0033548 A1 | 2/2008 | Xuenong et al. |
| 2008/0033572 A1 | 2/2008 | D'antonio et al. |
| 2008/0063671 A1 | 3/2008 | Morris et al. |
| 2008/0065210 A1 | 3/2008 | McKay |
| 2008/0069852 A1 | 3/2008 | Shimp et al. |
| 2008/0095815 A1 | 4/2008 | Mao |
| 2008/0114458 A1 | 5/2008 | McKay |
| 2008/0124397 A1 | 5/2008 | Wironen et al. |
| 2008/0145392 A1 | 6/2008 | Knaack et al. |
| 2008/0145404 A1 | 6/2008 | Hill et al. |
| 2008/0147065 A1 | 6/2008 | McKay et al. |
| 2008/0147197 A1 | 6/2008 | McKay |
| 2008/0152687 A1 | 6/2008 | Thorne |
| 2008/0188945 A1 | 8/2008 | Boyce et al. |
| 2008/0188946 A1 | 8/2008 | Rosenberg et al. |
| 2008/0199508 A1 | 8/2008 | Lamberti et al. |
| 2008/0233203 A1 | 9/2008 | Woodell-May et al. |
| 2008/0241211 A1 | 10/2008 | Han |
| 2008/0249637 A1 | 10/2008 | Asgari et al. |
| 2008/0262613 A1 | 10/2008 | Gogolewski |
| 2008/0293617 A1 | 11/2008 | Benedict et al. |
| 2008/0317817 A1 | 12/2008 | Fischer |
| 2009/0012625 A1 | 1/2009 | Ying et al. |
| 2009/0017093 A1 | 1/2009 | Springer et al. |
| 2009/0123547 A1 | 5/2009 | Hill et al. |
| 2009/0124552 A1 | 5/2009 | Hill et al. |
| 2009/0142385 A1 | 6/2009 | Gross et al. |
| 2009/0148495 A1 | 6/2009 | Hammer et al. |
| 2009/0155366 A1 | 6/2009 | Pohl et al. |
| 2009/0157182 A1 | 6/2009 | Koblish et al. |
| 2009/0246244 A1 | 10/2009 | McKay et al. |
| 2009/0254104 A1 | 10/2009 | Murray |
| 2009/0269388 A1 | 10/2009 | Sunwoo et al. |
| 2009/0292359 A1 | 11/2009 | Borden |
| 2009/0292360 A1 | 11/2009 | Borden |
| 2009/0292367 A1 | 11/2009 | Borden |
| 2009/0324675 A1 | 12/2009 | Gunatillake et al. |
| 2010/0004733 A1 | 1/2010 | Atanasoska et al. |
| 2010/0015230 A1 | 1/2010 | Ron |
| 2010/0021520 A1 | 1/2010 | Baskin et al. |
| 2010/0036503 A1 | 2/2010 | Chen et al. |
| 2010/0048763 A1 | 2/2010 | Armitage et al. |
| 2010/0049322 A1 | 2/2010 | McKay |
| 2010/0049330 A1 | 2/2010 | Horvath |
| 2010/0082072 A1 | 4/2010 | Sybert et al. |
| 2010/0098673 A1 | 4/2010 | D'Antonnio et al. |
| 2010/0131074 A1 | 5/2010 | Shikinami |
| 2010/0168869 A1 | 7/2010 | Long et al. |
| 2010/0196489 A1 | 8/2010 | Thorne |
| 2010/0209408 A1 | 8/2010 | Stephen A. et al. |
| 2010/0209470 A1 | 8/2010 | Mohan et al. |
| 2010/0226961 A1 | 9/2010 | Lamberti et al. |
| 2010/0255115 A1 | 10/2010 | Mohan et al. |
| 2010/0266658 A1 | 10/2010 | McKay et al. |
| 2010/0266660 A1 | 10/2010 | McKay et al. |
| 2010/0268227 A1 | 10/2010 | Tong et al. |
| 2011/0045044 A1 | 2/2011 | Masinaei et al. |
| 2011/0133368 A1 | 6/2011 | Ringeisen et al. |
| 2011/0140137 A1 | 6/2011 | Lai |

(56) References Cited

U.S. PATENT DOCUMENTS

| | | | |
|---|---|---|---|
| 2011/0144767 A1 | 6/2011 | Evans et al. | |
| 2011/0183936 A1 | 7/2011 | Bailleul | |
| 2012/0121660 A1 | 5/2012 | Akella et al. | |

FOREIGN PATENT DOCUMENTS

| | | | |
|---|---|---|---|
| CA | 2133253 A1 | 3/1996 | |
| CA | 2446840 A1 | 4/2002 | |
| CA | 2280966 C | 4/2012 | |
| EP | 0164483 A1 | 12/1985 | |
| EP | 0171176 A2 | 2/1986 | |
| EP | 0197693 A2 | 10/1986 | |
| EP | 0233770 A2 | 8/1987 | |
| EP | 0243178 A2 | 10/1987 | |
| EP | 0271668 A1 | 6/1988 | |
| EP | 289562 A1 | 11/1988 | |
| EP | 309241 A2 | 3/1989 | |
| EP | 321277 A2 | 6/1989 | |
| EP | 0 349 048 A2 | 1/1990 | |
| EP | 0349048 A2 | 1/1990 | |
| EP | 0361896 A2 | 4/1990 | |
| EP | 0243178 B1 | 6/1991 | |
| EP | 0197693 B1 | 10/1991 | |
| EP | 271668 B1 | 12/1991 | |
| EP | 321277 B1 | 3/1992 | |
| EP | 522569 A1 | 1/1993 | |
| EP | 0522569 A1 | 1/1993 | |
| EP | 289562 B1 | 2/1993 | |
| EP | 0270254 B1 | 3/1993 | |
| EP | 0558727 A1 | 9/1993 | |
| EP | 0567391 A1 | 10/1993 | |
| EP | 309241 B1 | 12/1993 | |
| EP | 0309241 B1 | 12/1993 | |
| EP | 573491 A1 | 12/1993 | |
| EP | 0446262 B1 | 3/1994 | |
| EP | 0588727 A1 | 3/1994 | |
| EP | 0605799 A1 | 7/1994 | |
| EP | 0605933 B1 | 7/1994 | |
| EP | 608313 A1 | 8/1994 | |
| EP | 0621044 A2 | 10/1994 | |
| EP | 0668478 B1 | 10/1994 | |
| EP | 0623031 A1 | 11/1994 | |
| EP | 0439689 B1 | 12/1994 | |
| EP | 627899 A1 | 12/1994 | |
| EP | 0674908 A1 | 10/1995 | |
| EP | 0719529 A1 | 7/1996 | |
| EP | 0429438 B1 | 8/1996 | |
| EP | 732947 A1 | 9/1996 | |
| EP | 0747067 A2 | 12/1996 | |
| EP | 0754699 A1 | 1/1997 | |
| EP | 855884 B1 | 4/1997 | |
| EP | 828453 A1 | 3/1998 | |
| EP | 837701 A1 | 4/1998 | |
| EP | 855884 A1 | 8/1998 | |
| EP | 0588727 B1 | 11/1998 | |
| EP | 0901795 A2 | 3/1999 | |
| EP | 0605799 B1 | 4/1999 | |
| EP | 0932373 A1 | 8/1999 | |
| EP | 1795214 A2 | 8/1999 | |
| EP | 608313 B1 | 2/2000 | |
| EP | 0623031 B1 | 2/2000 | |
| EP | 0987031 A1 | 3/2000 | |
| EP | 1019027 A1 | 7/2000 | |
| EP | 1053739 A1 | 11/2000 | |
| EP | 1120439 A1 | 8/2001 | |
| EP | 1127581 A1 | 8/2001 | |
| EP | 627899 B1 | 11/2001 | |
| EP | 1150659 | 11/2001 | |
| EP | 1150725 A1 | 11/2001 | |
| EP | 1150726 A1 | 11/2001 | |
| EP | 1178769 A1 | 2/2002 | |
| EP | 1180986 A2 | 2/2002 | |
| EP | 732947 B1 | 3/2002 | |
| EP | 573491 B1 | 4/2002 | |
| EP | 1224925 A2 | 7/2002 | |
| EP | 1233714 A1 | 8/2002 | |
| EP | 1234587 A1 | 8/2002 | |
| EP | 0719529 B1 | 9/2002 | |
| EP | 837701 B1 | 2/2003 | |
| EP | 0987031 B1 | 4/2003 | |
| EP | 1434608 A2 | 4/2003 | |
| EP | 1150726 B1 | 11/2003 | |
| EP | 1019027 A4 | 5/2004 | |
| EP | 1416977 A2 | 5/2004 | |
| EP | 1419791 A1 | 5/2004 | |
| EP | 0855884 B1 | 6/2004 | |
| EP | 1120439 B1 | 6/2004 | |
| EP | 1425024 A2 | 6/2004 | |
| EP | 1437148 A1 | 7/2004 | |
| EP | 1462126 A1 | 9/2004 | |
| EP | 1476202 A1 | 11/2004 | |
| EP | 1476204 A1 | 11/2004 | |
| EP | 1482872 A1 | 12/2004 | |
| EP | 1500405 A1 | 1/2005 | |
| EP | 1677846 | 5/2005 | |
| EP | 1150725 B1 | 6/2005 | |
| EP | 1545466 A1 | 6/2005 | |
| EP | 1701672 | 7/2005 | |
| EP | 1701729 | 7/2005 | |
| EP | 1 561 480 A2 | 8/2005 | |
| EP | 1561480 A2 | 8/2005 | |
| EP | 1708651 A1 | 8/2005 | |
| EP | 1727489 A2 | 8/2005 | |
| EP | 828453 B1 | 11/2005 | |
| EP | 1234587 B1 | 11/2005 | |
| EP | 1608414 A2 | 12/2005 | |
| EP | 1623681 A1 | 2/2006 | |
| EP | 1638486 A2 | 3/2006 | |
| EP | 1642599 A1 | 4/2006 | |
| EP | 1648347 | 4/2006 | |
| EP | 1178769 B1 | 7/2006 | |
| EP | 1712244 A1 | 10/2006 | |
| EP | 1727489 A2 | 12/2006 | |
| EP | 1753474 A2 | 2/2007 | |
| EP | 1771490 A1 | 4/2007 | |
| EP | 1940313 | 5/2007 | |
| EP | 1976459 | 7/2007 | |
| EP | 1976460 | 7/2007 | |
| EP | 0616814 A1 | 10/2007 | |
| EP | 1839622 A2 | 10/2007 | |
| EP | 1844798 A1 | 10/2007 | |
| EP | 2007196 | 11/2007 | |
| EP | 1925325 A1 | 5/2008 | |
| EP | 1608414 B1 | 7/2008 | |
| EP | 2125055 | 9/2008 | |
| EP | 1476204 B1 | 10/2008 | |
| EP | 2139500 | 10/2008 | |
| EP | 1476202 B1 | 1/2009 | |
| EP | 2049591 A1 | 4/2009 | |
| EP | 2070491 A2 | 6/2009 | |
| EP | 2104518 A2 | 9/2009 | |
| EP | 1464345 B1 | 12/2009 | |
| EP | 2129318 A2 | 12/2009 | |
| EP | 1419791 B1 | 2/2010 | |
| EP | 1416977 B1 | 7/2010 | |
| EP | 2260790 A2 | 12/2010 | |
| EP | 1233714 B1 | 2/2012 | |
| GB | 1224925 | 3/1971 | |
| GB | 1224925 A | 3/1971 | |
| GB | 2164042 A | 3/1986 | |
| GB | 2 377 642 A | 1/2003 | |
| GB | 2377642 A | 1/2003 | |
| JP | 61226055 A | 10/1986 | |
| JP | 63066106 A | 3/1988 | |
| JP | 1076861 A | 3/1989 | |
| JP | 64076861 | 3/1989 | |
| JP | 01121059 A | 5/1989 | |
| JP | 1121059 A | 5/1989 | |
| JP | 1250264 A | 10/1989 | |
| JP | 06100410 | 4/1994 | |
| JP | 6100410 A | 4/1994 | |
| JP | 8505548 A | 6/1996 | |
| JP | 9505305 | 5/1997 | |

(56) References Cited

FOREIGN PATENT DOCUMENTS

| | | |
|---|---|---|
| JP | 11164880 A | 6/1999 |
| JP | 11506727 A | 6/1999 |
| JP | 11313882 A | 11/1999 |
| JP | 11313883 A | 11/1999 |
| JP | 2000262608 A | 9/2000 |
| JP | 2002501786 A | 1/2002 |
| JP | 2004520106 A | 7/2004 |
| JP | 5105216 A | 10/2012 |
| WO | WO-8707495 A1 | 12/1987 |
| WO | WO 89/04646 A1 | 6/1989 |
| WO | WO-8904646 A1 | 6/1989 |
| WO | WO-9000892 A1 | 2/1990 |
| WO | WO-9200109 A1 | 1/1992 |
| WO | WO-9209697 A1 | 6/1992 |
| WO | WO-9305823 A1 | 4/1993 |
| WO | WO-9312736 A1 | 7/1993 |
| WO | WO-9313815 A1 | 7/1993 |
| WO | WO-9316739 A1 | 9/1993 |
| WO | WO-9320857 A1 | 10/1993 |
| WO | WO-9402412 A1 | 2/1994 |
| WO | WO-9415653 A1 | 7/1994 |
| WO | WO-9420064 A1 | 9/1994 |
| WO | WO-9525550 A1 | 9/1995 |
| WO | WO-9610374 A1 | 4/1996 |
| WO | WO-9610428 A1 | 4/1996 |
| WO | WO-9639203 A1 | 12/1996 |
| WO | WO-9640297 A1 | 12/1996 |
| WO | WO-9817330 A1 | 4/1998 |
| WO | WO-9830141 A2 | 7/1998 |
| WO | WO-9835653 A1 | 8/1998 |
| WO | WO-9840113 A1 | 9/1998 |
| WO | WO-9851354 A2 | 11/1998 |
| WO | WO-9858602 A1 | 12/1998 |
| WO | WO-9915211 A1 | 4/1999 |
| WO | WO-9919003 A1 | 4/1999 |
| WO | WO-0004940 A1 | 2/2000 |
| WO | WO-0032251 A1 | 6/2000 |
| WO | WO-0045870 A1 | 8/2000 |
| WO | WO-0045871 A1 | 8/2000 |
| WO | WO-0047114 A1 | 8/2000 |
| WO | WO-0071178 A1 | 11/2000 |
| WO | WO-0074690 A1 | 12/2000 |
| WO | WO-0130409 A1 | 5/2001 |
| WO | WO-0132072 A2 | 5/2001 |
| WO | WO-0141821 A1 | 6/2001 |
| WO | WO-0141822 A1 | 6/2001 |
| WO | WO-0166044 A2 | 9/2001 |
| WO | WO-0174410 A1 | 10/2001 |
| WO | WO-0207961 A1 | 1/2002 |
| WO | WO-0211781 A1 | 2/2002 |
| WO | WO-0221222 A1 | 3/2002 |
| WO | WO-0222045 A1 | 3/2002 |
| WO | WO-0224107 A2 | 3/2002 |
| WO | WO-0234113 A2 | 5/2002 |
| WO | WO-0234116 A2 | 5/2002 |
| WO | WO-0240073 A1 | 5/2002 |
| WO | WO-0240963 A2 | 5/2002 |
| WO | WO-02051449 A2 | 7/2002 |
| WO | WO-02051449 A3 | 7/2002 |
| WO | WO-02070029 A2 | 9/2002 |
| WO | WO 03/071991 A1 | 9/2003 |
| WO | WO-03071991 A1 | 9/2003 |
| WO | WO-03092759 A1 | 11/2003 |
| WO | WO-2004078120 A2 | 9/2004 |
| WO | WO-2004091435 A2 | 10/2004 |
| WO | WO-2004103422 A1 | 12/2004 |
| WO | WO 2005/004755 A1 | 1/2005 |
| WO | WO-2005004755 A1 | 1/2005 |
| WO | WO-2005051447 A1 | 6/2005 |
| WO | WO 2005/074614 A2 | 8/2005 |
| WO | WO-2005074614 A2 | 8/2005 |
| WO | WO-2005081699 A2 | 9/2005 |
| WO | WO-2005099785 A1 | 10/2005 |
| WO | WO-2006031196 A1 | 3/2006 |
| WO | WO-2006092718 A2 | 9/2006 |
| WO | WO-2007053850 A2 | 5/2007 |
| WO | WO-2008019024 A2 | 2/2008 |
| WO | WO 2008/076604 A1 | 6/2008 |
| WO | WO-2008076604 A1 | 6/2008 |
| WO | WO-2009052967 A1 | 4/2009 |
| WO | WO-2010117766 A1 | 10/2010 |
| WO | WO-2010119476 A2 | 10/2010 |
| WO | WO-2010134102 A1 | 11/2010 |
| WO | WO-2012068135 A1 | 5/2012 |

OTHER PUBLICATIONS

Kubler, Norbert, et al., "Bone Morphogenetic Protein-Mediated Interaction of Periosteum and Diaphysis," Clinical Orthopaedics and Related Research Magazine, 1989, pp. 279-294, No. 258.

Noah, Ernst Magnus, et al., "Impact of sterilization on the porous design and cell behavior in collagen sponges prepared for tissue engineering," Biomaterials, 2002, vol. 23, pp. 2855-2861.

Stone, Kevin R., et al., "Porcine and Bovine Cartilage Transplants in Cynomolgus Monkey," Transplantation magazine, Mar. 15, 1997, vol. 63, No. 5, pp. 640-645, Williams & Wilkins, USA Baltimore, MD.

Truumees, Eeric, M.D., et al., "Alternatives to Autologous Bone Harvest in Spine Surgery," The University of Pennsylvania Orthopaedic Journal, 1999, vol. 12, pp. 77-88, USA.

"U.S. Appl. No. 09/023,617, Advisory Action mailed Apr. 23, 2002", 3 pgs.

"U.S. Appl. No. 09/023,617, Final Office Action mailed Nov. 23, 2001", 5 pgs.

"U.S. Appl. No. 09/023,617, Non Final Office Action mailed Apr. 24, 2001", 6 pgs.

"U.S. Appl. No. 09/023,617, Notice of Allowance mailed Sep. 15, 2003", 6 pgs.

"U.S. Appl. No. 09/023,617, Response filed Mar. 20, 2002 to Final Office Action mailed Nov. 23, 2001", 6 pgs.

"U.S. Appl. No. 09/023,617, Response filed Jun. 21, 2000 to Restriction Requirement mailed Jun. 15, 2000", 2 pgs.

"U.S. Appl. No. 09/023,617, Response filed Jul. 26, 1999 to Restriction Requirement mailed Jun. 24, 1999", 2 pgs.

"U.S. Appl. No. 09/023,617, Response filed Aug. 24, 2001 to Non Final Office Action mailed Apr. 24, 2001", 6 pgs.

"U.S. Appl. No. 09/023,617, Restriction Requirement mailed Jun. 15, 2000", 6 pgs.

"U.S. Appl. No. 09/023,617, Restriction Requirement mailed Jun. 24, 1999", 5 pgs.

"U.S. Appl. No. 09/746,921, Advisory Action mailed Nov. 8, 2005", 3 pgs.

"U.S. Appl. No. 09/746,921, Examiner Interview Summary mailed Apr. 1, 2002", 1 pg.

"U.S. Appl. No. 09/746,921, Final Office Action mailed Feb. 9, 2007", 14 pgs.

"U.S. Appl. No. 09/746,921, Final Office Action mailed Feb. 25, 2003", 14 pgs.

"U.S. Appl. No. 09/746,921, Final Office Action mailed Jul. 27, 2005", 10 pgs.

"U.S. Appl. No. 09/746,921, Final Office Action mailed Dec. 2, 2004", 12 pgs.

"U.S. Appl. No. 09/746,921, Non Final Office Action mailed Feb. 27, 2006", 7 pgs.

"U.S. Appl. No. 09/746,921, Non Final Office Action mailed Jul. 16, 2002", 13 pgs.

"U.S. Appl. No. 09/746,921, Non Final Office Action mailed Jul. 31, 2006", 10 pgs.

"U.S. Appl. No. 09/746,921, Non Final Office Action mailed Nov. 18, 2003", 15 pgs.

"U.S. Appl. No. 09/746,921, Response filed Feb. 1, 2002 to Restriction Requirement mailed Nov. 1, 2001", 2 pgs.

"U.S. Appl. No. 09/746,921, Response filed May 9, 2006 to Non Final Office Action mailed Feb. 27, 2006", 6 pgs.

"U.S. Appl. No. 09/746,921, Response filed May 11, 2005 to Final Office Action mailed Dec. 2, 2004", 12 pgs.

"U.S. Appl. No. 09/746,921, Response filed May 18, 2004 to Non Final Office Action mailed Nov. 18, 2003", 15 pgs.

(56) References Cited

OTHER PUBLICATIONS

"U.S. Appl. No. 09/746,921, Response filed Aug. 25, 2003 to Final Office Action mailed Feb. 25, 2003", 11 pgs.
"U.S. Appl. No. 09/746,921, Response filed Sep. 13, 2004 to Restriction Requirement mailed Aug. 13, 2004", 3 pgs.
"U.S. Appl. No. 09/746,921, Response filed Oct. 17, 2005 to Final Office Action mailed Jul. 27, 2005", 9 pgs.
"U.S. Appl. No. 09/746,921, Response filed Nov. 20, 2006 to Non Final Office Action mailed Jul. 31, 2006", 6 pgs.
"U.S. Appl. No. 09/746,921, Response filed Nov. 25, 2002 to Non Final Office Action mailed Jul. 16, 2002", 9 pgs.
"U.S. Appl. No. 09/746,921, Restriction Requirement mailed Aug. 13, 2004", 6 pgs.
"U.S. Appl. No. 09/746,921, Restriction Requirement mailed Nov. 1, 2001", 5 pgs.
"U.S. Appl. No. 10/739,492, Advisory Action mailed Feb. 5, 2008", 3 pgs.
"U.S. Appl. No. 10/739,492, Final Office Action mailed Oct. 5, 2007", 6 pgs.
"U.S. Appl. No. 10/739,492, Non Final Office Action mailed May 28, 2008", 11 pgs.
"U.S. Appl. No. 10/739,492, Non Final Office Action mailed Oct. 12, 2006", 7 pgs.
"U.S. Appl. No. 10/739,492, Response filed Jan. 10, 2007 to Non Final Office Action mailed Oct. 12, 2006", 4 pgs.
"U.S. Appl. No. 10/739,492, Response filed Jul. 11, 2006 to Restriction Requirement mailed Jul. 3, 2006", 2 pgs.
"U.S. Appl. No. 10/739,492, Response filed Dec. 10, 2007 to Final Office Action mailed Oct. 5, 2007", 7 pgs.
"U.S. Appl. No. 10/739,492, Restriction Requirement mailed Jul. 3, 2006", 7 pgs.
"U.S. Appl. No. 11/383,309, Advisory Action mailed Dec. 15, 2008", 3 pgs.
"U.S. Appl. No. 11/383,309, Appeal Brief filed Sep. 11, 2009", 42 pgs.
"U.S. Appl. No. 11/383,309, Appeal Brief filed Nov. 5, 2009", 14 pgs.
"U.S. Appl. No. 11/383,309, Final Office Action mailed Aug. 18, 2008", 10 pgs.
"U.S. Appl. No. 11/383,309, Non Final Office Action mailed Feb. 3, 2010", 21 pgs.
"U.S. Appl. No. 11/383,309, Non Final Office Action mailed Mar. 31, 2008", 11 pgs.
"U.S. Appl. No. 11/383,309, Non Final Office Action mailed Apr. 13, 2009", 16 pgs.
"U.S. Appl. No. 11/383,309, Response filed Jan. 21, 2009 to Advisory Action mailed Dec. 15, 2008", 14 pgs.
"U.S. Appl. No. 11/383,309, Response filed Jan. 22, 2008 to Restriction Requirement mailed Jan. 10, 2008", 3 pgs.
"U.S. Appl. No. 11/383,309, Response filed May 6, 2008 to Non Final Office Action mailed Mar. 31, 2008", 12 pgs.
"U.S. Appl. No. 11/383,309, Response filed Nov. 18, 2008 to Final Office Action mailed Aug. 18, 2008", 13 pgs.
"U.S. Appl. No. 11/383,309, Restriction Requirement mailed Jan. 10, 2008", 13 pgs.
"U.S. Appl. No. 11/614,422, Final Office Action mailed Mar. 24, 2009", 8 pgs.
"U.S. Appl. No. 11/614,422, Non Final Office Action mailed Apr. 16, 2008", 6 pgs.
"U.S. Appl. No. 11/614,422, Non Final Office Action mailed Jun. 29, 2009", 6 pgs.
"U.S. Appl. No. 11/614,422, Non Final Office Action mailed Sep. 11, 2008", 8 pgs.
"U.S. Appl. No. 11/614,422, Notice of Allowance mailed Dec. 30, 2009", 7 pgs.
"U.S. Appl. No. 11/614,422, Response filed Jan. 9, 2009", 9 pgs.
"U.S. Appl. No. 11/614,422, Response filed Feb. 5, 2008 to Restriction Requirement mailed Jan. 23, 2008", 2 pgs.
"U.S. Appl. No. 11/614,422, Response filed May 12, 2008 to Non Final Office Action mailed Apr. 16, 2008", 15 pgs.
"U.S. Appl. No. 11/614,422, Response filed Jun. 18, 2009 to Final Office Action mailed Mar. 24, 2009", 7 pgs.
"U.S. Appl. No. 11/614,422, Response filed Aug. 25, 2009 to Non Final Office Action mailed Jun. 29, 2009", 7 pgs.
"U.S. Appl. No. 11/614,422, Restriction Requirement mailed Jan. 23, 2008", 9 pgs.
"U.S. Appl. No. 12/180,035, Advisory Action mailed Jan. 24, 2012", 4 pgs.
"U.S. Appl. No. 12/180,035, Advisory Action mailed Mar. 12, 2010", 4 pgs.
"U.S. Appl. No. 12/180,035, Examiner Interview Summary mailed Mar. 14, 2012", 3 pgs.
"U.S. Appl. No. 12/180,035, Examiner Interview Summary mailed Sep. 27, 2011", 2 pgs.
"U.S. Appl. No. 12/180,035, Final Office Action mailed Sep. 27, 2011", 8 pgs.
"U.S. Appl. No. 12/180,035, Final Office Action mailed Nov. 16, 2009", 12 pgs.
"U.S. Appl. No. 12/180,035, Non Final Office Action mailed Dec. 27, 2010", 14 pgs.
"U.S. Appl. No. 12/180,035, Non Final Office Action mailed Apr. 16, 2009", 10 pgs.
"U.S. Appl. No. 12/180,035, Non Final Office Action mailed Jun. 10, 2010", 13 pgs.
"U.S. Appl. No. 12/180,035, Preliminary Amendment mailed Jul. 25, 2008", 5 pgs.
"U.S. Appl. No. 12/180,035, Response filed Mar. 20, 2012 to Final Office Action mailed Sep. 27, 2011", 9 pgs.
"U.S. Appl. No. 12/180,035, Response filed Jun. 22, 2011 to Non Final Office Action mailed Dec. 27, 2010", 9 pgs.
"U.S. Appl. No. 12/180,035, Response filed Jul. 16, 2009 to Non Final Office Action mailed Apr. 16, 2009", 9 pgs.
"U.S. Appl. No. 12/180,035, Response filed Dec. 22, 2011 to Final Office Action mailed Sep. 27, 2011", 8 pgs.
"U.S. Appl. No. 12/180,035, Response received Feb. 16, 2010 to Final Office Action mailed Nov. 16, 2009", 13 pgs.
"U.S. Appl. No. 12/180,035, Response received Oct. 11, 2010 to Non Final Office Action mailed Jun. 10, 2010", 7 pgs.
"U.S. Appl. No. 12/180,035, Second Preliminary Amendment filed Nov. 24, 2008", 3 pgs.
"U.S. Appl. No. 12/748,999, Response filed Mar. 1, 2012 to Final Office Action mailed Nov. 1, 2011", 6 pgs.
"U.S. Appl. No. 12/748,999, Final Office Action mailed Nov. 1, 2011", 7 pgs.
"U.S. Appl. No. 12/748,999, Non-Final Office Action mailed Feb. 28, 2011", 9 pgs.
"U.S. Appl. No. 12/748,999, Preliminary Amendment filed Mar. 29, 2010", 3 pgs.
"U.S. Appl. No. 12/748,999, Response filed Feb. 14, 2011 to Restriction Requirement mailed Jan. 14, 2011", 6 pgs.
"U.S. Appl. No. 12/748,999, Response filed Aug. 29, 2011 to Non Final Office Action mailed Feb. 28, 2011", 8 pgs.
"U.S. Appl. No. 12/748,999, Restriction Requirement mailed Jan. 14, 2011", 8 pgs.
"Australian Application Serial No. 2007334213, Office Action mailed Jan. 9, 2012", 2 pgs.
"Canadian Application Serial No. 2,280,966, Office Action Oct. 3, 2007", 2 pgs.
"Canadian Application Serial No. 2,280,966, Office Action mailed Apr. 27, 2011", 2 Pgs.
"Canadian Application Serial No. 2,280,966, Office Action mailed Jul. 30, 2006", 2 pgs.
"Canadian Application Serial No. 2,280,966, Office Action mailed Nov. 9, 2009", 3 pgs.
"Canadian Application Serial No. 2,280,966, Office Action Response filed Nov. 9, 2011", 4 pgs.
"Canadian Application Serial No. 2,280,966, Response filed Jan. 29, 2007 to Office Action mailed Jul. 31, 2006", 7 pgs.
"Canadian Application Serial No. 2,280,966, Response filed Mar. 28, 2008 to Office Action mailed Oct. 3, 2007", 12 pgs.
"Canadian Application Serial No. 2,280,966, Response filed May 5, 2010 to Office Action mailed Nov. 9, 2009", 5 pgs.

(56) References Cited

OTHER PUBLICATIONS

"Canadian Application Serial No. 2,446,840, Office Action mailed Jul. 27, 2011", 3 pgs.
"European Application Serial No. 01991379.7, Office Action mailed Jun. 17, 2005", 5 pgs.
"European Application Serial No. 07013717.9, European Search Report mailed Sep. 4, 2007", 8 pgs.
"European Application Serial No. 07013717.9, European Search Report mailed Sep. 10, 2007", 5 pgs.
"European Application Serial No. 07013717.9, Office Action mailed Apr. 1, 2008", 2 pgs.
"European Application Serial No. 07864863.1, Office Action mailed Feb. 22, 2011", 5 pgs.
"European Application Serial No. 07864863.1, Office Action mailed Nov. 6, 2009", 5 pgs.
"European Application Serial No. 07864863.1, Response filed Mar. 16, 2010 to Office Action mailed Nov. 6, 2009", 10 pgs.
"European Application Serial No. 07864863.1, Response filed Nov. 4, 2011 to Office Action mailed Feb. 22, 2011", 7 pgs.
"European Application Serial No. 98908535.2, Office Action mailed Feb. 1, 2006", 4 pgs.
"European Application Serial No. 98908535.2, Office Action mailed Feb. 2, 2005", 4 pgs.
"European Application Serial No. 98908535.2, Office Action mailed Nov. 6, 2006", 3 pgs.
"European Application Serial No. 98908535.2, Response filed May 29, 2006 to Office Action mailed Feb. 1, 2006", 9 pgs.
"European Application Serial No. 98908535.2, Response filed Aug. 2, 2005 to Office Action mailed Feb. 2, 2005", 8 pgs.
"European Application Serial No. 98908535.2, Search Report mailed Mar. 25, 2004", 3 pgs.
"International Application Serial No. PCT/US01/49314, International Search Report mailed Apr. 7, 2002", 5 pgs.
"International Application Serial No. PCT/US01/49314, International Search Report mailed Apr. 7, 2002", 4 pgs.
"International Application Serial No. PCT/US2001/049314, International Preliminary Examination Report mailed Oct. 24, 2002", 2 pgs.
"International Application Serial No. PCT/US2007/085853, International Preliminary Report on Patentability mailed Jun. 23, 2009", 8 pgs.
"International Application Serial No. PCT/US2007/085853, International Search Report mailed Mar. 7, 2008", 5 pgs.
"International Application Serial No. PCT/US2007/085853, International Search Report mailed Jul. 3, 2008", 4 pgs.
"International Application Serial No. PCT/US2011/060823, International Search Report Jan. 24, 2012", 3 pgs.
"International Application Serial No. PCT/US2011/060823, Written Opinion Jan. 24, 2012", 4 pgs.
"Japanese Application Serial No. 1998535914, Office Action mailed Sep. 30, 2008", 3 pgs.
"Japanese Application Serial No. 1998535914, Response filed Aug. 10, 2009", w/Translation, 40 pgs.
"Japanese Application Serial No. 2002-552590, Office Action mailed Mar. 31, 2009", 4 pgs.
"Japanese Application Serial No. 2002-552590, Office Action mailed Aug. 19, 2008", 6 pgs.
"Japanese Application Serial No. 2002-552590, Office Action mailed Dec. 20, 2011", 2 pgs.
"Japanese Application Serial No. 2002-552590, Office Action Received May 6, 2011", 10 pgs.
Bentz, Hanne, et al., "Purification and Characterization of a Unique Osteoinductive Factor from Bovine Bone", The Journal of Biological Chemistry, vol. 264, No. 32, (Dec. 1989), 20805-20810.
Bentz, Hanne, et al., "Transforming Growth Factor-β2 Enhances the Osteo-inductive Activity of a Bovine Bone-Derived Fraction Containing Bone Morphogenetic Protein-2 and 3", Matrix, vol. 11, (1991), 269-279.
Borsato, K., et al., "Measurement of Partition of Stress Between Mineral and Collagen Phases in Bone Using X-ray Diffraction Techniques", J. Biomechanics, vol. 30, No. 9, (1997), 955-957.

Brown, W. E., et al., "Chemical Properties of Bone Mineral", Ann. Res. Mater. Sci., 6, (1976), 213-236.
Brown, W. E., et al., "Crystal Chemistry of Octacalcium Phosphate", Prog. Crystal Growth Charact., 4, (1981), 59-87.
Clarke, K. I., et al., "Investigation into the Formation and Mechanical Properties of a Bioactive Material Based on Collagen and Calcium Phosphate", Journal of Materials Science in Medicine, 4, (1993), 107-110.
Cornell, Charles N, "Initial Clinical Experience with Use of Collagraft as a Bone Graft Substitute", Techniques in Orthopaedics, vol. 7, No. 2, (1992), 55-63.
Cornell, Charles N, et al., "Multicenter Trial of Collagraft as Bone Graft Substitute", Journal of Orthopaedic Trauma, vol. 5, No. 1, (1991), 1-8.
Delustro, Frank, et al., "Immune Responses to Allogeneic and Xenogeneic Implants of Collagen and Collagen Derivatives", Clinical Orthopaedics and Related Research 260, (Nov. 1990), 263-279.
Derutier, et al., "Biphosphonates: Calcium Antiresorptive Agents", Endocrine Module, Spring, [Online]. Retrieved from the Internet: <URL: http://www.auburn.edu/~deruija/endo_bisphos.pdf>, (2002), 1-7.
Francis, Marion D., et al., "Hydroxyapatite Formation from a Hydrated Calcium Monohydrogen Phosphate Precursor", Calcif. Tissue Res., 6, (1971), 335-342.
Johnsson, Mats, et al., "The Role of Brushite and Octacalcium Phosphate in Apatite Formation", Critical Reviews in Oral Biology and Medicine, vol. 3, (1993), 61-82.
Kubler, N., et al., "Bone Morphogenetic Protein-Mediated Interaction of Periosteum and Diaphysis", Clincal Orthopedics and Related Research, vol. 258, (1990), 279-294.
Muschler, George F, et al., "Evaluation of Bone-Grafting Materials in a New Canine Segmental Spinal Fusion Model", Journal of Orthopaedic Research, vol. 11, No. 4, (Jul. 1993), 514-524.
Oxlund, H., et al., "The roles of hyaluronic acid, collagen and elastin in the mechanical properties of connective tissues", J Anat., 131(Pt 4), (Dec. 1980), 611-20.
St. John, K., et al., "Response of Canine Bone to a Synthetic Bone Graft Material", Clin. Mat., vol. 12, (1993), 49-55.
Thorne, et al., "CopiOs Injectible Paste Development Preliminary Disclosure Summary", (2004).
"Australian Application Serial No. 2007334213, Response filed Apr. 19, 2012 to First Examiners Report mailed Jan. 9, 2012", 9 pgs.
"Japanese Application Serial No. 1998535914, Office Action Mailed Jan. 24, 2012", W/ English Translation, 24 Pgs.
Cheung, D. T, et al., "The effect of gamma-irradiation on collagen molecules, isolated alpha-chains, and crosslinked native fibers.", J Biomed Mater Res., 24(5), (May 1990), 581-9.
Chu, C. C, et al., "The effect of gamma irradiation on the enzymatic degradation of polyglycolic acid absorbable sutures", J Biomed Mater Res., 17(6), (Nov. 1983), 1029-40.
Hallfeldt, K. K, et al., "Sterilization of partially demineralized bone matrix: the effects of different sterilization techniques on osteogenetic properties", J Surg Res., 59(5), (Nov. 1995), 614-20.
Hamada, K., et al., "Hydrothermal modification of titanium surface in calcium solutions", Biomaterials, 23, (2002), 2265-2272.
Ho, Hsiu-O, et al., "Characterization of collagen isolation and application of collagen gel as a drug carrier", Journal of Controlled Release, 44, (1997), 103-112.
Ijiri, S., et al., "Effect of sterilization on bone morphogenetic protein", J Orthop Res., 12(5), (Sep. 1994), 628-36.
Katz, R. W, et al., "Radiation-sterilized insoluble collagenous bone matrix is a functional carrier of osteogenin for bone induction", Calcif Tissue Int., 47(3), (Sep. 1990), 183-5.
Kim, H. M, et al., "Effect of heat treatment on apatite-forming ability of Ti metal induced by alkali treatment", J Mater Sci Mater Med., 8(6), (Jun. 1997), 341-7.
Lee, K. Y, et al., "Preparation of Caclium Phosphate Paste Composites with Demineralized Bone Matrix", Key Engineering Materials, (vols. 330-332), (2007), 803-806.
Legeros, Racquel Zapanta, "Calcium Phosphate-Based Osteoinductive Materials", Chem. Rev., 108, (2008), 4742-4753.
Liu, B., et al., "The effect of gamma irradiation on injectable human amnion collagen", J Biomed Mater Res., 23(8), (Aug. 1989), 833-44.

(56) References Cited

OTHER PUBLICATIONS

Munting, E., et al., "Effect of sterilization on osteoinduction. Comparison of five methods in demineralized rat bone", Acta Orthop Scand., 59(1), (Feb. 1988), 34-8.
Puolakkainen, "The effect of sterilization on transforming growth factor beta isolated from demineralized human bone", Transfusion, 33(8), (Aug. 1993), 679-85.
Raptopoulou-Gigi, M., et al., "Antimicrobial proteins in sterilised human milk", Br Med J., 1(6052), (Jan. 1, 1977), 12-4.
Reid, B. D, et al., "Gamma processing technology: an alternative technology for terminal sterilization of parenterals", PDA J Pharm Sci Technol., 49(2), (Mar.-Apr. 1995), 83-9.
Schwarz, N., et al., "Irradiation-sterilization of rat bone matrix gelatin", Acta Orthop Scand., 59(2), (Apr. 1988), 165-7.
Soboleva, N. N, et al., "Radiation resistivity of frozen insulin solutions and suspensions", Int J Appl Radiat Isot., 32(10), (Oct. 1981), 753-6.
Su, D., et al., "Sterilization of collagen matrix containing protein growth factors using gamma and electron beam irradiation", Pharmaceutical Research, 12(9), Abstract BIOTEC 2035, (1995), S-87.
Tezcaner, A., et al., "Fundamentals of tissue engineering: Tissues and applications", Technology and Health Care, 10, (2002), 203-216.
Tofighi, A., "Calcium Phosphate Cement (CPC): A Critical Development Path", Key Engineering Materials, (vols. 361-363), (2008), 303-306.
Wientroub, S., et al., "Influence of irradiation on the osteoinductive potential of demineralized bone matrix", Calcif Tissue Int., 42(4), (Apr. 1988), 255-60.
"U.S. Appl. No. 12/180,035, Notice of Allowance mailed Mar. 25, 2013", 6 pgs.
"Characterization of Osteoinductive Potential", Orthovita Products, http://www.orthovita.com/products/vitoss/osteoinductive.html, (Jan. 2004), 3 pgs.
"Chondrogenesis and Osteogenesis: Growth Factors", Abstract Nos. 917-921, 162a.
"Collagraft bone Graft Matrix (Contraindications)", Distributed by Zimmer, Inc., Warsaw, Indiana, (Sep. 1992), 1 pg.
"Collagraft Bone Graft Matrix (Indications)", Distributed by Zimmer, Inc., Warsaw, Indiana, (Sep. 1992), 1 pg.
"Collagraft Bone Graft Matrix (Nonosteoinductive Bone Void Filler)", Distributed by Zimmer, Inc., Warsaw, Indiana, (Sep. 1992), 1 pg.
"Collagraft Bone Graft Matriz Strip", Distributed by Zimmer, Inc., Warsaw, Indiana, (Feb. 1994), 6 pgs.
"Collagraft Bone Graft Substitute (Physician Package Insert)", Distribute by Zimmer, Inc., Warsaw, Indiana, (Mar. 1989), 1 pg.
"Fundamentals of Bone Physiology", Therics, (Jul. 2006), 5 pgs.
"OP-1: The First Name in BMPs", Stryker Biotech, http://www.opl.com/home.cfm?countryID=5, (Jan. 2004), 3 pgs.
"Osteoinductive", Scientific.net, [Online]. Retrieved from the Internet: <URL: http://www.scientific.net/Osteoinductive.htm>, (Jan. 2004), 1 pg.
"Spinal Technologies:INFUSE Bone Graft/LT-CAGE Lumbar Tapered Fusion Device", Medtronic Sofamor Danek, http://www.medtronicsofamordanek.com/patient-spinal-infuse.html, (Jan. 23, 2004), 4 pgs.
"The Organization of Skeletal Tissues", The Architecture and Cellular Elements of Bone, (Oct. 2000), 4 pgs.
Alpaslan, C., et al., "Bone reaction to subperiosteally implanted hydroxyapatite/collagen/glycosaminoglycans and coral in the guinea pig", Oral Surg. Oral Med. Oral Path., vol. 77, No. 4 (1994), 335-340, 5 pgs.
Asahina, I., et al., "Repair of Bone Defect in Primate Mandible using a Bone Morphogenetic Protein (BMP)-Hydroxyapatite-Collagen Composite", J. Med. Dent. Sci., vol. 44, (1997), 63-70.
Bar-Shavit, Z., et al., "Glucocorticoids Modulate Macrophage Surface Oligo saccharides and Their Bone Binding Activity", J. Clin. Invest., vol. 73, (1984), 1277-1283.
Benque, E., et al., "Tomodensitometric and Histologic Evaluation of the Combined Use of a Collagen Membrane and a HydroxyapatiteSpacer for Guided Bone Regeneration: A Clinical Report", Int. J. Oral Maxillofac. Implants, vol. 14, (1999), 258-264.
Block, et al., "Glycol Methacrylate Embedding Technique Emphasizing Cost Containment, Ultrarapid Processing, and Adaptability to a Variety of Staining Techniques", Laboratory medicine 13(5), (May 1982), 290-298.
Boden, Scott D, et al., "Evaluation of a Bovine-Derived Osteoinductive Bone Protein in a Nonhuman Primate Model of Lumbar Spinal Fusion", American Academy of Orthopaedic Surgeons 1996 Annual Meeting—Scientific Program, http://www.aaos.org/wordhtml/anmeet96/sciprog/073.htm, (Feb. 1996), 2 pgs.
Burwell, R. G, "The function of bone marrow in the incorporation of a bone graft.", Clin Orthop Relat Res., 200, (Nov. 1985), 125-141.
Cheng, Hongwei, et al., "Osteogenic Activity of the Fourteen Types of Human Bone Morphogenetic Proteins (BMPs)", The Journal of Bone & Joint Surgery 85-A (8), (Aug. 2003), 1544-1552.
Damien, Christopher J, et al., "Bone Graft and Bone Graft Substitutes: a Review of Current Technology and Applications", Journal of Applied Biomaterials, vol. 2, (1991), 187-208.
Endres, M., et al., "Osteogenic Induction of Human Bone Marrow-Derived Mesenchymal Progenitor Cells in Novel Synthetic Polymer-Hydrogel Matrices", Tissue Engineering, vol. 9, No. 4, (2003), 689-702.
Galbavy, S., et al., "AtelocollagenlHydroxylapatite Composite Material as Bone Defects Fillers in the Experiment on Rats", Bratisl. Med. J., vol. 96, (1995), 368-370.
Grigoryan, A., et al., "Time Course of Bone Defect Healing After Implantation in Them of Collagen-Hydroxyapatite Complexes: Experimental and Morphological Study", Stomatologia, vol. 75, (1996), 13-16.
Guillemin, et al., "The use of coral as a bone graft substitute", J. Biomed. Mat. Res. 21, (1987), 557-567.
Hamson, K., et al., "Preliminary Experience with a Novel Model Assessing In Vivo Mechanical Strength of Bone Grafts and Substitute Materials", Calcif. Tissue Int., vol. 57, (1995), 64-68.
Ho, Hsiu-O, et al., "Characterization of collage isolation and application of collagen gel as a drug carrier", Journal of controlled release, vol. 44, (1997), 103-111.
Hott, et al., "Ceramics in Substitutive and Reconstructive Surgery", P. Vincenzini, ed.,, (1991), 345-352.
Hsu, F., et al., "Microspheres of hydroxyapatite Ire constituted collagen as supports for osteoblast cell growth", Biornaterials, vol. 20, (1999), 1931-1936.
Ito, M., et al., "In vitro properties of a chitosan-bondedhydroxyapatite bone filling paste", Biomaterials, vol. 12, (41-45), 1991.
Itoh, Takashi, et al., "Structural Analysis of Collagen Fibrils in Rat Skin Based on Small-Angle X-Ray-Diffraction Pattern", Jpn. J. Appl. Phys., Part 1, No. 12A, (1996), 6172-6179.
Katthagen, B., et al., "Experimental Animal Investigation of Bone Regeneration with Collagen-Apatite", Arch. Orthop. Trauma Surg. vol. 103, (1984), 291-302.
Kocialkowski, et al., "Bone Grafts, Derivatives & Substitutes", Collagraft Combined with Autogeneic Bone Marrow: Experimental and Clinical Results, Chapter 14, (1994), 271-290.
Kocialkowski, A., et al., "Clinical Experience with a New Artificial Bone Graft: Preliminary Results of a Prospective Study", Injury: The British Journal of Accident Surgery, vol. 21, (1990), 142-144.
Lane, et al., "The Use of Composite Bone Graft Materials in a Segmental Femoral Defect Model in the Rat", J. Orthop. Trauma 2 (1) (abstract), (1988), 57-58.
Linder, L., et al., "Electron Microscopic Analysis of the Bone-Titanium Interface", Acta Orthop. Scand., vol. 54, (1983), 45-52.
Lindholm, T., et al., "The role of autogeneic bone marrow in the repair of a skull trephine defect filled with hydroxyapatite granules in the rabbit", Int. J. Oral Maxillofac. Surg., vol. 23, (2004), 306-311.
Liu, Y. M, et al., "2714 Osteoinductive Implants: The mis-en-scene for drug-bearing biomimetic coatings", Osteoinductive Implants, http://iadr.confex.com/iadr/2004Hawaii/techprogram/abstract_40044.htm, (Jan. 2004), 1 pg.
McIntyre, et al., "Characterization of a Bioceramic Composite for Repair of Large Bone Defects", Ceramic Bulletin 70 (9), (1991), 1499-1503.

(56) References Cited

OTHER PUBLICATIONS

Mehlisch, D., et al., "Histologic evaluation of the bonelgraft interface after mandibular augmentation with hydroxylapatitelpurified fibrillar collagen composite implants", Oral Surg. Oral Med. Oral Pathol., vol. 70, (1990), 685-692.

Minabe, M., et al., "Histological Study fo the Hydroxyapatite-Collagen Complex Implants in Periodontal Osseous Defects in Dogs", J.Periodontol.,, (Oct. 1988), 671-678.

Mittelmeier, H., et al., "Clinical Experience in the Implantation of Collagen-Apatite for Local Bone Regeneration", Z. Orthop., vol. 121, (1983), 115-123.

Nathan, et al., "Osteogenesis in Rats With an Inductive Bovine Composite", Journal of Orthopaedic Research 6, (1993), 325-334.

Nathan, Ranga M, et al., "Osteogenesis in Rats with an Inductive Bovine Composite", Journal of Orthopaedic Research, vol. 6, No. 3, (1988), 324-334.

Ohura, Kouichiro, et al., "Healing of Segmental Bone Defects in Rats Induced by a Beta-TCP-MCPM Cement Combined with rhBMP-2", Journal of Biomedical Materials Research 44(2), (1999), 168-175.

Pasquier, G., et al., "Injectable percutaneous bone biomaterials: an experimental study in a rabbit model", J. Mat. Sci. Mat. Med., vol. 7, No. 11, (1996), 683-690.

Peng, Y, et al., "Transcriptional Characterization of Bone Morphogenetic Proteins (BMPs) Mediated Osteogenic Signaling", J. Cell Biochem. vol. 90, No. 6, http://www.ncbi.nlm.nih.gov/entrez/query.fcgi?cmd=Retrieve&db=PubMed&list_uids=14, (Dec. 2003), 1149-1165.

Pohunkova, H., et al., "Reactivity and the fate of some composite bioimplants based on collagen in connective tissue", Biomaterials, vol. 16, (1995), 67-71.

Ronziere, et al., "Analysis of types I, II, III, IX and XI collagens synthesized by fetal bovine chondrocytes in high-density culture", Osteoarthritis and Cartilage 5, (1997), 205-214.

Rosenblatt, et al., "Injectable Collagen as a pH-sensitive hydrogel", Biomaterials, vol. 15, No. 12, (1994), 985-995.

Rovira, A., et al., "Colonization of a calcium phosphate/elastin-solubilized peptide-collagen composite material by human osteoblasts", Biomaterials, vol. 17, (1996), 1535-1540.

Sampath, et al., "Isolation of Osteogenin, an extracellular matrix-associated, bone-inductive protein, by heparin affinity chromatography", Proc. Natl. Acad. Sci USA 84, (Oct. 1987), 7109-7113.

Stone, et al., "Porcine and Bovine Cartilage Transplants in Cynomolgus Monkey", Transplantation, vol. 63, No. 5, Williams & Wilkins, USA, (Mar. 15, 1997), 640-645.

Suganuma, J., et al., "In vivo Evaluation of Collagen-Coated Dacron Fiber in Bone", Clin. Mat., vol. 15, (1994), 43-50.

Takagi, Katsumasa, et al., "The Role of Bone Marrow in Bone Morphogenetic Protein-induced Repair of Femoral Massive Diaphyseal Defects", Clinical Orthopaedics and Related Research, vol. 171, (Dec. 1982), 224-231.

Truumees, et al., "Alternatives to Autologous Bone Harvest in Spine Surgery", The University of Pennsylvania Orthopaedic Journal 12, USA, (1999), 77-88.

Zardiackas, Lyle D, et al., "Torsional Properties of Healed Canine Diaphyseal Defects Grafted with a Fibrillar Collegen and Hydroxyapatite/Tricalcium Phosphate Composite", Journal of Applied Biomaterials 5, (1994), 277-283.

Zerwekh, Joseph E, et al., "Fibrillar Collagen-Biphasic Calcium Phosphate Composite as a Bone Graft Substitute for Spinal Fusion", Journal of Orthopaedic Research, vol. 10, No. 4, (1992), 562-572.

"U.S. Appl. No. 13/297,005, Non Final Office Action mailed Oct. 10, 2012", 13 pgs.

"Canadian Application Serial No. 2,673,337, Office Action mailed Sep. 9, 2012", 3 pgs.

"Japanese Application Serial No. 1998535914, Response filed Jul. 24, 2012 to Office Action mailed Jan. 24, 2012", 6 pgs.

"U.S. Appl. No. 12/180,035, Non Final Office Action mailed Nov. 28, 2012", 9 pgs.

"U.S. Appl. No. 13/297,005, Response filed Jan. 10, 2013 to Non Final Office Action mailed Oct. 10, 2012", 10 1pgs.

"Japanese Application Serial No. 1998535914, Response filed Jul. 24, 2012 to Office Action mailed Jan. 24, 2012", (w/ English Translation of Claims), 16 pgs.

"Japanese Application Serial No. 2009-543018, Office Action mailed Dec. 4, 2012", (w/ English Translation), 5 pgs.

"Tri-Calcium Phosphates as a Biomaterial", [Online]. Retrieved from the Internet: <URL: http://www.scribd.com/doc/56970573/Tri-Calcium-Phosphates-as-a-Biomaterial>, (Upload Date: Jun. 2, 2011), 5 pgs.

Chakkalakal, D A, et al., "Mineralization and pH relationships in healing skeletal defects grafted with demineralized bone matrix", Journal of Biomedical Materials Research vol. 28,, (1994), 1439-1443.

Donlon, William, "Immune Neutrality of Calf Skin Collagen Gel Used to Stimulate Revitalization in Pulpless Open Apex Teeth of Rhesus Monkeys", J Dent Res, (Jun. 1977), 670-673.

Kohles, S S, et al., "A Morphometric Evaluation of Allograft Matrix Combinations in the Treatment of Osseous Defects in a Baboon Model", Calcif. Tissue Int. 67, (2000), 156-162.

Legeros, R Z, et al., "In Vitro Formation of Dicalcium Phosphate Dihydrate, $CaHPO_4.2h_2o$ (DCPD)", Scanning Electron Micropscopy, (1983), 407-418.

Legeros, R Z, et al., "The Nature of the Calcified Material Induced by Collagen-Calcium Phosphate Gel in Tooth", Dental Research vol. 57, Special Issue A, Abstract only. Abstract No. 527, (Jan. 1978), 206.

Legeros, Racquel Z, "Biodegradation and Bioresorption of Calcium Phosphate Ceramics", Clinical Materials 14, (1993), 65-88.

Legeros, Raquel Zapanta, "Apatites in Biological Systems", Prog. Crystal Growth Charact. vol. 4, (1981), 1-45.

Lenart, G, et al., "Some Basic Problems in the Examination of the Calcium Hydrogen Phosphates of Bone", Clinical Orthopaedics and Related Research, (1972), 263-272.

Nancollas, G H, et al., "Seeded Growth of Calcium Phosphates: Effect of Different Calcium Phosphate Seed Material", J. Dent. Res. vol. 55, No. 4, (1976), 617-624.

Nevins, Alan, et al., "Hard Tissue Induction Into Pulpless Open-Apex Teeth Using Collagen-Calcium Phosphate Gel", Journal of Endodontics vol. 3, Iss. 11, (1977), 431-433.

Nevins, Alan, et al., "Revitalization of pulpless open apex teeth in rhesus monkeys, using collagen-calcium phosphate gel", J Endod. 2(6), (1976), 159-65.

Roufosse, A. H, "Indentification of Burshite in Newly Deposited Bone Mineral from Embryonic Chicks", Journal of Ultrastructure Research 68, (1979), 235-255.

Tenhuisen, Kevor S, et al., "Formation and properties of a synthetic bone composite: Hydroxyapatite-collagen", Journal of Biomedical Materials Research vol. 29, (1995), 803-810.

Walsh, W R, et al., "Demineralized bone Matrix as a template for mineral-organic composites", Biomaterials 16, (1995), 1363-1371.

"U.S. Appl. No. 12/180,035, Response filed Feb. 28, 2013 to Non Final Office Action mailed Nov. 28, 2012", 6 pgs.

"Canadian Application Serial No. 2,673,337, Response filed Feb. 7, 2013 to Office Action mailed Aug. 9, 2012", 7 pgs.

Landesman, Richard, et al., "In Vivo Analysis of the Half-Life of the Osteoinductive Potential of Demineralized Bone Matrix using Diffusion Chambers", Calcif Tissue Int. vol. 45, (1989), 348-353.

Pappalardo, S, et al., "How to biomaterials affect the biological activities and responses of cells? An in-vitro study", Minerva Stomatol vol. 59, (2010), 445-464.

Urist, Marshall R, et al., "Preservation and Biodegration of the Morphogenetic Property of Bone Matrix", J. theor. Biol. vol. 38, (1973), 155-167.

"U.S. Appl. No. 13/297,005, Examiner Interview Summary mailed May 22, 2013", 3 pgs.

"U.S. Appl. No. 13/297,005, Notice of Allowance mailed Aug. 7, 2013", 12 pgs.

"U.S. Appl. No. 13/297,005, Response filed Jun. 24, 2013 to Final Office Action Mar. 22, 2013", 13 pgs.

"Australian Application Serial No. 2012204139, First Examiner Report mailed Apr. 10, 2013", 3 pgs.

(56) References Cited

OTHER PUBLICATIONS

"Canadian Application Serial No. 2,673,337, Office Action mailed Mar. 26, 2013", 2 pgs.

"European Application Serial No. 07864863.1, Examination Notification Art. 94(3) mailed Mar. 5, 2013", 4 pgs.

"International Application Serial No. PCT/US2011/060823, International Preliminary Report on Patentability mailed May 30, 2013", 6 pgs.

Weadock, K., et al., "Evaluation of collagen crosslinking techniques", Biomater Med Devices Artif Organs., 11(4), (1983-1984), 293-318.

* cited by examiner

|  | EXPLANT MASS | | | | EXPLANT MASS - NORMALIZED | | | |
|  | CPB | | CB | | CPB | | CB | |
|  | AVG | ±SD | AVG | ±SD | AVG | ±SD | AVG | ±SD |
|---|---|---|---|---|---|---|---|---|
| $Ca(H_2PO_4)_2$ (MCP) | 71.2 | 17.0 | 84.8 | 11.0 | 84.7 | 20.2 | 100.8 | 15.5 |
| $CaHPO_4 \cdot 2H_2O$ (DCP) | 157.2 | 22.4 | 91.6 | 10.6 | 173.0 | 24.7 | 100.8 | 15.5 |
| $2CaO \cdot P_2O_5 \cdot 2H_2O$ (CP) | 191.8 | 24.6 | 98.6 | 13.7 | 196.1 | 25.2 | 100.8 | 15.5 |
| $3CaO \cdot P_2O_5$ (TCP) | | | | | | | | |
| $3.33CaO \cdot P_2O_5$ (HA-am) | 134.8 | 15.2 | 144.8 | 29.8 | 93.9 | 10.6 | 100.8 | 15.5 |
| $3.33CaO \cdot P_2O_5$ (HA-am) | 136.2 | 39.9 | 103.8 | 13.4 | 132.3 | 38.8 | 100.8 | 15.5 |
| $3.33CaO \cdot P_2O_5$ (HA-x) | 109.0 | 18.1 | 116.2 | 8.6 | 94.6 | 15.7 | 100.8 | 15.5 |
| $4CaO \cdot P_2O_5$ (TTCP) | 46.8 | 18.8 | 115.0 | 5.9 | 41.0 | 16.5 | 100.8 | 15.5 |
| $CaCO_3$-ARAGONITE | 96.6 | 41.0 | 123.2 | 15.1 | 79.1 | 33.6 | 100.8 | 15.5 |
| $CaCO_3$-CALCITE | 73.4 | 24.1 | 102.2 | 17.6 | 72.4 | 23.8 | 100.8 | 15.5 |
| ProOsteon 200R-acidi | 87.5 | 30.2 | 56.3 | 16.3 | 156.7 | 54.1 | 100.8 | 15.5 |
| ProOsteon 200R-neutr | 22.0 | 4.9 | 32.2 | 6.5 | 68.9 | 15.3 | 100.8 | 15.5 0.0 |
| Ostite C1 | 108.3 | 13.4 | 114.2 | 13.8 | 95.6 | 11.8 | 100.8 | 15.5 |
| Ostite C2 | 101.6 | 55.0 | 112.2 | 22.8 | 91.3 | 49.4 | 100.8 | 15.5 |
| Ostite C3 | 109.8 | 31.5 | 118.6 | 26.3 | 93.3 | 26.8 | 100.8 | 15.5 |
| GB9N BIOGLASS | 80.8 | 10.8 | 98.6 | 13.4 | 82.6 | 11.0 | 100.8 | 15.5 |

*FIG. 2B*

|  | HISTOLOGY SCORE | | | | HISTOLOGY SCORE - NORMALIZED | | | |
|---|---|---|---|---|---|---|---|---|
|  | CPB | | CB | | CPB | | CB | |
|  | AVG | ±SD | AVG | ±SD | AVG | ±SD | AVG | ±SD |
| $Ca(H_2PO_4)_2$ (MCP) | 1.7 | 0.6 | 2.3 | 0.6 | 1.9 | 0.7 | 2.6 | 0.4 |
| $CaHPO_4 \cdot 2H_2O$ (DCP) | 3.0 | 0.0 | 2.3 | 0.6 | 3.4 | 0.0 | 2.6 | 0.4 |
| $2CaO \cdot P_2O_5 \cdot 2H2O$ (CP) | 2.7 | 0.6 | 2.0 | 0.0 | 3.5 | 0.8 | 2.6 | 0.4 |
| $3CaO \cdot P_2O_5$ (TCP) |  |  |  |  |  |  |  |  |
| $3.33CaO \cdot P_2O_5$ (HA-am) | 1.3 | 0.6 | 2.0 | 0.0 | 1.7 | 0.8 | 2.6 | 0.4 |
| $3.33CaO \cdot P_2O_5$ (HA-am) | 2.0 | 0.0 | 3.0 | 0.0 | 1.7 | 0.0 | 2.6 | 0.4 |
| $3.33CaO \cdot P_2O_5$ (HA-x) | 1.2 | 0.4 | 2.4 | 0.5 | 1.3 | 0.4 | 2.6 | 0.4 |
| $4CaO \cdot P_2O_5$ (TTCP) | 1.0 | 0.0 | 2.0 | 0.0 | 1.3 | 0.0 | 2.6 | 0.4 |
| $CaCO_3$-ARAGONITE | 1.0 | 0.0 | 2.7 | 0.6 | 1.0 | 0.0 | 2.6 | 0.4 |
| $CaCO_3$-CALCITE | 1.0 | 0.0 | 2.7 | 0.6 | 1.0 | 0.0 | 2.6 | 0.4 |
| ProOsteon 200R-acidi | 2.8 | 1.0 | 4.4 | 0.5 | 1.7 | 0.6 | 2.6 | 0.4 |
| ProOsteon 200R-neutr | 2.0 | 0.0 | 2.4 | 0.5 | 2.2 | 0.0 | 2.6 | 0.4 |
| Ostite C1 | 1.0 | 0.0 | 3.0 | 0.0 | 0.9 | 0.0 | 2.6 | 0.4 |
| Ostite C2 | 1.7 | 0.6 | 2.3 | 0.6 | 1.9 | 0.7 | 2.6 | 0.4 |
| Ostite C3 | 1.7 | 1.2 | 2.7 | 0.6 | 1.6 | 1.2 | 2.6 | 0.4 |
| GB9N BIOGLASS | 2.0 | 1.0 | 2.7 | 0.6 | 1.9 | 1.0 | 2.6 | 0.4 |

*FIG. 3B*

|  | MINERAL CONCENTRATION | | | | MINERAL CONC. - NORMALIZED | | | |
|---|---|---|---|---|---|---|---|---|
|  | CPB | | CB | | CPB | | CB | |
|  | AVG | ±SD | AVG | ±SD | AVG | ±SD | AVG | ±SD |
| Ca(H$_2$PO$_4$)$_2$ (MCP) | 12.3 | 4.1 | 8.8 | 1.9 | 15.0 | 5.0 | 10.7 | 1.4 |
| CaHPO4.2H$_2$O (DCP) | 12.1 | 0.5 | 11.1 | 0.7 | 11.7 | 0.5 | 10.7 | 1.4 |
| 2CaO.P$_2$O$_5$.2H2O (CP) | 16.4 | 0.0 | 11.1 | 0.5 | 15.9 | 0.0 | 10.7 | 1.4 |
| 3CaO.P$_2$O$_5$ (TCP) |  |  |  |  |  |  |  |  |
| 3.33CaO.P$_2$O$_5$ (HA-am) | 18.2 | 0.3 | 8.3 | 1.8 | 23.5 | 0.4 | 10.7 | 1.4 |
| 3.33CaO.P$_2$O$_5$ (HA-am) | 18.1 | 3.2 | 8.5 | 1.4 | 22.9 | 4.0 | 10.7 | 1.4 |
| 3.33CaO.P$_2$O$_5$ (HA-x) | 18.5 | 0.6 | 13.3 | 1.4 | 14.9 | 0.5 | 10.7 | 1.4 |
| 4CaO.P$_2$O$_5$ (TTCP) | 17.8 | 5.0 | 13.7 | 0.9 | 13.9 | 3.9 | 10.7 | 1.4 |
| CaCO$_3$-ARAGONITE | 14.6 | 2.3 | 11.2 | 1.6 | 14.0 | 2.2 | 10.7 | 1.4 |
| CaCO$_3$-CALCITE | 12.2 | 3.0 | 10.0 | 1.6 | 13.1 | 3.2 | 10.7 | 1.4 |
| ProOsteon 200R-acidi | 19.3 | 7.2 | 15.3 | 4.2 | 13.5 | 5.1 | 10.7 | 1.4 |
| ProOsteon 200R-neutr | 25.4 | 2.8 | 16.4 | 3.2 | 16.6 | 1.8 | 10.7 | 1.4 |
| Ostite C1 | 26.6 | 1.8 | 8.1 | 0.7 | 35.2 | 2.4 | 10.7 | 1.4 |
| Ostite C2 | 23.6 | 4.5 | 8.3 | 0.5 | 30.5 | 5.8 | 10.7 | 1.4 |
| Ostite C3 | 25.7 | 5.7 | 7.4 | 0.5 | 37.3 | 8.3 | 10.7 | 1.4 |
| GB9N BIOGLASS | 15.6 | 0.1 | 9.5 | 0.8 | 17.6 | 0.1 | 10.7 | 1.4 |

*FIG. 4B*

|  | MINERAL MASS | | | | MINERAL MASS - NORMALIZED | | | |
|---|---|---|---|---|---|---|---|---|
|  | CPB | | CB | | CPB | | CB | |
|  | AVG | ±SD | AVG | ±SD | AVG | ±SD | AVG | ±SD |
| $Ca(H_2PO_4)_2$ (MCP) | 9.9 | 3.0 | 8.5 | 0.7 | 12.1 | 3.7 | 10.4 | 1.8 |
| $CaHPO4.2H_2O$ (DCP) | 18.2 | 3.6 | 10.5 | 2.2 | 18.0 | 3.6 | 10.4 | 1.8 |
| $2CaO.P_2O_5.2H2O$ (CP) | 33.3 | 2.4 | 11.8 | 0.8 | 29.2 | 2.1 | 10.4 | 1.8 |
| $3CaO.P_2O_5$ (TCP) | | | | | | | | |
| $3.33CaO.P_2O_5$ (HA-am) | 26.8 | 2.8 | 14.2 | 5.1 | 19.6 | 2.0 | 10.4 | 1.8 |
| $3.33CaO.P_2O_5$ (HA-am) | 26.8 | 7.0 | 9.6 | 1.9 | 28.9 | 7.6 | 10.4 | 1.8 |
| $3.33CaO.P_2O_5$ (HA-x) | 16.7 | 6.4 | 16.4 | 0.3 | 10.5 | 4.0 | 10.4 | 1.8 |
| $4CaO.P_2O_5$ (TTCP) | 14.3 | 7.8 | 14.1 | 1.6 | 10.5 | 5.7 | 10.4 | 1.8 |
| $CaCO_3$-ARAGONITE | 13.2 | 4.3 | 14.5 | 2.7 | 9.4 | 3.1 | 10.4 | 1.8 |
| $CaCO_3$-CALCITE | 8.2 | 4.2 | 8.6 | 1.8 | 9.9 | 5.1 | 10.4 | 1.8 |
| ProOsteon 200R-acidi | 10.3 | 3.3 | 5.5 | 1.6 | 19.4 | 6.2 | 10.4 | 1.8 |
| ProOsteon 200R-neutr | 6.6 | 2.0 | 4.0 | 1.8 | 17.1 | 5.2 | 10.4 | 1.8 |
| Ostite C1 | 34.5 | 5.7 | 8.5 | 1.3 | 42.0 | 6.9 | 10.4 | 1.8 |
| Ostite C2 | 20.8 | 1.3 | 10.7 | 0.1 | 20.1 | 1.3 | 10.4 | 1.8 |
| Ostite C3 | 25.8 | 1.3 | 9.7 | 1.6 | 27.6 | 1.4 | 10.4 | 1.8 |
| GB9N BIOGLASS | 11.8 | 2.7 | 8.8 | 0.4 | 13.9 | 3.2 | 10.4 | 1.8 |

*FIG. 5B*

|  | EXPLANT MASS | | | | EXPLANT MASS - NORMALIZED | | | |
|---|---|---|---|---|---|---|---|---|
|  | CPB | | CDB | | CPB | | CDB | |
|  | AVG | ±SD | AVG | ±SD | AVG | ±SD | AVG | ±SD |
| $Ca(H_2PO_4)_2$ (MCP) | 107.5 | 22.5 | 154.7 | 24.3 | 81.6 | 17.1 | 117.5 | 28.9 |
| $CaHPO_4.2H_2O$ (DCP) | 78.9 | 21.6 | 75.5 | 16.9 | 122.7 | 33.6 | 117.5 | 28.9 |
| $2CaO.P_2O_5.2H_2O$ (CP) | 98.9 | 27.0 | 55.8 | 36.1 | 208.2 | 56.8 | 117.5 | 28.9 |
| $3CaO.P_2O_5$ (TCP) | 11.7 | 15.3 | 83.2 | 20.7 | 16.5 | 21.6 | 117.5 | 28.9 |
| $3.33CaO.P_2O_5$ (HA-am) | 107.3 | 29.4 | 137.4 | 15.3 | 91.7 | 25.1 | 117.5 | 28.9 |
| $3.33CaO.P_2O_5$ (HA-am) | 124.6 | 25.6 | 130.2 | 29.4 | 112.4 | 23.1 | 117.5 | 28.9 |
| $3.33CaO.P_2O_5$ (HA-x) | 111.1 | 16.5 | 110.7 | 25.6 | 117.9 | 17.5 | 117.5 | 28.9 |
| $4CaO.P_2O_5$ (TTCP) | 41.1 | 16.0 | 116.9 | 16.0 | 41.3 | 16.1 | 117.5 | 28.9 |
| $CaCO_3$-ARAGONITE | 50.1 | 45.1 | 139.3 | 45.1 | 42.2 | 38.0 | 117.5 | 28.9 |
| $CaCO_3$-CALCITE | 68.0 | 21.0 | 191.0 | 21.0 | 41.8 | 12.9 | 117.5 | 28.9 |
| ProOsteon 200R-acidi | 74.7 | 13.6 | 80.4 | 29.1 | 109.1 | 21.4 | 117.5 | 28.9 |
| ProOsteon 200R-neutr | 29.2 | 6.0 | 35.5 | 12.7 | 96.6 | 24.1 | 117.5 | 28.9 0.0 |
| Ostite C1 | 123.0 | 46.3 | 167.3 | 28.5 | 86.3 | 4.2 | 117.5 | 28.9 |
| Ostite C2 | 82.9 | 21.2 | 146.3 | 28.6 | 66.3 | 37.2 | 117.5 | 28.9 |
| Ostite C3 | 127.0 | 26.6 | 157.5 | 31.2 | 94.7 | 15.8 | 117.5 | 28.9 |
| GB9N BIOGLASS | 52.8 | 20.5 | 97.5 | 22.6 | 63.6 | 24.7 | 117.5 | 28.9 |

*FIG. 6B*

|  | HISTOLOGY SCORE | | | | HISTOLOGY SCORE - NORMALIZED | | | |
|---|---|---|---|---|---|---|---|---|
|  | CPB | | CDB | | CPB | | CDB | |
|  | AVG | ±SD | AVG | ±SD | AVG | ±SD | AVG | ±SD |
| $Ca(H_2PO_4)_2$ (MCP) | 3.0 | 0.0 | 3.7 | 0.5 | 2.4 | 0.0 | 3.0 | 0.6 |
| $CaHPO_4 \cdot 2H_2O$ (DCP) | 4.0 | 0.6 | 3.8 | 0.6 | 3.1 | 0.5 | 3.0 | 0.6 |
| $2CaO \cdot P_2O_5 \cdot 2H_2O$ (CP) | 2.3 | 0.8 | 2.8 | 1.3 | 2.4 | 0.8 | 3.0 | 0.6 |
| $3CaO \cdot P_2O_5$ (TCP) | 1.0 | 0.0 | 3.7 | 0.5 | 0.8 | 0.0 | 3.0 | 0.6 |
| $3.33CaO \cdot P_2O_5$ (HA-am) | 1.3 | 0.5 | 2.4 | 0.7 | 1.6 | 0.6 | 3.0 | 0.6 |
| $3.33CaO \cdot P_2O_5$ (HA-am) | 1.1 | 0.3 | 1.8 | 0.6 | 1.8 | 0.5 | 3.0 | 0.6 |
| $3.33CaO \cdot P_2O_5$ (HA-x) | 1.3 | 0.5 | 2.7 | 0.5 | 1.4 | 0.5 | 3.0 | 0.6 |
| $4CaO \cdot P_2O_5$ (TTCP) | 1.0 | 0.0 | 2.7 | 0.5 | 1.1 | 0.0 | 3.0 | 0.6 |
| $CaCO_3$-ARAGONITE | 1.0 | 0.0 | 2.3 | 0.6 | 1.3 | 0.0 | 3.0 | 0.6 |
| $CaCO_3$-CALCITE | 1.0 | 0.0 | 3.0 | 0.0 | 1.0 | 0.0 | 3.0 | 0.6 |
| ProOsteon 200R-acidi | 2.5 | 0.6 | 4.0 | 0.0 | 1.8 | 0.4 | 3.0 | 0.6 |
| ProOsteon 200R-neutr | 2.0 | 0.0 | 2.6 | 0.9 | 2.3 | 0.0 | 3.0 | 0.6 |
|  |  |  |  |  |  |  |  | 0.0 |
| Ostite C1 | 1.9 | 0.8 | 3.1 | 0.4 | 1.8 | 0.8 | 3.0 | 0.6 |
| Ostite C2 | 2.1 | 0.8 | 2.9 | 0.3 | 2.1 | 0.8 | 3.0 | 0.6 |
| Ostite C3 | 1.8 | 0.6 | 3.2 | 0.4 | 1.7 | 0.6 | 3.0 | 0.6 |
| GB9N BIOGLASS | 1.0 | 0.0 | 2.5 | 0.6 | 1.2 | 0.0 | 3.0 | 0.6 |

*FIG. 7B*

|  | MINERAL CONCENTRATION | | | | MINERAL CONC. - NORMALIZED | | | |
|---|---|---|---|---|---|---|---|---|
|  | CPB | | CDB | | CPB | | CDB | |
|  | AVG | ±SD | AVG | ±SD | AVG | ±SD | AVG | ±SD |
| $Ca(H_2PO_4)_2$ (MCP) | 18.0 | 2.0 | 13.1 | 1.8 | 18.5 | 2.1 | 13.5 | 2.7 |
| $CaHPO_4.2H_2O$ (DCP) | 11.9 | 2.7 | 13.0 | 2.1 | 12.3 | 2.8 | 13.5 | 2.7 |
| $2CaO.P_2O_5.2H2O$ (CP) | 17.3 | 2.5 | 11.3 | 1.0 | 20.6 | 3.0 | 13.5 | 2.7 |
| $3CaO.P_2O_5$ (TCP) | 7.6 | 7.0 | 14.4 | 1.8 | 7.1 | 6.6 | 13.5 | 2.7 |
| $3.33CaO.P_2O_5$ (HA-am) | 24.6 | 2.4 | 12.6 | 2.1 | 26.3 | 2.6 | 13.5 | 2.7 |
| $3.33CaO.P_2O_5$ (HA-am) | 18.3 | 4.7 | 13.0 | 1.4 | 19.0 | 4.9 | 13.5 | 2.7 |
| $3.33CaO.P_2O_5$ (HA-x) | 18.9 | 2.5 | 14.1 | 2.6 | 18.1 | 2.4 | 13.5 | 2.7 |
| $4CaO.P_2O_5$ (TTCP) | 13.1 | 4.4 | 13.6 | 2.1 | 13.0 | 4.4 | 13.5 | 2.7 |
| $CaCO_3$-ARAGONITE | 14.5 | 3.3 | 14.2 | 4.0 | 13.8 | 3.1 | 13.5 | 2.7 |
| $CaCO_3$-CALCITE | 12.3 | 3.0 | 12.3 | 3.0 | 13.5 | 3.3 | 13.5 | 2.7 |
| ProOsteon 200R-acidi | 19.1 | 1.3 | 15.6 | 2.6 | 16.5 | 1.1 | 13.5 | 2.7 |
| ProOsteon 200R-neutr | 22.6 | 2.8 | 23.2 | 15.2 | 13.1 | 1.6 | 13.5 | 2.7 |
| Ostite C1 | 22.2 | 5.4 | 9.9 | 2.1 | 30.2 | 7.3 | 13.5 | 2.7 |
| Ostite C2 | 22.6 | 3.3 | 12.0 | 2.8 | 25.4 | 3.7 | 13.5 | 2.7 |
| Ostite C3 | 23.2 | 3.8 | 11.5 | 2.8 | 27.2 | 4.5 | 13.5 | 2.7 |
| GB9N BIOGLASS | 18.7 | 3.3 | 11.7 | 0.8 | 21.5 | 3.8 | 13.5 | 2.7 |

*FIG. 8B*

|  | MINERAL MASS | | | | MINERAL MASS - NORMALIZED | | | |
|---|---|---|---|---|---|---|---|---|
|  | CPB | | CDB | | CPB | | CDB | |
|  | AVG | ±SD | AVG | ±SD | AVG | ±SD | AVG | ±SD |
| $Ca(H_2PO_4)_2$ (MCP) | 17.3 | 2.6 | 18.4 | 3.1 | 13.9 | 2.1 | 14.8 | 3.5 |
| $CaPO4.2H_2O$ (DCP) | 9.4 | 2.2 | 9.6 | 3.2 | 14.5 | 3.4 | 14.8 | 3.5 |
| $2CaO.P_2O_5.2H2O$ (CP) | 13.3 | 5.3 | 6.3 | 1.1 | 31.2 | 12.4 | 14.8 | 3.5 |
| $3CaO.P_2O_5$ (TCP) | 1.1 | 1.3 | 11.2 | 1.6 | 1.5 | 1.7 | 14.8 | 3.5 |
| $3.33CaO.P_2O_5$ (HA-am) | 26.2 | 8.3 | 16.5 | 2.8 | 23.5 | 7.4 | 14.8 | 3.5 |
| $3.33CaO.P_2O_5$ (HA-am) | 28.9 | 14.7 | 18.5 | 3.3 | 23.1 | 11.8 | 14.8 | 3.5 |
| $3.33CaO.P_2O_5$ (HA-x) | 17.7 | 6.4 | 15.9 | 0.9 | 16.5 | 6.0 | 14.8 | 3.5 |
| $4CaO.P_2O_5$ (TTCP) | 5.8 | 3.4 | 16.0 | 3.9 | 5.4 | 3.1 | 14.8 | 3.5 |
| $CaCO_3$-ARAGONITE | 12.1 | 7.2 | 15.6 | 3.5 | 11.5 | 6.8 | 14.8 | 3.5 |
| $CaCO_3$-CALCITE | 14.2 | 9.2 | 17.7 | 8.5 | 11.9 | 7.7 | 14.8 | 3.5 |
| ProOsteon 200R-acidi | 14.7 | 4.3 | 15.6 | 7.0 | 13.9 | 4.1 | 14.8 | 3.5 |
| ProOsteon 200R-neutr | 5.9 | 1.6 | 9.2 | 4.4 | 9.5 | 2.6 | 14.8 | 3.5 |
| Ostite C1 | 22.9 | 14.0 | 17.7 | 2.8 | 19.1 | 11.7 | 14.8 | 3.5 |
| Ostite C2 | 17.3 | 3.5 | 13.9 | 3.4 | 18.4 | 3.7 | 14.8 | 3.5 |
| Ostite C3 | 26.1 | 7.6 | 20.6 | 2.8 | 18.7 | 5.5 | 14.8 | 3.5 |
| GB9N BIOGLASS | 10.9 | 4.9 | 14.0 | 2.8 | 11.5 | 5.2 | 14.8 | 3.5 |

*FIG. 9B*

# COMPOSITION AND PROCESS FOR BONE GROWTH AND REPAIR

CROSS-REFERENCE TO RELATED APPLICATION

This application is a continuation of co-pending U.S. application Ser. No. 11/383,309 filed May 15, 2006.

This application is a continuation-in-part of prior copending U.S. patent application Ser. No. 09/746,921, filed Dec. 22, 2000.

FIELD OF THE INVENTION

The present invention relates to methods and compositions for the induction of bone growth in mammals and to methods for the production of such compositions.

BACKGROUND

A number of diseases or injuries involving bones are known for which repair, regeneration, or augmentation of bone is a desired treatment. Formation of bone in vivo involves an interaction of various inductive proteins which act by causing a differentiation of mesenchymal cells into cartilage and then bone-forming cell lines. This mechanism is not completely understood. However, in efforts to improve orthopedic procedures, purified protein mixtures and recombinantly produced proteins have been developed which stimulate osteoinductive activity.

In general, autogeneous bone grafts have been viewed as the standard for restoring skeletal defects. However, autogeneous sources of bone in human beings are limited, expensive and painful to obtain. Accordingly, materials such as demineralized bone matrix have been developed to augment or replace autogeneous bone grafts. However, an alternative to demineralized bone matrix is desired to improve the ease of use, economy of product manufacture and to eliminate the potential of disease transfer or immune system incompatibilities. To date however, an acceptable substitute has not been identified.

Currently the clinical potential of composite implants containing a mixture of bovine tendon collagen and a proprietary bone morphogenic protein mixture, with demineralized bone matrix powders and simulated body fluid is being evaluated. While a number of advances have improved the activity of osteoinductive factors such as those present in bone morphogenic protein mixtures, their clinical application has been limited, in part, by the requirement for a superior delivery vehicle. Resistance to the use of demineralized bone matrix in certain cultures, as well as the desire to enhance the activity of the bone morphogenic protein mixture to reduce cost, speaks to the desire to develop substitutes for demineralized bone matrix.

The present invention provides compositions that can be used as bone graft substitutes to obtain a product with an improved osteoinductive response for growth factors in degradable implants for skeletal regeneration. The compositions of the present invention are easier to use and more economical to manufacture than demineralized bone matrix, and they eliminate or significantly reduce the potential of both disease and pathogen transfer and immune system incompatibilities.

Numerous materials have been experimentally evaluated as alternative delivery vehicles for osteoinductive growth factors. The materials previously assessed by reconstructive surgeons and scientists include, without limitation, hydroxyapatites, tricalcium phosphates, aliphatic polyesters, cancellous bone allografts, human fibrin, plaster of paris, apatite wollastonite glass ceramics, titanium, devitalized bone matrix, non-collagenous proteins, collagen and autolyzed antigen extracted allogenic bone. None of these materials have been found to be entirely satisfactory.

Other growth factor carriers containing calcium phosphate additives have been developed. For example, a macroporous collagen sponge containing a mixture of a-tricalcium phosphate ($\alpha$-3CaO.P$_2$O$_5$) and hydroxyapatite (3.33CaO.P$_2$O$_5$(OH)$_2$) has been developed. Alternatively, a macroporous collagen sponge that contains precipitated hydroxyapatite has also been disclosed (U.S. Pat. No. 5,776,193). The composition of such products are consistent with the prevailing view that hydroxyapatite is the preferred calcium phosphate source for bone graft substitutes or extenders due to its compositional similarity with the mineral component of natural bone.

There remains a desire for improved compositions for the induction of bone growth in animals that address the problems of existing compositions and products.

SUMMARY

As noted above, hydroxyapatite has long been considered a preferred source of calcium phosphate in bone graft substitutes. Indeed, evidence suggests that the inclusion of hydroxyapatite in bone graft substitutes does provide benefits related to osteoblast adherence. Thus, hydroxyapatite shares a compositional similarity to naturally occurring bone mineral and stimulates certain elements of the bone formation cascade. Certain hydroxyapatite bone graft substitutes have also been preferred as they are generally characterized by having a neutral or basic pH when implanted under normal physiological conditions. Despite these long-believed potential benefits and the resultant preference for hydroxyapatite containing bone growth substitutes, the inventor has now shown that the addition of calcium phosphate materials having a neutral or basic pH, such as hydroxyapatite, to collagen actually hinders the osteoinductive activity of bone growth proteins in vivo.

The present invention is directed to a bone growth composition which includes an acidic substrate and a bone growth protein, wherein the bone growth protein is characterized as having a first activity at neutral or basic pH and a second, higher activity at acidic pH. The acidic substrate preferably comprises a source of calcium and a source of phosphate. The composition also may include an acidic buffering potential in physiological solution. In another embodiment, the composition further includes a biocompatible buffering agent to maintain the acidity of the composition. In further alternative embodiments, the sources of calcium and/or phosphate can be salts such as monocalcium phosphate, calcium hydrogen phosphate dihydrate, or calcium pyrophosphate. The substrate can comprise collagen, fibrin, alginate, one or more synthetic polymers (such as polyethylene glycol (PEG), functionalized PEG, aliphatic polyesters, polylactic acid (PLA), or polyglycolic acid (PGA)), or mixtures thereof. The bone growth protein can be one or more purified bone growth proteins (each protein can be purified independently or collectively from allograft, xenograft, or autograft bone), recombinantly produced bone growth proteins, or mixtures thereof. In a preferred embodiment, the bone growth protein includes a purified bone growth protein composition known as Bone Protein Mixture or BPM.

An embodiment of the present invention also includes a process for producing an implantable bone growth composition. The process includes producing a dispersion of collagen fibrils containing a solubilized sodium phosphate salt. The process may further include adding a calcium chloride salt to the dispersion of collagen fibrils to precipitate a calcium phosphate salt onto the surface of the collagen fibrils to produce an implantable bone growth composition. Alternatively, the process can include making the dispersion with a calcium salt and adding a phosphate salt.

The present invention also includes a process for the induction of bone formation in a mammal, which includes implanting a bone growth composition of the present invention in a mammal. Such a process can include the use of the bone growth composition in a joint replacement operation (e.g., hip, knee, shoulder, elbow, or ankle, among others), a spinal fusion, repair of periodontal defects, treatment of osteoporosis, skeletal augmentation, repair of bone defects, or repair of bone fractures.

The composition of the present invention and products made therewith are superior materials for use as a demineralized bone matrix replacement. It has been found that the calcium source, the phosphate source, their collective pH, and the acidic buffering potential each have independent beneficial effects for bone growth induced by the present composition. In addition, the novel processing technology for producing such materials produces collagen sponges with dramatically superior physical properties. The products are collagen dispersions containing a calcium phosphate salt on the surface of the collagen fibrils, resulting in the formation of water stable, collagen sponges with superior physical properties. Composite products provide both improved physical properties and superior osteoinductive performance. The products can be rapidly and cost-effectively manufactured, and can reduce the required doses of osteoinductive proteins. These composites provide significant economic savings and eliminate potential disease transfer due to the elimination of the use of demineralized bone matrix. Additionally, the composites provide more reproducible clinical results, allow simpler surgical application, and better maintain physical dimensions during use.

DETAILED DESCRIPTION

Figure 18:
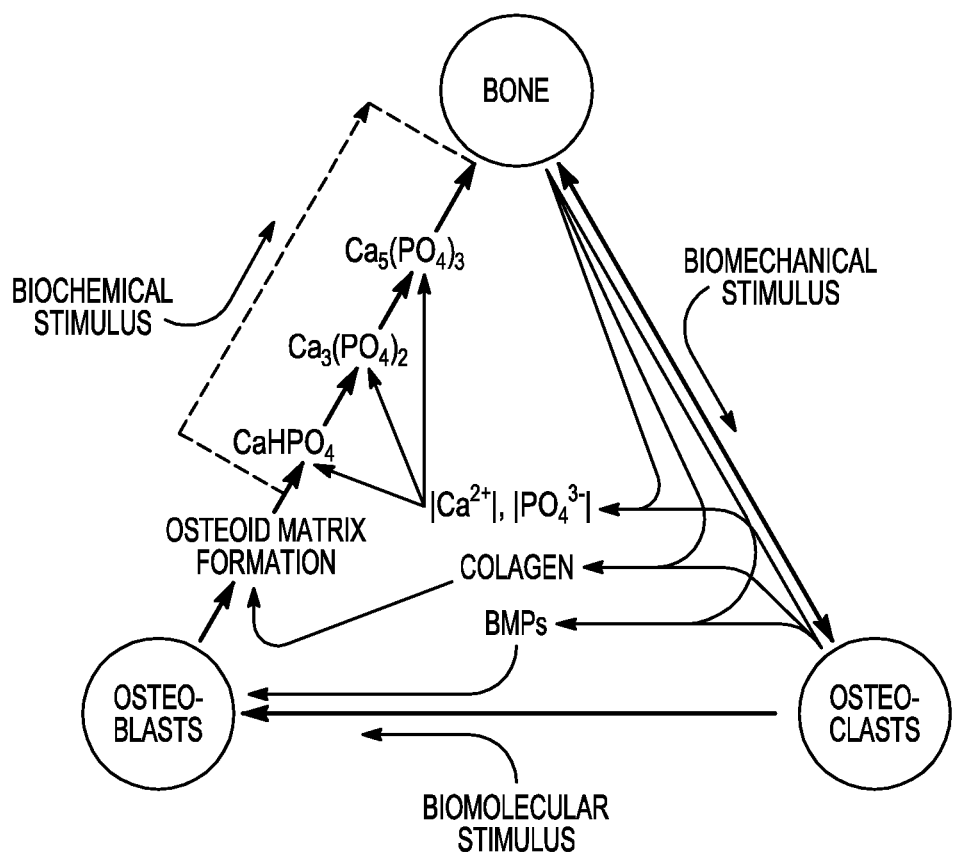
FIG. 18: Overview of natural metabolic regulation of bone remodeling and healing.

The natural process of bone resorption and subsequent bone reformation occurs throughout a person's life. The process is initiated by biomechanical stimuli and localized micro-damage to skeletal tissues. Osteoclast bone resorption locally releases essential components required for bone repair and bone reformation, including: soluble calcium $[Ca^{2+}]$ and phosphate $[PO_4^{3-}]$ ions, collagen and osteoinductive bone morphogenetic proteins (BMPs). The released molecular proteins (BMPs) sequentially result in increased cellular differentiation of active osteoblasts. Active osteoblasts deposit organic scaffolds, referred to as osteoid matrices. In the presence of soluble $[Ca^{2+}]$ and $[PO_4^{3-}]$ ions, osteoid matrices are gradually-converted into bone through the serial precipitation of calcium phosphate compositions. The first calcium phosphate phase to precipitate during natural bone formation is calcium hydrogen phosphate [$CaHPO_4$ (DICAL)] (Brown. P; Constantz, B. *Hydroxylapatite and Related Materials*. Boca Raton, Fla.; CRC Press, 1994, 9; Francis, M.; Webb, N. "Hydroxylapatite formation from a hydrated calcium monohydrogen phosphate precursors", *Calcif. Tissue Res.*, 6, pps. 335-342, 1971; Johnson, M. S.; Nacollas, G. H. "The role of brushite and octacalcium phosphate in apatite formation". *Critical Reviews in Oral Biology and Medicine*, 3 [1/2], pps. 61-82 (1992); Brown, W.; Chow, L. C. "Chemical Properties of bone mineral". *Ann. Res. Mater. Sci.*, 6, pps. 212-226, 1976; Brown, W.; "Crystal chemistry of Octacalcium Phosphate", *Prog. Cyrstal Growth Charact*, 4, pps. 59-87, 1981). The calcium hydrogen phosphate product is then quickly and sequentially transformed into biomedical calcium phosphate compositions, including tricalcium phosphate [$Ca_3(PO_4)_2$ (TCP)], octacalcium phosphate [$Ca_4(PO_4)_3(OH)(OCP)$] and hydroxylapatite [$Ca_5(PO_4)_3(OH)(HA)$]. FIG. 18 shows an overview of these processes.

In one embodiment, the present invention is directed toward a bone growth composition comprising a bone growth protein having a first bioactivity; and an acidic substrate; wherein the bone growth protein has a second bioactivity greater than the first bioactivity when combined with the acidic substrate. In this embodiment, the ability of the bone growth protein to induce bone growth is greater at an acidic pH than it is at a neutral and/or basic pH. The bone growth composition is particularly useful in processes of the present invention which include implanting the product in the body for the purpose of inducing bone formation in vivo. This embodiment provides an acidic substrate which can be substituted for demineralized bone matrix as a delivery vehicle that not only avoids the risks of disease/pathogen transmission associated with demineralized bone matrix use, but which also enhances the osteoinductive activity of bone growth proteins. Compositions of the present invention have been shown to improve both the quantity (e.g., mass) and quality (e.g., histological score) of bone produced with bone morphogenic protein at reduced doses.

It should be noted that while most contemplated applications of the present invention are concerned with use in humans, the products and processes of the present invention work in non-human animals as well. Induction of bone formation can be determined by a histological evaluation showing the de novo formation of bone with accompanying osteoblasts, osteoclasts, and osteoid matrix. For example, osteoinductive activity of a bone growth factor can be demonstrated by a test using a substrate onto which material to be tested is deposited. For example, osteoinductive activity can be graded or scored as disclosed in U.S. Pat. No. 5,290,763 or as is described below in the Examples.

The bone growth composition comprises an acidic substrate and includes a bone growth protein. In certain embodiments, the substrate can provide a structure for the growth of bone and an acidic environment to enhance the activity of the bone growth protein. In such embodiments, the bone growth protein can be highly active in the acidic environment of the composition and induces the production of bone.

The acidic substrate of the bone growth composition provides a structure for the various other components of the composition and also allows for the ingrowth of bone induced by the composition. More particularly, the substrate can be a matrix forming material, such as collagen, fibrin or alginate.

A preferred substrate is collagen and a preferred collagen is Type I bovine tendon atelocollagen or Type I bovine dermal atelocollagen.

The acidic substrate can also comprise a compound which renders the substrate acidic. In one embodiment, the acidic substrate comprises a calcium source and a phosphate source. In a preferred embodiment, the acidic substrate comprises an acidic calcium phosphate compound. The calcium and phosphate of the compound provide an available supply of these ions for the production of bone.

In embodiments wherein the composition includes sources of calcium and phosphate, these sources can be used to locally enhance the soluble concentration of dissolved calcium [$Ca^{2+}$] and phosphate [$PO_4^-$] within and around the site of implantation of the composition. Natural bone acts as a reservoir to, inter alia, maintain constant serum concentrations of these components. It has been theorized that the rate of bone formation may be limited by the diffusion of these critical ions to the site of bone induction. In brief, bone mineralization may exhaust the local serum concentration of calcium and phosphate, after which bone mineralization is limited by the rates of both osteoclast resorption of local bone (to provide soluble calcium and phosphate ions) and diffusion of these ions to the site of bone induction. By specifically enhancing the local concentration of these critical components, such as by the use of sparingly soluble calcium phosphate additives, the amount (mass) and quality of induced bone formation can be enhanced.

Preferred sources of calcium for the composition of the present invention include essentially any acidic calcium salt, including calcium phosphate or calcium citrate. Particularly preferred sources of calcium include acidic calcium phosphate salts. Preferred acidic calcium phosphate salts include monocalcium phosphate, calcium phosphate dihydrate (also known as dical), and calcium pyrophosphate. Typically, the calcium source is present in the composition in an amount of between about 1% by weight and about 85% by weight. In one embodiment, the calcium source is present from about 45 wt % to about 85 wt %. Ina further embodiment, the calcium source is present from about 50 wt % to about 80 wt %. In yet a further embodiment, the calcium source is present from about 55 wt % to about 75 wt %. In still a further embodiment, the calcium source is present from about 60 wt % to about 70 wt %.

Preferred sources of phosphate for the composition of the present invention include essentially any phosphate salt, including calcium phosphate or sodium phosphate. Particularly preferred sources of phosphate include calcium phosphate salts, and more particularly preferred sources of phosphate include acidic calcium phosphate salts. Preferred acidic calcium phosphate salts include calcium hydrogen phosphate dihydrate, monocalcium phosphate, calcium pyrophosphate, or a mixture of two or more thereof.

Typically, the phosphate source is present in the composition in an amount of between about 1% by weight and about 85% by weight. In one embodiment, the phosphate source is present from about 45 wt % to about 85 wt %. In a further embodiment, the phosphate source is present from about 50 wt % to about 80 wt %. In yet a further embodiment, the phosphate source is present from about 55 wt % to about 75 wt %. In still a further embodiment, the phosphate source is present from about 60 wt % to about 70 wt %.

The calcium source and the phosphate source can be the same material.

As noted above, preferred sources of calcium and of phosphate include acidic calcium phosphate salts. Calcium phosphates can be represented by the general chemical formula of $xCaO.P_2O_5$. The sparingly soluble calcium phosphate salts act as solution buffers. Thus, as the salts increase in calcia concentration (CaO), the pH increases from approximately 2 (x=1) to 11 (x=4). It is believed that the alkaline buffering nature of hydroxyapatite (x=3.33, about pH 9) reduces the performance of bone growth proteins. It has been found that acidic calcium phosphate salts (i.e., monocalcium phosphate $(Ca(H_2PO_4)_2)$, calcium hydrogen phosphate dihydrate $(CaHPO_4.2H_2O)$ and calcium pyrophosphate $(2CaO.P_2O_5))$ stimulate the osteoinductive performance of bone growth proteins. In comparison to collagen composites containing devitalized bone matrix additives, collagen dispersions containing calcium hydrogen phosphate $(CaHPO_4.2H_2O)$ have resulted in superior bone quality.

Alternatively, in one embodiment, the acidic calcium phosphate compound has a $Ca:PO_4$ ratio from about 0.5 to about 1. In another embodiment, the acidic calcium phosphate compound is a highly acidic calcium phosphate mineral, by which is meant an acidic calcium phosphate mineral having a $Ca:PO_4$ ratio from about 0.25 to about 0.5. In a further embodiment, the acidic calcium phosphate has a $Ca:PO_4$ ratio from about 0.3 to about 0.4. The acidic calcium phosphate compound tends to lower the pH of the composition, and in the absence of other compounds that are basic, the composition will have an acidic pH.

Thus, in preferred embodiments, the composition of the present invention uses calcium phosphate salts to (1) control local pH (to enhance/control bone growth factor release activity by providing protons to biological tissues within about 0.1 mm to about 5 cm of the site of implantation), (2) locally enhance soluble calcium concentration (which increases bone production within about 0.1 mm to about 5 cm of the site of implantation), and (3) locally enhance soluble phosphate concentration (which also increases bone production within about 0.1 mm to about 5 cm of the site of implantation). In comparison to collagen composites containing devitalized bone matrix additives, collagen dispersions containing acidic calcium phosphates have been developed that stimulate the formation of larger explants containing bone of superior quality. As noted above, control of each of the foregoing three factors independently can be used to enhance bone production by the bone growth composition. Accordingly, acidic mineral salts other than calcium phosphate salts can be used to control pH, thereby increasing the bone morphogenic activity of bone growth proteins without providing additional calcium or phosphate. Additionally, other buffering agents (e.g., a sulfate-based buffer) or acidifying agents (e.g., lactic acid) can be used to control the local pH surrounding the composition in the absence of a calcium source, in the absence of a phosphate source, or in the absence of a calcium phosphate source. Similarly, the use of specific calcium salts (e.g., calcium citrate) which do not incorporate phosphorus can be used without regard to control of local pH or phosphate concentration. Likewise, the use of non-calcium phosphate salts (i.e., sodium phosphate salts) can be used to enhance local concentrations of phosphate ions to enhance bone morphogenic activity without specifically controlling local pH or calcium concentration. Each of these three factors (the addition of a calcium source, the addition of a phosphate source, and the control of the local pH) leads to increased bone production or growth independently of one another (see, e.g., FIGS. 10 and 11). The bone growth and production enhanced by these three factors may be increased in quantity (e.g., as evidenced by increased relative mineral mass) or quality (e.g., as evidenced by increased relative histology score) or may be increased in both quantity and quality. Furthermore, the effects on bone growth enhanced by these three factors are separately additive. Thus, the combination of any two of the three factors in the final composition will increase the production of bone above the bone growth seen with anyone of the factors independently.

A further aspect of the composition of the present invention is the acidic buffering potential in physiological solutions. More particularly, when the composition of the present invention is put into a solution, such as a bodily fluid at physiological pH (e.g., in an in vivo application) or another weakly basic solution, the composition acts to buffer the solution at an acidic pH (i.e., the pH of the composition is less than 7). Additionally, if the composition is implanted into a mammal, the composition can buffer the environment within, on, or surrounding the implanted composition to an acidic pH. More particularly, the present compositions can buffer such solutions in the surrounding environment to a pH between about 2 and about 7, preferably between about 2 and about 5, more preferably between about 2 and about 4.9, such as about 2 and 4.9, and most preferably between about 3.5 and about 4.7. Control of the pH of the compositions can be achieved by those skilled in the art using routine techniques. For example, the use of buffering agents to maintain a desired pH range is well-known. Because compositions of the present invention can be used for in vivo applications, such buffering agents desire to be biocompatible. Particularly preferred buffers are discussed in more detail below.

The pKa of calcium monophosphate is known to be about 4.2, and thus its approximate buffering range is about pH 3.2 to 5.2. A composition composed of primarily calcium monophosphate is strongly acidic (e.g., pH<4). For reference, standard pKa values of various calcium phosphate salts are approximately as follows:

$Ca(H_2PO_4)_2$ (monocalcium phosphate; MCP) pKa=4.2
$CaHPO_4.2H_2O$ (dicalcium hydrogen phosphate; DCP) pKa=6.5
$3CaO.P_2O_5.2H_2O$ (tricalcium phosphate; TCP) pKa=26.0
$3.33CaO.P_2O_5.2H_2O$ (hydroxyapatite; HA) pKa=57.8
$4CaO.P_2O_5$ (tetracalcium phosphate; TTCP) pKa=30.6

In one embodiment of the composition, each calcium phosphate salt has a pKa from about 4 to about 6.5.

In one embodiment, the calcium phosphate is selected from sparingly soluble calcium phosphates that do not excessively bind to osteoinductive proteins. A mixture of such calcium phosphates can be used. Such a calcium phosphate provides a reserve of calcium and phosphate ions which can be slowly resorbed during the healing process and does not interfere significantly with the activity of osteoinductive proteins.

Biologically compatible, sparingly soluble calcium phosphates are suitable supplements to locally increase the supply of soluble calcium $[Ca^{2+}]$ and phosphate $[PO_4^{3-}]$ ions. As shown in Table 1, calcium phosphate salts solubilize at different equilibrium ionic concentrations. Despite the fact that the local supplemented concentrations of calcium $[Ca^{2+}]$ and phosphate $[PO_4^{3-}]$ ions can vary by more than four orders of magnitude, the limited solubility of calcium phosphates ensures that only a minor fraction of the mineral is solubilized. This allows the calcium phosphate to continue to supplement the soluble mineral pool during months of expected healing.

In summary, like TCP and HA, calcium hydrogen phosphate $[CaHPO_4$ (DICAL)$]$ provides local concentrations of $[Ca^{2+}]$ and $[PO_4^{3-}]$ for bone healing. At the same time, DICAL's resorption rate is essentially equivalent to conventional tricalcium phosphate and hydroxylapatite BVF supplements.

TABLE 1

Equilibrium solubility of calcium and phosphate ions from several different biologically compatible calcium phosphate salts

|  | Equilibrium [$Ca^{2+}$] | Equilibrium [$PO_4^{3-}$] | Insoluble fraction [200 mg/cc] |
|---|---|---|---|
| Plasma | 2,200.0 μM | 1,100.0 μM | — |
| $Ca(H_2PO_4)_2$ (Monocal) | 14,300.0 μM | 28,600.0 μM | 97.0000 wt. % |
| $CaHPO_4$ (DICAL) | 480.0 μM | 480.0 μM | 99.9700 wt. % |
| $Ca_3(PO_4)_2$ (TCP) | 1.4 μM | 0.9 μM | 99.9999 wt. % |
| $Ca_5(PO_4)_3(OH)$ (HA) | 2.2 μM | 1.3 μM | 99.9999 wt. % |
| $Ca_4(PO_4)_2(OH)_2$ (TTCP) | 28.2 μM | 14.1 μM | 99.9994 wt. % |

In one embodiment, the calcium phosphate can be any calcium phosphate which is more than 95 wt % insoluble when 200 mg of the calcium phosphate are introduced at room temperature to 1 cc of an aqueous solution at pH 7 prior to addition of the calcium phosphate. In a further embodiment, the calcium phosphate can be any calcium phosphate which is more than 99 wt % insoluble when 200 mg of the calcium phosphate are introduced at room temperature to 1 cc of an aqueous solution at pH 7 prior to addition of the calcium phosphate. In yet a further embodiment, the calcium phosphate can be any calcium phosphate which is more than 99.9 wt % insoluble when 200 mg of the calcium phosphate are introduced at room temperature to 1 cc of an aqueous solution at pH 7 prior to addition of the calcium phosphate. Any such calcium phosphate, however, must further not excessively bind osteoinductive proteins.

Various forms of calcium phosphates are known to have different chemical affinities for endogenous osteoinductive proteins (such as BMPs). A study was performed to assess the influence of variable composition calcium phosphate salts on the soluble concentration of osteoinductive proteins. This study measured the residual concentration of soluble recombinant BMP-2 after exposing a controlled concentration aliquot to an equimolar quantity of calcium phosphate salt. According to the results in Table 2, moderately acidic calcium phosphates salts, like DICAL, preserve greater than a 50 wt % soluble concentration of rhBMP-2, i.e., do not excessively bind to osteoinductive proteins. Though not to be bound by theory, we submit the enhanced local concentration and cellular availability of bone morphogenetic proteins (BMPs) would better stimulate bone formation.

TABLE 2

Equilibrium solubility of osteoinductive recombinant human BMP-2 protein in the presence of equimolar concentrations of various calcium phosphates.

|  | [rhBMP-2] mg/ml | [rhBMP-2] % |
|---|---|---|
| Control | 15.0 | 100% |
| $Ca(H_2PO_4)_2$ (MONO) | 15.0 | 100% |
| $CaHPO_4$ (DICAL) | 11.4 | 76% |
| $Ca_3(PO_4)_2$ (TCP) | 3.5 | 23% |
| $Ca_5(PO_4)_3(OH)$ (HA) | 2.3 | 15% |

As used herein, the term "osteoinductive material" refers to one or more proteins capable of inducing bone formation when implanted in a body. Suitable bone growth proteins of the present invention can be produced by purification of naturally occurring proteins (from xenograft, allograft, or autograft) or by recombinant DNA techniques. As used herein, the term recombinantly produced bone growth protein refers to the production of bone growth protein using recombinant DNA technology.

A number of naturally occurring proteins from bone or recombinant bone growth proteins have been described in the literature and tare suitable, Recombinantly produced bone growth proteins have been produced by several entities. Creative Biomolecules of Hopkinton, Mass., USA produces a bone growth protein referred to as Osteoinductive Protein 1 or OP 1. Genetics Institute of Cambridge, Mass., USA produces a series of bone growth proteins referred to as Bone Morphogenic Proteins 1-8 which are described in U.S. Pat. No. 5,106,748. Purified bone growth proteins have been developed by several entities. Collagen Corporation of Palo Alto, Calif., USA developed a purified protein mixture which is believed to have osteoinductive activity and which is described in U.S. Pat. Nos. 4,774,228; 4,774,322; 4,810,691; and 4,843,063. Marshall Urist of the University of California developed a purified protein mixture which is believed to be osteoinductive and which is described in U.S. Pat. Nos. 4,455,256; 4,619,989; 4,761,471; 4,789,732; and 4,795,804. International Genetic Engineering, Inc. of Santa Monica, Calif., USA developed a purified protein mixture which is believed to be osteoinductive and which is described in U.S. Pat. No. 4,804,744. All of the foregoing patents are incorporated herein by reference.

A preferred bone growth protein of the present invention and process for making the same is described in detail in U.S. Pat. No. 5,290,763, which is incorporated herein by reference. Protein mixtures prepared in accordance with the disclosure of U.S. Pat. No. 5,290,763 are referred to herein as "Bone Protein Mixture" or "BPM." This bone growth protein is preferred because of its high osteoinductive activity and because it is a purified bone growth protein. The Bone Protein of U.S. Pat. No. 5,290,763 exhibits osteoinductive activity at about 3 micrograms when deposited onto a suitable carrier and implanted subcutaneously.

Yet another embodiment of the preferred bone growth protein of the invention as described in U.S. Pat. No. 5,290,763 includes an osteoinductively active mixture of proteins having, upon hydrolysis, an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids. More particularly, the preferred bone growth protein has an amino acid composition of about 20.7 to about 26.1 (preferably about 23.4) mole percent of ASP (+ASN) and GLU (+GLN); about 11.3 to about 15.7 (preferably about 13.5) mole percent SER and THR; about 37.6 to about 42.4 (preferably about 40.0) mole percent ALA, GLY, PRO, VAL, MET, ILE, and LEU; about 5.8 to about 7.9 (preferably about 6.8) mole percent TYR and PHE; and about 13.3 to about 19.9 (preferably about 16.6) mole percent HIS, ARG, and LYS. A further embodiment of the preferred bone growth protein is a protein mixture having the approximate amino acid composition shown in Table 3.

TABLE 3

| Amino Acid | Mole Percent |
|---|---|
| Asp | 11.14 |
| Glu | 12.25 |
| Ser | 9.48 |

TABLE 3-continued

| Amino Acid | Mole Percent |
|---|---|
| Gly | 8.50 |
| His | 2.28 |
| Arg | 7.19 |
| Thr | 4.03 |
| Ala | 8.05 |
| Pro | 7.16 |
| Tyr | 3.63 |
| Val | 3.79 |
| Met | 1.73 |
| Ile | 2.75 |
| Leu | 8.00 |
| Phe | 3.21 |
| Lys | 7.11 |

In a further embodiment, the bone growth protein of the present invention is a "TGFβ superfamily protein" which can be any protein of the art-recognized superfamily of extracellular signal transduction proteins that are structurally related to TGFβ1-5. Preferably, a TGFβ superfamily protein suitable for use in the present invention is selected from the following proteins: TGFβ1, TGFβ2, TGFβ3, bone morphogenic protein (BMP)-2, BMP-3, BMP-4, BMP-5, BMP-6, BMP-7, BMP-8, BMP-9, cartilage-derived morphogenic protein (CDMP)-1, CDMP-2, and/or CDMP-3.

Other bone growth proteins that can be used in the bone growth protein mixture include fibroblast growth factor (FGF)-1, BMP-1, BMP-2α, BMP-2β, BMP-3b, BMP-8b, BMP-10, BMP-11, BMP-12, BMP-13, BMP-14, BMP-15, TGFβ4, TGFβ5.

The amount or dose of bone growth protein used depends on the activity of the bone growth protein and the particular application. In the case of the bone growth protein identified in U.S. Pat. No. 5,290,763, the bone growth protein is used in amounts between about 10 micrograms/gram substrate and about 10,000 micrograms/g substrate, more preferably between about 100 micrograms/g substrate and about 350 micrograms/g substrate, and more preferably between about 150 micrograms/g substrate and about 250 micrograms/g substrate.

In another embodiment, the bone growth composition can comprise between about 0.5 micromol of the acidic calcium phosphate compound per 1 microgram of total bone growth protein to about 6 micromol of the acidic calcium phosphate compound per 1 microgram of total bone growth protein.

It has been determined by the present inventor that solution pH plays a strong role in the osteoinductive performance of bone growth proteins, with acidic environments providing dramatically superior results. In other words, the bone growth protein has a second bioactivity in an acidic environment, such as that provided in its environment by the acidic substrate, greater than a first bioactivity in a neutral or basic environment.

In one embodiment, the composition includes:

about 3 parts by weight to about 10 parts by weight of a collagen:acidic calcium phosphate mineral material having an average particle size of about 125 microns to about 5000 microns, wherein the material comprises about 25 wt % to about 75 wt % of the acidic calcium phosphate mineral, the material has a porosity of about 85% to about 98%, and the collagen and the acidic calcium phosphate mineral are dehydrothermally crosslinked;

about 1 part by weight to about 20 parts by weight of collagen other than that crosslinked with the acidic calcium phosphate mineral material in the collagen:acidic calcium phosphate mineral material; and about 2 parts by weight to about 15 parts by weight of a highly acidic calcium phosphate mineral other than that crosslinked with collagen in the collagen:acidic calcium phosphate mineral material.

The collagen:acidic calcium phosphate mineral material can have from about 33 mg acidic calcium phosphate mineral per 100 mg collagen to about 300 mg acidic calcium phosphate mineral per 100 mg collagen.

In one embodiment, the acidic calcium phosphate mineral has a Ca:PO$_4$ ratio from about 0.5 to about 1, and the highly acidic calcium phosphate mineral has a Ca:PO$_4$ ratio from about 0.25 to about 0.5. The acidic calcium phosphate mineral can comprise one or more of calcium hydrogen phosphate dihydrate (CaHPO$_4$.2H$_2$O), monocalcium phosphate (Ca(H$_2$PO$_4$)$_2$), calcium pyrophosphate (2CaO.P$_2$O$_5$), tricalcium phosphate (3CaO.P$_2$O$_5$), hydroxyapatite (3.33CaO.P$_2$O$_5$(OH)$_2$), tetracalcium phosphate (4CaO.P$_2$O$_5$), or calcium carbonate (CaCO$_3$), and the highly acidic calcium phosphate mineral can comprise monocalcium phosphate. The pH of the composition can be tuned by the amount of the highly acidic calcium phosphate mineral used.

In further embodiments, the collagen:acidic calcium phosphate mineral material can have an average particle size of about 125 microns to about 300 microns, the material can comprise about 60 wt % to about 75 wt % of the acidic calcium phosphate mineral, and the material can have a porosity of about 94% to about 98%. In other words, the material can comprise about 150 mg acidic calcium phosphate mineral per 100 mg collagen to 300 mg acidic calcium phosphate mineral per 100 mg collagen.

In a further embodiment, the composition can comprise about 85 parts by volume to about 95 parts by volume of the collagen:acidic calcium phosphate mineral material and about 5 parts by volume to about 15 parts by volume collagen.

The composition can be further combined with a fluid, especially suitably for injection at a bone defect site. In one embodiment, the composition further comprises about 2 parts by weight to about 150 parts by weight of a fluid comprising water or an organic solvent. The fluid can include bone marrow aspirate, whole blood, plasma, platelet-rich plasma (PRP), serum, saline, water, PBS, cell culture media, or two or more thereof.

The composition can also further comprise one or more bone growth proteins as described above.

In another embodiment, the present invention relates to a method of forming a bone growth composition including combining a bone growth protein having a first bioactivity with an acidic substrate, wherein the bone growth protein has a second bioactivity when combined with the acidic substrate that is greater than the first bioactivity.

The composition of the present invention can be in a variety of different forms, such as a sponge, a paste, a fleece, or particles, among others, comprising natural materials such as collagen or chitin, among others, or synthetic materials such as PLA or PGA, among others. In a preferred embodiment, a collagen sponge is provided which contains bone growth proteins as well as calcium phosphate salts for controlling pH and providing calcium and phosphate to the local environment. An example of how to prepare such a sponge is provided below.

Another embodiment of the present invention is a novel process to produce collagen sponges for implantation which incorporate the replacement materials generally described above. In one embodiment, the products are prepared by producing a dispersion of collagen fibrils that contains either solubilized calcium salts or solubilized phosphate salts. Suitable collagen can include type I collagen, type II collagen, type III collagen, or type N collagen. In one embodiment, the collagen is from bovine tendon. The collagen dispersion is typically between about 0.5% by weight and about 20% by weight collagen, more preferably between about 1% by weight and about 10% by weight collagen, and most preferably between about 3% by weight and about 5% by weight collagen.

If the dispersion was made with a calcium salt, a phosphate salt is then added to the dispersion to heterogeneously precipitate a calcium phosphate salt directly onto the surface of the collagen fibrils. If the dispersion was made with a phosphate salt, a calcium salt is then added to the dispersion to heterogeneously precipitate a calcium phosphate salt directly onto the surface of the collagen fibrils. The interfacial adherence of the precipitate improves the mechanical rigidity and wetability of the composite sponges. The composition can be cross-linked. In one embodiment, the application of dehydrothermal collagen cross-linking techniques (e.g., 110° C., 24-72 hrs, vacuum) are well known in the art. Such cross-linking techniques result in the formation of water stable, collagen sponges of superior physical properties. Such sponges can then be loaded with bone growth protein and used for induction of bone growth in vivo. In a preferred embodiment, the products are prepared by producing a 4% (by weight) collagen dispersion that contains solubilized calcium dichloride dihydrate ($CaCl_2 \cdot 2H_2O$). A solution of disodium phosphate ($Na_2HPO_4$) is added to the heterogeneously precipitate calcium hydrogen phosphate dihydrate ($CaHPO_4 \cdot 2H_2O$) directly onto the surface of collagen fibrils.

In one embodiment, the composition can be formed starting with dicalcium hydrogen phosphate [$CaHPO_4 xH_2O$, (DI-CAL)] (Sigma, St. Louis, Mo.), monocalcium phosphate [$Ca(H_2PO_4)_2$ (MONOCAL)] (Sigma, St. Louis, Mo.), bovine dermal collagen, (Kensey Nash Corporation, Exton, Pa.), hydrochloric acid, and distilled, de-ionized water. After sterilization of the calcium phosphates and preparation of a 30 mM hydrochloric acid solution, a cross-linked, collagen-calcium phosphate sponge particle can be prepared.

First, a composite collagen-calcium phosphate gel dispersion (5 vol % collagen gel) can be prepared by introducing collagen and dicalcium hydrogen phosphate to one syringe, the 30 mM HCl solution to another, and mixing between the two. The dispersion can then be cast in a mold and frozen (−80° C. for at least 1 hr), followed by lyophilization/freeze-drying. The samples can then be dehydrothermally cross-linked in a vacuum oven (110° C., 48 hr) and thereafter milled and collected with −20 mesh (typically, about 0.5-1.2 micron).

Second, a high surface area (HSA), soluble collagen particle preparation can be prepared by dual-syringe mixing of collagen and sufficient 30 mM HCl to yield a 2 vol % solid dispersion. The dispersion can then be cast, frozen, and lyophilized/freeze-dried as described above. The samples can then be milled and collected with −60 mesh.

Third, the soluble HSA collagen particles (about 60 weight parts), collagen-DICAL DHT cross-linked particles (about 530 weight parts), and monocalcium phosphate powder (about 100 weight parts) can be combined to form a final dry powder.

The final dry powder can then be combined with various fluids to yield a putty or a paste, according to Table 4:

TABLE 4

| | Per 1 cc dry powder volume, mix the approximate volume of the specific fluids to obtain cohesive putties. |
|---|---|
| Putty consistency | |
| Saline | 0.4 ml |
| Phosphate buffered saline | 0.4 ml |
| Whole blood | 0.6 ml |
| Paste Consistency | |
| Saline | 1.0 ml |
| Phosphate buffered saline | 1.0 ml |
| Whole blood | 1.3 ml |

Alternative processes for producing the composition of the present invention are possible.

Another process of the present invention includes implanting a composition as broadly described above into a body for induction of bone growth. The composition can be combined with a fluid, which can include bone marrow aspirate, whole blood, plasma, platelet-rich plasma (PRP), serum, saline, water, PBS, cell culture media, or two or more thereof. As noted above, most uses of the present invention are concerned with human applications. The process, however, is suitable for a wide variety of animals, such as vertebrates, such as mammals, of which humans are one example. As used herein, the term implanting refers to placing the composition of the present invention in any bone defect or other area in which it is desired to have bone grow or survive. By implanting composition, bone formation is induced by the bone growth protein. Over time, preferred calcium and phosphate materials are resorbed allowing for uniform bone formation throughout a defect area.

In another embodiment, the present invention relates to a method of promoting bone growth at a bone defect in a mammal including combining a bone growth protein having a first bioactivity with an acidic substrate, wherein the bone growth protein has a second bioactivity greater than the first bioactivity when combined with the acidic substrate; and delivering the bone growth protein to the bone defect.

The combining and delivering steps can be performed sequentially or simultaneously. The delivering step can also be considered an implanting step.

Compositions of the present invention can be used in a variety of applications whenever there is a desire to generate bone, or retard bone loss. Such applications include induction of bone formation for hip replacement operations, knee replacement operations, spinal fusion procedures, repair of periodontal defects, treatment of osteoporosis, repair of bone tumor defects and repair of bone fractures and defects.

In the case of hip replacement operations, the ball and socket joint of a hip is replaced when a person's hip is not functioning properly. The ball portion of a joint is replaced by surgical removal of the ball portion from the terminus of the femur. The artificial ball portion has a functional ball end with the opposite end being a stem which is inserted into the proximal end of the femur from which the natural ball portion was removed. The stem can have a porous surface so that bone growth around the stem can anchor the stem in the femur. The product of the present invention, in particulate form, is layered, packed, or injected between the stem and the cavity in the femur in which stem is to be inserted. The socket portion of a joint is replaced by inserting an artificial socket into the natural socket. The artificial socket is sized to fit with the artificial ball. On the surface of the artificial socket which contacts the natural socket, the artificial socket can have a porous surface. The product of the present invention, in particulate form, is placed in the natural socket cavity so that upon placement of the artificial socket, the product is between the natural and artificial socket. In this manner, as bone is formed, the artificial socket is anchored in the natural socket.

Products of the present invention are also suitable for use in knee replacement operations. Knee prostheses have a femoral and a tibial component which are inserted into the distal end of the femur and the surgically prepared end of the tibia, respectively. The product of the present invention is layered, packed, or injected between the femoral and/or tibial components of the prosthesis and the respective portions of the femur and tibia. In this manner, as bone formation is induced between the prosthesis and the bones, the prosthesis becomes anchored.

Products of the present invention are also suitable for use in spinal fusion operations in which it is desired to substantially immobilize two vertebrae with respect to each other. The product can be applied, for example, between adjacent spinous and transverse processes so that upon bone formation throughout the composite material, two adjacent vertebrae are joined by fusion between the respective spinous processes and transverse processes.

In the case of periodontal defects, the product of the present invention is conformed to the defect shape. As bone growth is induced, bone fills in the defect.

In the treatment of osteoporosis, the present product is injected in existing bone to offset the effects of osteoporosis in which bone density is lost. For example, if it is determined that bone density is low in a localized area, such an injection can be made in that area.

In the treatment of bone fractures, traumatic osseous defects, or surgically-created osseous defects, the product of the present invention is layered, packed, or injected into the fracture or defect. In this manner, as bone formation is induced, the fracture or defect is treated.

In performing the method, it may be convenient to provide to the surgeon performing the delivering step to be provided with a precursor to the composition in kit form. Therefore, in another embodiment, the present invention relates to a kit for promoting bone growth at a bone defect in a mammal, comprising a bone growth protein having a first bioactivity and an acidic substrate, wherein the bone growth protein has a second bioactivity greater than the first bioactivity when combined with the acidic substrate.

The following examples are provided for the purposes of illustration and are not intended to limit the scope of the present invention.

EXAMPLES

Example 1

This example illustrates the production and use of bone growth protein containing devices that provide equivalent or superior osteoinductive performance without the addition of demineralized bone matrix additives as biologic supplements.

This example shows the influence of the carrier vehicle on the in vitro and in vivo osteoinductivity attributable to osteoinductive growth factors. An accepted protocol to assess the osteoinductive activity of composite materials is through implantation of samples in rats. The advantages of the rat model for product evaluation include its moderate cost and an accelerated rate of bone induction. Visible evidence of mineralization appears in the implant within several days (~10), with typical experiments lasting between 14 and 21 days. Osteoinductive activity is commonly evaluated using four standard test protocols: histological tissue analysis, mineral concentration via x-ray and ash weight evaluation and bone cell activity via alkaline phosphatase analysis.

This example specifically compared the osteoinductive differences between implant samples containing Bone Protein Mixture (BPM), collagen (bovine tendon type 1) and a powder of either devitalized bone matrix (DVBM) or the calcium phosphate ceramic (Ostite) [Millennium Biologix, Kingston, Canada]. Ostite is a material containing variable concentrations of calcium hydroxyapatite and silica stabilized tricalcium phosphate. Similarly to alternative calcium phosphate sources, Ostite supports the required interfacial activity of osteoblasts for bone regeneration. A unique feature of Ostite is that it has been shown to degrade only by osteoclastic resorption. Sample disks were prepared with variable composition: a) collagen (100 wt. %)/BPM and b) collagen/particle (50/50 wt. %)/BPM. The sample disks were prepared using two distinct processing techniques. In the first technique, the components were mixed in phosphate buffered saline (PBS) at a collagen ratio of 4 wt. %. The mixtures were molded into disks (h~3 mm, d~8 mm) and freeze dried. In the second technique, the components were mixed with dilute acetic acid (1 vol. %) to form a gel with a collagen ratio of 4 wt. %. The gels were molded into disks and freeze-dried. All disks were loaded with BPM and freeze dried according to standard protocols.

The testing protocol involved sample implantation in subcutaneous (to assess endochondral bone formation) and calvaria sites (to assess membranous bone formation). The osteoinductive responses were evaluated after 4 weeks implantation using accepted protocols for explant mass, ash weight, x-ray mineral density and histology.

Clinically, the application of bone morphogenic proteins (BMPs) and other osteoinductive growths factors are desired to assist in the surgical reconstruction of skeletal defects. BMPs are advantageous because they induce bone formation by targeting and activating undifferentiated perivascular connective tissue cells. In contrast, mitogens target and accelerate the osteoinductive activity of previously differentiated cells. Numerous advances have improved the activity of osteoinductive factors, however, their clinical application has been limited by the requirement for a superior delivery vehicle.

Procedures:
Collagen Implants:

Collagen sponge disks were prepared according to standard procedures as follows; Mix 12.0 g of 1 vol. % glacial acidic acid and 500 mg of Bovine tendon Type 1 Collagen in an inert screw cap container. Mix with a spatula as the gel begins to form, minimizing the number of trapped air bubbles. Stop mixing when the gel becomes thick. Tap gel container on bench-top to remove trapped air bubbles and cap tightly. Allow mixture to sit for at least 1 hour at room temperature.

To make disks from the collagen dispersion, place a Delrin disk mold sheet on a glass plate and press the dispersion into the holes. Remove excess dispersion with a knife or spatula. Place the molding sheet and glass plate in a freezer at −80° C. for approximately 1 hour. Remove from the freezer and allow warming for approximately 1 minute. Remove the glass plate and place the Delrin plate into a freeze drying flask. Freeze dry for a minimum of 42 hours. After drying, remove the samples from the plate, trim the edges and weigh each disk. Each disk must weigh between 6.5 to 7.3 mg to be acceptable for use.

Collagen/Powder Implants:

In an inert screw cap container, mix 600 mg of Bovine tendon Type 1 collagen with 600 mg of either Ostite powder (NP) or devitalized rat bone matrix powder (DVM). Add 14.4 g of acetic acid (1 vol. %) to prepare gel dispersions containing 4 wt. % collagen. Stir with a spatula to homogenize the mixtures and to adequately wet the components. Vibrate the mixtures on a high intensity orbital shaker to remove trapped air bubbles. Allow mixtures to sit for at least 1 hour at room temperature.

To make disks from the collagen dispersions, place a Delrin disk mold sheet on a glass plate and press the mixtures into the holes. Remove excess mixture with a knife or spatula. Place the molding sheet and glass plate in a freezer at −80° C. for approximately 1 hour. Remove from the freezer and allow warming for approximately 1 minute. Remove the glass plate and place the Delrin plate into, a freeze-drying flask. Freeze dry for a minimum of 12 hours. After drying, remove the samples from the plate, trim the edges and weigh each disk. The disks must weigh between 13.0-14.6 mg to be acceptable for use.

BPM Loading:

Dilute a volume of BPM (produced as described in U.S. Pat. No. 5,290,763) with a volume of 10 mM HCl to prepare solutions of 10 mg BPM/100 ml (15 ml) and 35 mg BPM/100 ml (4.0 ml). In the Delrin loading plate, pipet 50 µl of a solution on each of the top and bottom half of a collagen sponge (n=240 (10 mg), n=48 (35 mg)). Allow disks to stand in a chamber containing a moist paper towel (to prevent drying and sponge shrinkage) at ambient temperatures for 40-60 minutes. Cover the disk holding plate with Saran Wrap and place in a −80° C. freezer for 40-60 min. Unwrap and carefully place in a freeze dryer flask. Freeze dry for a minimum of 12 hours then remove. The implant samples will respectively contain total BPM doses of 10 ng and 35 ng.

Surgical controls were used to determine the osteoinductive response in the calvaria implants due to irritation of the periosteum. A solution of 10 mM HCl was prepared and sterilized by filtration through a 0.2 mm sterile syringe filter. The solution was applied, to the collagen disks in an identical manner as the BPM loaded samples and served as negative controls.

Sample Disk Implantation

The weight of each Long-Evans rat was recorded. Acceptable rats for bioassays weigh between 100 and 130 g. The animals was anesthetized with 400 µl of pentobarbital dosing solution injected i.p.

Subcutaneous sample implantation was made as follows: small (6 mm) incisions were made in the skin of the ventral or dorsal thorax. Ventral incisions were made at the base of the rib cage. A template, to be aligned with the base of the rib cage, was provided to identify constant dorsal implant locations. After incision, a pocket beneath the skin and above the incision was prepared by blunt dissection. The loaded collagen sponges were placed in the pocket, approximately 5 mm above the incision. Additional incisions and implant insertions were made and then the incisions were closed with Tedvek II 5-0 (or equivalent) sutures.

The animals were housed in compliance with the guidelines described, in QC-008. The animals were checked for lesions 3-5 days post implantation. If lesions were detected or if animal death occurred before sacrifice, these results were documented.

Implantation Protocol and Analysis

The testing protocol involved subcutaneous implantation of collagen sponges (to assess endochondral bone formation) containing 10 µg BPM. The samples were placed in four subcutaneous implantation sites: the upper quadrants of a rat's abdomen and dorsal thorax [FIG. 1]. In addition, the testing protocol involved calvaria implantation of collagen sponges (to assess membranous bone formation) containing either 0 µg or 35 µg BPM. Samples of variable composition and concentration can be produced.

The osteoinductive activity of the implant is evaluated using accepted protocols for explant mass, ash weight, x-ray mineral density and histology. A total of 20 rats/composition were used. This population provided location-specific testing numbers of n=10/test for the subcutaneous assays. Normalizing the samples according to location-specific values provides a total subcutaneous sample population of n=40/test.

Three weeks post implantation, the animals (n=20) were sacrificed through $CO_2$ asphyxiation. The weight of the host rat and each implant is immediately measured post-surgical excision. The explants are imaged with x-ray radiation to determine mineral density as a function of composition and implant location. Forty percent of the subcutaneous samples were analyzed using accepted protocols for ash weight.

The remaining subcutaneous explants were analyzed for differences in tissue quality using accepted histology protocols. The averaged results and their standard deviations were analyzed for statistical significance using ANOVA comparisons. The results are shown in FIGS. 2-5.

Example 2

This example illustrates the independent effects of a calcium source and a phosphate source in the present invention.

Figure 10:
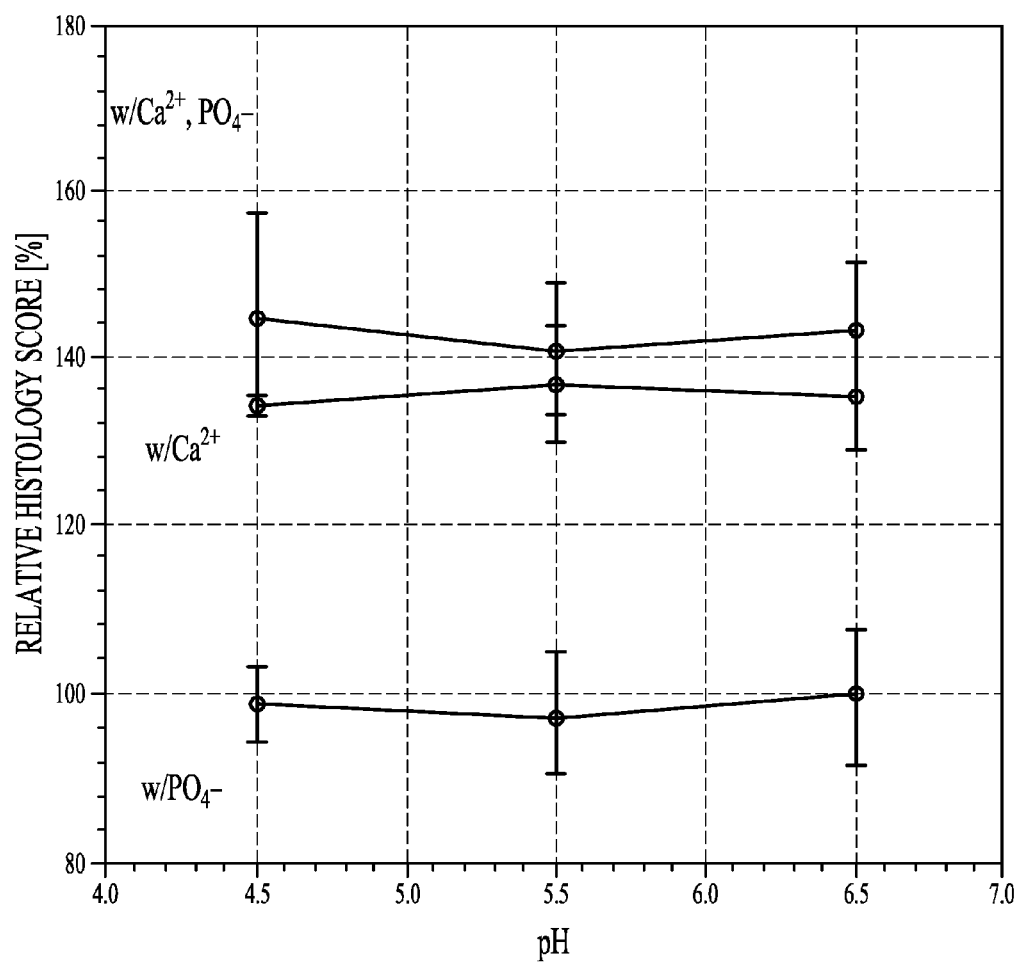
FIG. 10: shows the influence of adding a calcium source, a phosphate source, or both a calcium and a phosphate source to the implanted composition at different acidic buffering capacity on the histology score.
Figure 11:
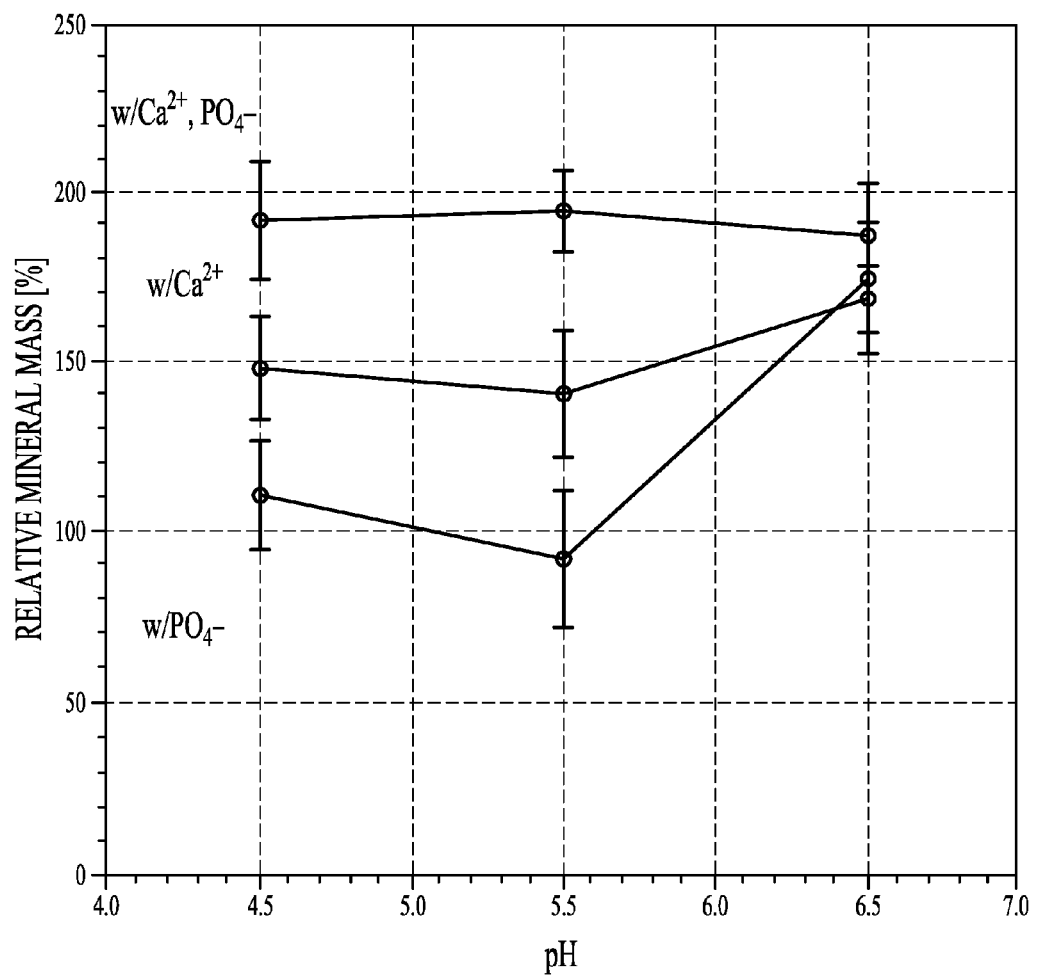
FIG. 11: shows the influence of adding a calcium source, a phosphate source, or both a calcium and a phosphate source to the implanted composition at different acidic buffering capacity on the relative mineral mass.

In vivo rat implantation assays were conducted to determine the effects of local supplementation of calcium, phosphate, and of both calcium and phosphate in the implanted compositions of the present invention. The implants containing a calcium source, a phosphate source or a source of both calcium and phosphate were tested and evaluated in terms of relative histology score and relative mineral mass gain. The results of these assays are shown in FIGS. 10 and 11.

Example 3

The effect of calcium phosphate chemical composition and microstructure (crystal structure) variations on the performance of osteoinductive proteins was evaluated using a subcutaneous rat implant model (Grossblatt, *Guide for the Care and Use of Laboratory Animals*. Washington D.C.: National Academy Press; 1996, 1-80; Intermedics Orthopedics/Denver, Inc. Rat Subcutaneous Bioassay: Bone Protein Assay STM-011). The advantages of the rat model for product evaluation include an accelerated rate of bone induction. Visible evidence of mineralization appears in the implant within several days (~10), with typical experiments lasting between 14 and 21 days. The testing protocol involved implantation of porous collagen (bovine tendon Type 1, 7 mg, 96 vol. % porosity) samples containing a natural mixture of bovine, osteoinductive proteins (GFm, 10 µg). A full range of calcium phosphates was evaluated, including: monocalcium phosphate [$Ca(H_2PO_4)_2$], calcium hydrogen phosphate dihydrate [$CaHPO_4.2H_2O$], calcium pyrophosphate [$2CaO.P_2O_5$], tricalcium phosphate [$\alpha$-$3CaO.P_2O_5$, $\beta$-$3CaO.P_2O_5$], hydroxyapatite [$3.33CaO.P_2O_5(OH)_2$ (polycrystalline and two amorphous compositions)], tetracalcium phosphate [$4CaO.P_2O_5$] or calcium carbonate [$CaCO_3$ (aragonite), $CaCO_3$ (calcite)]. Samples were implanted in four subcutaneous sites including the upper quadrants of the abdomen (sites 1, 2) and the upper quadrants of the dorsal thorax (sites 6, 7). The osteoinductive differences between controls and calcium phosphate supplemented samples [7 mg, 50 wt. %] were assessed using three standard test protocols: histological tissue analysis and mineral composition via x-ray and ash weight analysis (Intermedics Orthopedics/Denver, Inc. Histology protocol STM 009; Intermedics Orthopedics/Denver, Inc. Alkaline phophatase protocol STM 0024, 0026).

Samples were assessed in comparison to two different control sample populations, including: collagen sponges and collagen/GFm sponges supplemented with 50 wt % devitalized bone matrix (DVBM) additives. The collagen/GFm control samples were used as a reference for a baseline osteoinductive response. A calcium phosphate additive was considered detrimental if it either reduced the explant or mineral mass values or if it negatively influenced bone maturation. The composite collagen products containing devitalized bone matrix additives serve as a reference for a strongly positive osteoinductive response. These samples were prepared as an alternative for demineralized bone matrix (DBM) additives. Demineralized bone matrix provides both an ideal osteoconductive matrix for cellular invasion and bone mineralization and a pooled concentration of osteoinductive proteins. Unfortunately, the osteoinductive performance of DBM varies significantly. The composite products containing DVBM provide ideal osteoconductive benefits and controlled, uniform osteoinductive protein concentrations.

The experimental data are presented in box-whisker plot format for exploratory, nonparametric data analysis. These graphs are excellent for conveying variation information in data sets and illustrating variability between different groups of data. This information is represented within the three characteristic features of a box-whisker plots: 1) the box, 2) the horizontal line within the box and 3) the vertical lines (whiskers) that extend above and below the box.

The box encompasses the middle 50% of the data with the length of the box measuring data spread. The middle of the box represents the median or 'middle' value of the data set. The top of the box represents the $75^{th}$ percentile, meaning that 75% of the data values fall below this value. It is mathematically equivalent to the median data value plus 0.6745 of the standard deviation. The bottom of the box represents the $25^{th}$ percentile (median minus 0.6745 of the standard deviation), indicating the value which 75% of the data set exceeds. The horizontal line within the box represents the mean or average value of the data set.

The vertical lines that extend above and below the box indicate the maximum ($90^{th}$ percentile) and minimum ($10^{th}$ percentile) data values, respectively. The maximum and minimum points represent the last data values within 2.7 standard deviations of the median value. The location and length of these lines represents the distribution of data. If the mean value is found close to the center of the box and the length of the vertical lines are equivalent, it can be assumed that the data follows a normal Gaussian distribution. The data set is considered skewed if either the mean value is not centered within the box or the length of the maximum or minimum lines are unequal.

In a normal Gaussian distribution of data, outliers are defined as data values that differ from the median by more than three standard deviations. Outliers complicate statistical interpretations of data set differences because their magnitude can significantly influence the calculated mean and standard deviation. In contrast, outliers have a minimal influence on the median and quartile values used in box-whisker plots. This simplifies the identification of outliers, as identified by circles, and significantly improves statistical interpretations of data set differences.

The averaged results and their standard deviations were analyzed for statistical significance using ANOVA comparisons. ANOVA was performed without data replications turning the analysis into an expanded pool Student-T test. Statistical significance was predicted using $\alpha < 0.05$. Calcium phosphate compositions that had a statistically significant, negative effect on mass are italicized in the tabulated data. Compositions that had no significant influence on mass are indicated in plain text. Compositions that stimulated a statistically significant improvement in mass are indicated in bold text [Tables 5 and 6].

Figure 12A:
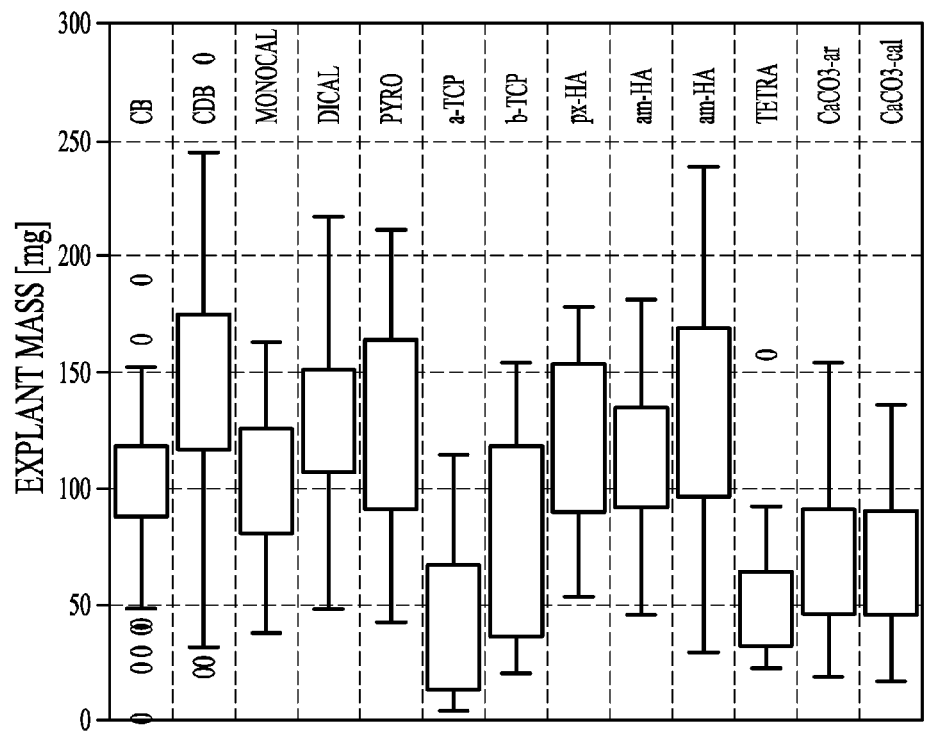
FIG. 12: Box plot representations of average (inter-animal) and relative (intra-animal) explant mass when supplemented with various calcium phosphates.
Figure 12B:
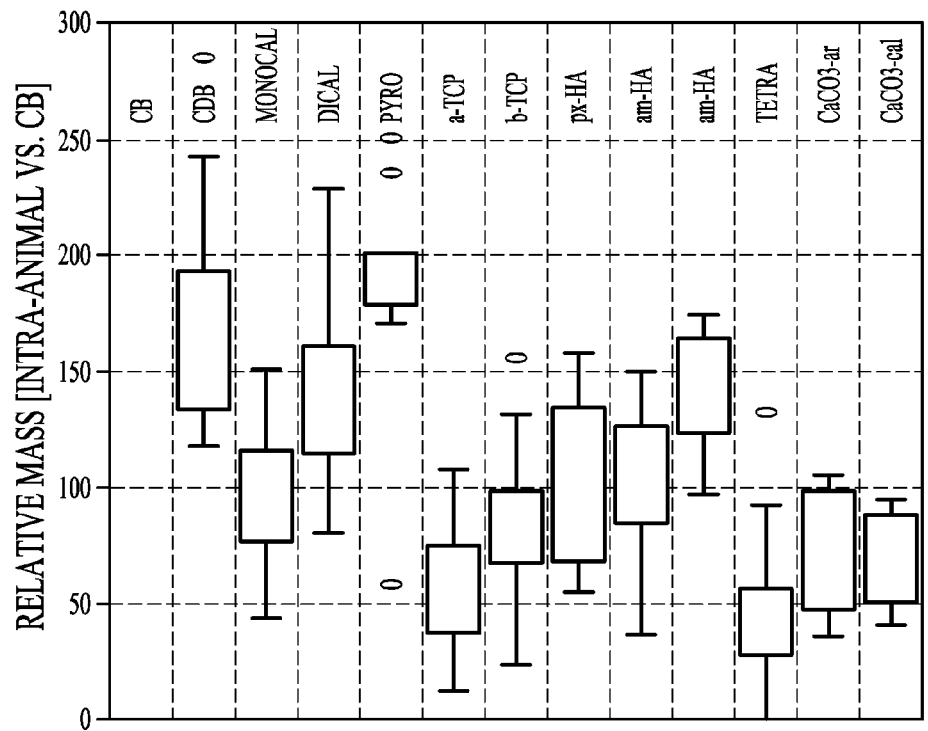
Figure 13A:
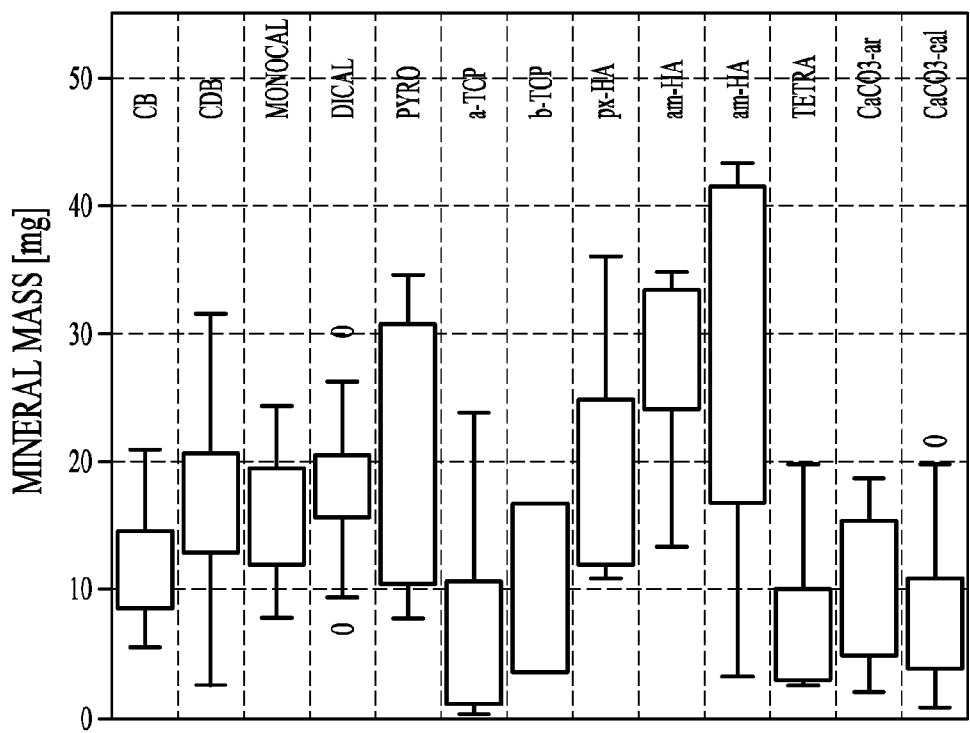
FIG. 13: Box plot representations of average (inter-animal) and relative (intra-animal) mineral mass when supplemented with various calcium phosphates.
Figure 13B:
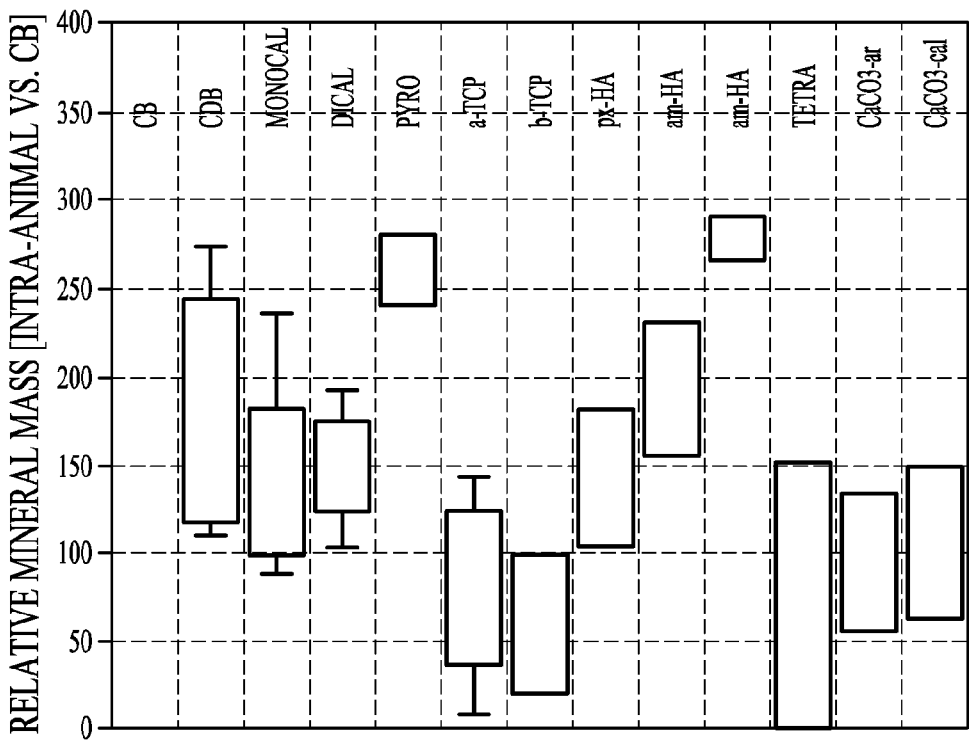

In comparison to the collagen controls (102.8±22.9 mg explant/11.7±3.6 mg mineral), the majority of the salts had a negligible or a detrimental effect on total explant and mineral mass [FIGS. 12, 13]. However, a bimodal increase in explant and mineral mass values was observed with moderately acidic calcium phosphate salts [$CaHPO_4.2H_2O$ (+40.2 wt. % mass/+153.6 wt. % mineral), $2CaO.P_2O_5$ (+99.6 wt. % mass, +263 wt. % mineral)] and moderately alkaline, amorphous hydroxyapatite [$3.33CaO.P_2O_5(OH)_2$ (Calcitek) (+44.1 wt. % explant mass, +279.6 wt. % mineral)].

The quality and skeletal maturity of produced bone was assessed through histological microscopic analysis of thin, stained tissue sections. The subcutaneous explants were removed, fixed in formalin and histologically processed with glycol methacrylate according to standard protocols (Dickson, Glenn R.: *Methods of Calcified Tissue Preparation*. Elsevier, 1984). Thin sections (4 µm) from the explant midlines were obtained with a microtome. One section was stained with hematoxylin & eosin (H&E) and one was stained with toluidine blue to highlight important cellular details. The H&E sections were counterstained with silver nitrate (Von Kossa technique) to highlight mineralized tissue components. The histological sections were scored for quality and maturity using a scoring system, outlined in Table 7, previously developed by Sulzer Biologics according to STM-021.

Figure 14A:
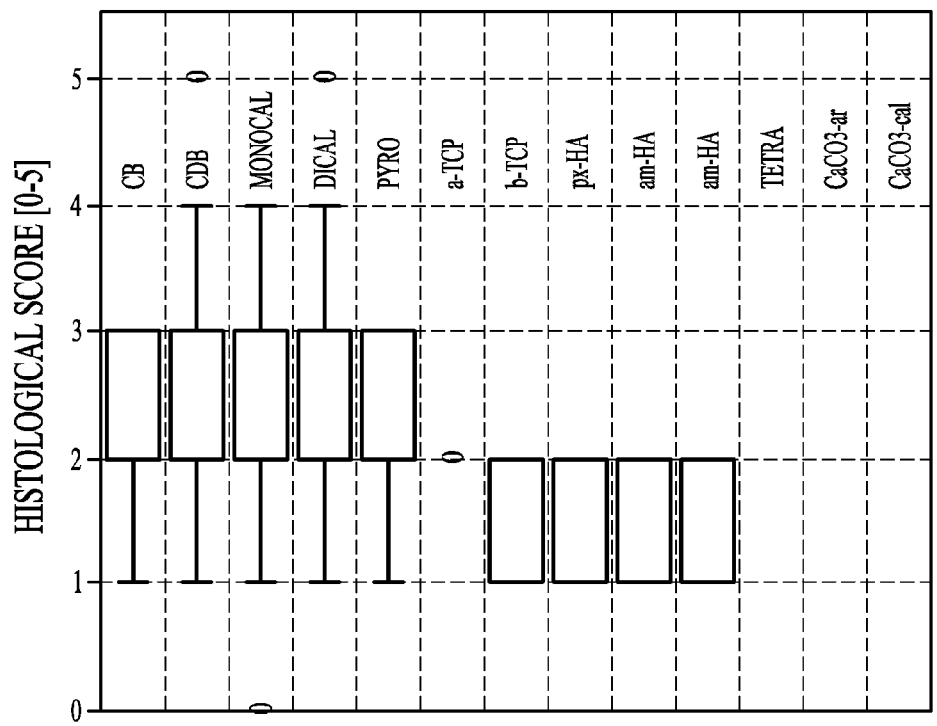
FIG. 14: Box plot representations of average (inter-animal) and relative (intra-animal) histological scores when supplemented with various calcium phosphates.
Figure 14B:
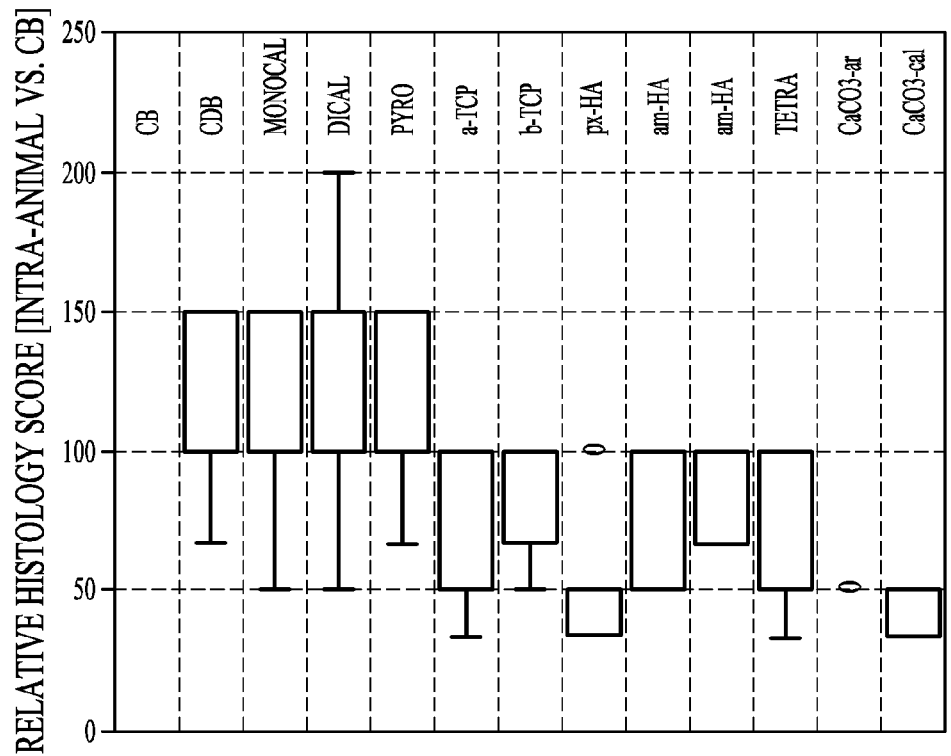

Using the described protocols, the influence of the various additives on histological quality was determined. The average histology score and the inter-animal standard deviation values are tabulated in the first two columns of Table 8. The relative differences in histology score, observed between experimental and control samples within a single rat (intra-animal difference), are included in the last four columns of Table 8. The magnitude and range of total and relative histological scores is graphically represented in the box plots of FIG. 14.

TABLE 5

Average (inter-animal) and relative (intra-animal) explant mass for implants supplemented with various calcium phosphates.

| | Average Explant Mass | | | Direct Comparison Averages | | | | |
|---|---|---|---|---|---|---|---|---|
| | [mg] | ±SD | N | [mg] | ±SD | Δwt. % | ±SD | N |
| Control | 102.8 | 22.9 | 235 | | | | | |
| DVBM | 142.8 | 46.0 | 290 | 178.9 | 27.8 | +66.8% | 39.4% | 40 |
| Ca(H$_2$PO$_4$)$_2$ (MCP) | 104.4 | 29.2 | 90 | 95.3 | 31.6 | −6.4% | 26.2% | 30 |
| CaHPO4•2H$_2$O (DCP) | 130.7 | 34.2 | 185 | 129.8 | 29.2 | +40.2% | 32.9% | 40 |
| 2CaO•P$_2$O$_5$•2H$_2$O (CP) | 126.2 | 49.5 | 25 | 170.3 | 43.7 | +99.6% | 27.1% | 10 |
| 3CaO•P$_2$O$_5$ (α-TCP) | 39.5 | 31.9 | 35 | 58.7 | 28.3 | −42.9% | 26.4% | 20 |
| 3CaO•P$_2$O$_5$ (β-TCP) | 80.1 | 43.4 | 45 | 71.6 | 40 | −26.3% | 33.6% | 20 |
| 3.33CaO•P$_2$O$_5$ (HA-px) | 113.5 | 32.2 | 20 | 124.7 | 43.1 | +4.5% | 37.2% | 10 |
| 3.33CaO•P$_2$O$_5$ (HA-am) | 129.5 | 60.3 | 30 | 120.3 | 32.2 | +0.3% | 29.6% | 15 |
| 3.33CaO•P$_2$O$_5$ (HA-am) | 117.9 | 36.3 | 30 | 140.6 | 30.2 | +44.1% | 25.0% | 10 |
| 4CaO•P$_2$O$_5$ (TTCP) | 54.8 | 30.9 | 20 | 70.0 | 38.3 | −46.2% | 39.2% | 10 |
| CaCO$_3$ (aragonite) | 69.4 | 30.7 | 40 | 88.6 | 32.6 | −27.3% | 26.0% | 10 |
| CaCO$_3$ (calcite) | 67.4 | 27.9 | 40 | 73.1 | 24.0 | −28.0% | 20.2% | 10 |

TABLE 6

Average (inter-animal) and relative (intra-animal) mineral mass for implants supplemented with various calcium phosphates.

| | Average Mineral Mass | | | Direct Comparison Average | | | | |
|---|---|---|---|---|---|---|---|---|
| | [mg] | ±SD | N | [mg] | ±SD | Δwt. % | ±SD | N |
| Control | 11.7 | 3.6 | 74 | | | | | |
| DVBM | 16.4 | 5.4 | 115 | 16.9 | 4.5 | +50.4% | 20.2% | 8 |
| Ca(H$_2$PO$_4$)$_2$ (MCP) | 16.0 | 4.6 | 26 | 14.2 | 6.0 | +50.2% | 27.5% | 8 |
| CaHPO4•2H$_2$O (DCP) | 18.0 | 4.5 | 73 | 16.4 | 3.2 | +53.6% | 28.3% | 16 |
| 2CaO•P$_2$O$_5$•2H$_2$O (CP) | 20.8 | 10.0 | 10 | 31.5 | 2.4 | +163.0% | 29.5% | 4 |
| 3CaO•P$_2$O$_5$ (α-TCP) | 6.5 | 7.7 | 12 | 9.4 | 8.1 | −28.3% | 28.6% | 8 |
| 3CaO•P$_2$O$_5$ (β-TCP) | 8.1 | 6.1 | 4 | 5.7 | 2.0 | −31.6% | 11.1% | 4 |
| 3.33CaO•P$_2$O$_5$ (HA-px) | 19.8 | 8.2 | 8 | 21.9 | 10.1 | +74.3% | 25.3% | 4 |
| 3.33CaO•P$_2$O$_5$ (HA-am) | 26.5 | 6.7 | 12 | 27.1 | 2.0 | +95.6% | 21.9% | 4 |
| 3.33CaO•P$_2$O$_5$ (HA-am) | 29.4 | 12.1 | 12 | 30.4 | 5.8 | +179.6% | 12.7% | 3 |
| 4CaO•P$_2$O$_5$ (Tetra) | 7.7 | 6.1 | 7 | 10.3 | 8.8 | −43.5% | 28.3% | 4 |
| CaCO$_3$ (aragonite) | 10.4 | 5.4 | 28 | 14.5 | 4.2 | +3.8% | 26.7% | 4 |
| CaCO$_3$ (calcite) | 7.9 | 5.2 | 27 | 8.1 | 3.0 | −3.2% | 28.5% | 4 |

The collagen control samples produced explants with an average histology score of approximately 2.2 (±0.6). The majority of samples resulted in histology scores of 2.0 or 3.0 with a small fraction obtaining scores of 1.0. The collagen control samples with DVBM produced explants with an average histology score of 2.8 (±0.8). The majority of samples resulted in histology scores of 2.0 or 3.0 with a small fraction obtaining scores of 1.0 and 4.0.

According to statistical analysis (Student T-test), the addition of DVBM significantly enhances osteoinductive performance ($\alpha$<0.05). The magnitude of the osteoinductive enhancement is represented in the lower box plot of FIG. 15. This plot includes intra-animal, relative histological score comparisons between the collagen and collagen DVBM controls. The intra-animal comparison indicates that the DVBM additives enhance histological scores by an average of +33.3% wt. % (±19.8 wt. %) with the majority of the improvements ranging between +0% and +50%.

In contrast to the previous results, only acidic calcium phosphate additives produced explants with histological scores equivalent and superior to that observed with the addition of DVBM. Statistically superior improvements in histological score were observed with monocalcium phosphate [Ca(H$_2$PO$_4$)$_2$, Monocal] (+9.9 wt. %), calcium hydrogen phosphate dihydrate [CaHPO$_4$.2H$_2$O, DICAL] (+53.6 wt. %) and calcium pyrophosphate [2CaO.P$_2$O$_5$, Pyro] (+163 wt. %) additives. Statistically significant reductions were observed in histological score for all other salt compositions.

The experimental data indicates that osteoinductive performance is hindered with calcium phosphate salts of high (>2 Ca/P) calcia CaO) content. In addition, the Ca/P ratio in the calcium phosphate salt directly correlates with its pH buffering potential, with high ratios being strongly alkaline. Monocalcium phosphate [Ca(H$_2$PO$_4$)$_2$] is highly acidic (pH~2). Dicalcium hydrogen phosphate and calcium pyrophosphate are moderately acidic (pH~5.5). The neutral transition point (pH~7) is located with tricalcium phosphate compositions. Hydroxyapatites are moderately alkaline (pH~8). Tetracalcium phosphate and calcium carbonates are highly alkaline (pH~10-11). This information indicates that osteoinductive performance is hindered with neutral and alkaline pH buffering additives or calcium phosphate salts having a high calcium content.

Figure 15:
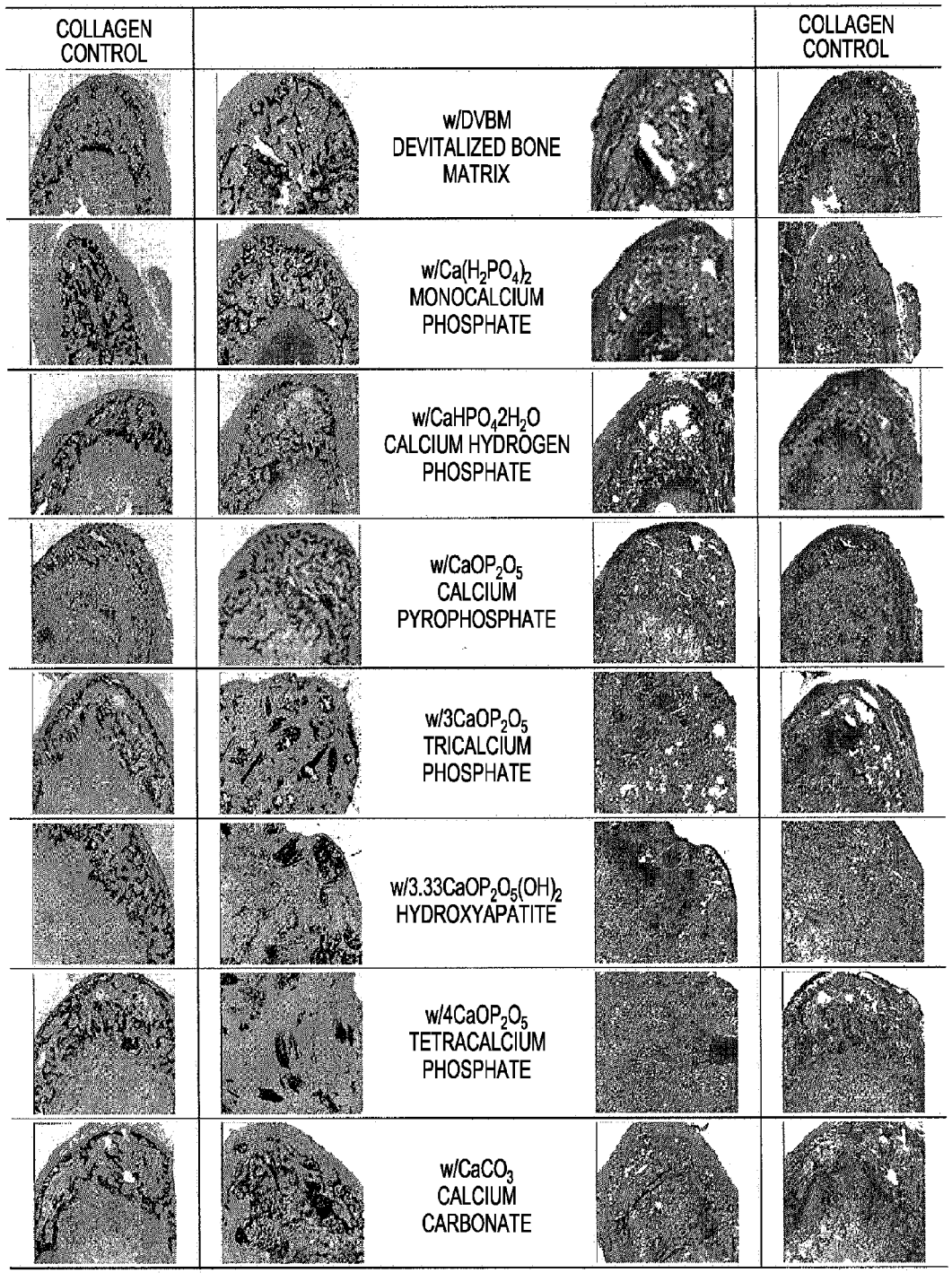
FIG. 15. Photomicrographs representing Average Histological differences between samples containing various calcium phosphate additives (7 mg, 50 wt. %) [2× magnification, processed with H&E/Von Kossa (left) and toluidine blue tissue stains (right)]

The effect of pH on bone quality and maturity is clearly demonstrated in the photomicrographs included in FIG. 15. The photomicrographs show the bone pattern on the periphery of the explanted material (2× magnification). Histological sections were selected from samples that matched both the average mass and the average histology score for each test group. The sample and its intra-animal collagen control are presented side-by-side.

In the Hematoxylin and eosin stained samples (FIG. 15, left), practically all cytoplasmic structures and intercellular substances are stained various shades of pink. The addition of silver nitrate (Von Kossa technique) stains all mineral black, making it simple to detect mineralized tissue. Although this simplifies assessments of mineralization patterns, it does not aid in distinguishing between new bone, mineralized cartilage, residual calcium phosphate additives and calcified carrier. Induced bone is distinguished from other mineralized tissues only by the combined presence of osteoid matrix seams (bright pink) and layered osteoblasts. Mature bone is represented by a continuous and thick cortical rim, lined with a continuous seam of osteoid matrix and active osteoblasts. Marrow quality is also easily assessed with this staining technique since the nuclear structures are stained dark purple or blue. Mature marrow is represented by samples that contain high concentrations of hemopoietic granulocytes (stained dark blue) and fat cells (adipocytes). The location and concentration of fat cells is represented by solubilized white voids.

The toluidine blue tissue stained samples were used to identify cartilage tissue. Cartilage tissue is stained light to deep purple, depending on the local concentration of proteoglycans. Mature cartilage contains a high concentration of proteoglycans. This stain is also useful for visualizing the number and activity of osteoblasts (Ob) and osteocytes (Oc) which are stained dark blue. Bone (B) appears lavender.

It is clearly observed that the acidic calcium phosphates universally stimulated the amount of bone formation (section diameter) and the depth of bone mineralization (bone staining content). Collagen samples supplemented with calcium hydrogen phosphate dihydrate [$CaHPO_4.2H_2O$] matched the cortical rim bone quality observed in collagen/DVBM controls. The perimeters for samples containing monocalcium phosphate and calcium pyrophosphate were comparatively reduced in maturity but were greater than control samples. Improvements in marrow quality were realized with each acidic calcium phosphate additive, with the samples supplemented with calcium hydrogen phosphate being the most mature. These samples contained high density concentrations of hemopoeitic granulocytes, red blood cell sinuses, and small adipocyte concentrations characteristic of mature bone.

Despite the increase in mass values, a negative effect on bone ossicle maturation, characterized by reduced cellular activity and dystrophic mineralization, was observed with hydroxyapatite and other alkaline calcium phosphate salts. In contrast, the samples supplemented with moderately acidic calcium phosphate salts enhanced bone maturation as well as the positive influences noted above. In fact, the histological qualities for samples containing calcium hydrogen phosphate dihydrate [$CaHPO_4.2H_2O$] additives were superior to that observed with devitalized bone matrix (DVBM) additives.

As indicated by the above described results, collagen dispersions containing calcium hydrogen phosphate dihydrate salts [$CaHPO_4.2H_2O$] stimulated the performance of osteoinductive proteins resulting in bone of increased mass and superior bone maturity. Based on this evidence, the salt and other acidic calcium salts can be used as an alternative for demineralized bone additives. This substitution should provide significant economic savings, eliminate potential allograft disease transfer and provide more reproducible and superior clinical results as a bone void filler or autogeneous graft extender.

TABLE 7

Histological scores and sample requirements.

| Histological Score | Sample criteria |
|---|---|
| 0 | No residual implanted sample found.<br>Section shows no silver stained deposits or those deposits are associated with acellular events.<br>Explants are generally small, soft and avascular. |
| 1 | Focal areas of silver stained mineralized tissues are of cellular origin. This may include mineralized cartilage as well as mineralized osteoid matrix.<br>Silver stained areas are randomly located throughout the explant, and typically encompass less than 50% of the explant.<br>Generally small |
| 2 | Silver stained areas are mineralized cartilage or very early woven bone.<br>Osteoblasts appear in rows of only about 6 to 10 cells.<br>If osteoid is present, it is generally present on less than 10% of the mineralizing tissue in the section.<br>Small areas of hematopoietic marrow elements may be visible (generally sinusoids containing red blood cells). |
| 3 | Sheets of active osteoblasts, (e.g., cells are plump and cuboidal or polygonal) generally consisting of 10 or more cells, appear in less than 50% of the active mineralized portion. They are generally not continuous.<br>Bone associated with osteoblasts is generally woven, containing some osteocytes.<br>Woven bone appears at outer regions of explant and may have breaks of fibrous tissue or mineralized cartilage <10% of surface.<br>Some hematopoietic marrow elements may be visible. (Hemopoietic cords and sinusoids containing red blood cells). |
| 4 | Mineralized tissue at the periphery is generally not woven, but a mature band containing lamellar bone.<br>Mature bone is associated with continuous osteoblast surfaces in at least 50% of bony area.<br>Osteoid contains active osteoblasts and a visible osteoid matrix.<br>Evidence of bone marrow through presence of granulocytes, hemopoietic cords and sinusoids is common.<br>Evidence of osteoclastic re-adsorption. |

TABLE 7-continued

Histological scores and sample requirements.

| Histological Score | Sample criteria |
|---|---|
| 5 | Solid rim of mature bone with few breaks around outer edge.<br>Mature bone contains osteocytes in organized patterns.<br>Mature bone contains wide dark staining (in TBO stain) osteoid.<br>Osteoid seams are continuous; very thick with osteoblasts.<br>Bone marrow contains hemopoietic cords packed with cells, granulocytes, sinusoids and adipocytes.<br>Trabecular bone in marrow is reabsorbing and may appear as focal areas with little branching.<br>Explant center may contain mature woven bone or be infarcted and largely acellular.<br>Strong presence of osteoclasts and/or lacunae. |

TABLE 8

Average (inter-animal) and relative (intra-animal) histological scores for implants supplemented with various calcium phosphates.

Average Histology Score

| | Average Mineral Mass | | | Direct Comparison Averages | | | | |
|---|---|---|---|---|---|---|---|---|
| | [0-5] | ±SD | n | [0-5] | ±SD | [%] | ±SD | n |
| Control | 2.2 | 0.6 | 123 | | | | | |
| DVBM | 2.8 | 0.8 | 156 | 3.0 | 0.3 | +33.3% | 19.8% | 18 |
| $Ca(H_2PO_4)_2$ (MCP) | 2.2 | 0.8 | 48 | 1.9 | 0.6 | +9.9% | 19.8% | 18 |
| $CaHPO4 \cdot 2H_2O$ (DCP) | 2.9 | 0.8 | 111 | 2.5 | 0.7 | +39.1% | 23.2% | 24 |
| $2CaO \cdot P_2O_5 \cdot 2H_2O$ (CP) | 2.3 | 0.6 | 15 | 2.3 | 0.5 | +11.1% | 22.8% | 6 |
| $3CaO \cdot P_2O_5$ (α-TCP) | 1.1 | 0.4 | 21 | 1.3 | 0.5 | −35.1% | 27.4% | 12 |
| $3CaO \cdot P_2O_5$ (β-TCP) | 1.3 | 0.5 | 9 | 1.3 | 0.5 | −23.9% | 22.2% | 6 |
| $3.33CaO \cdot P_2O_5$ (HA-am) | 1.3 | 0.5 | 12 | 1.2 | 0.4 | −46.7% | 27.4% | 6 |
| $3.33CaO \cdot P_2O_5$ (HA-am) | 1.4 | 0.5 | 18 | 1.7 | 0.5 | −20.0% | 27.4% | 6 |
| $3.33CaO \cdot P_2O_5$ (HA-px) | 1.4 | 0.5 | 18 | 2.0 | 0.0 | −26.7% | 18.3% | 6 |
| $4CaO \cdot P_2O_5$ (TTCP) | 1.0 | 0.0 | 12 | 1.0 | 0.0 | −36.1% | 18.7% | 6 |
| $CaCO_3$ (aragonite) | 1.0 | 0.0 | 24 | 1.0 | 0.0 | −63.9% | 6.8% | 6 |
| $CaCO_3$ (calcite) | 1.0 | 0.0 | 24 | 1.0 | 0.0 | −58.3% | 9.1% | 6 |

Example 4

A paste was made comprising (i) about 90 parts by volume dehydrothermally-crosslinked collagen:dical particles (about 66 wt % dical) having particle sizes of 125-300 mm and 96% porosity; (ii) about 10 parts by volume soluble collagen; (iii) monocalcium phosphate; and (iv) about 100 parts by volume water. The monocalcium phosphate was included for pH control and the amount varied, with greater amounts leading to lower paste pH. Generally, the amount of monocalcium phosphate was about 2-10 wt % relative to components (i)-(iii), i.e., not including the weight of water. Generally, sufficient monocalcium phosphate was added to yield pH values of the paste from about 4.5 to 4.9. The dehydrothermal crosslinking was performed at about 110° C. for about 48 hr.

The high porosity of component (i) was chosen to encourage high rate and depth of cellular penetration into the paste. In essence, the particles (i) act as extrinsic bone nucleation sites throughout the entire mass.

The relatively small concentration of soluble collagen (ii) was chosen to allow for the development of a cohesive, taffy-like paste consistency. The cross-linked collagen:dical particles are completely insoluble and lack cohesion in water or marrow. In contrast, the addition of soluble collagen allows the formation of a collagen gel. Collagen forms highly viscous gels near its isoelectric point (pH 4-5.5). Simple, short-term pH control causes the collagen to solubilize and gel, trapping the cross-linked collagen particles in a cohesive, pliable mass.

Monocalcium phosphate (iii) was selected as a salt for temporary acidic pH control in the paste. Its use, in comparison to alternatives, results in dramatically superior improvements in stimulated bone quantity and histological quality. These results were also supported in prior sponge optimization research. The pH effect was temporary primarily as a result of the solubility of monocalcium phosphate in body fluids.

The pastes generated according to this example were tested in the rat model described in Example 3.

Figure 16A:
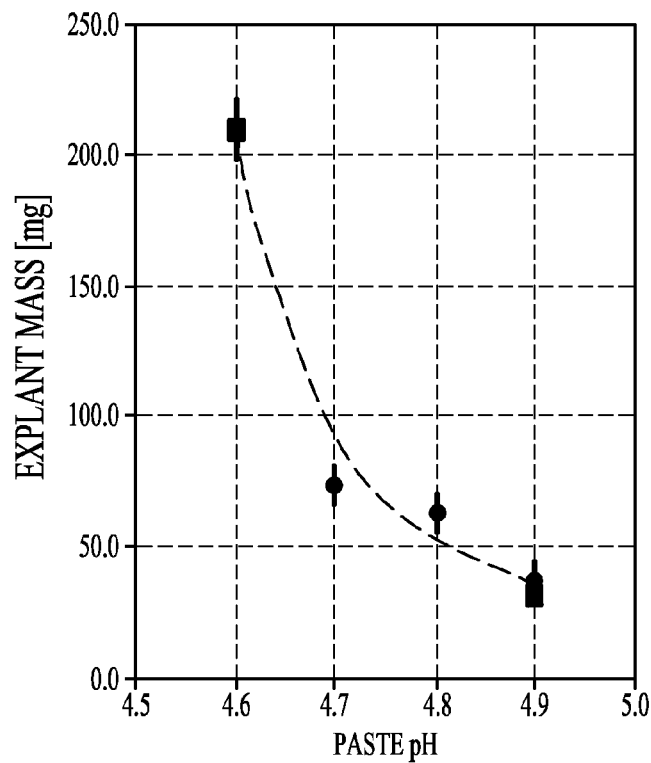
FIG. 16: Influence of temporary pH of the paste of Example 4 on induced explant and mineral mass values.
Figure 16B:
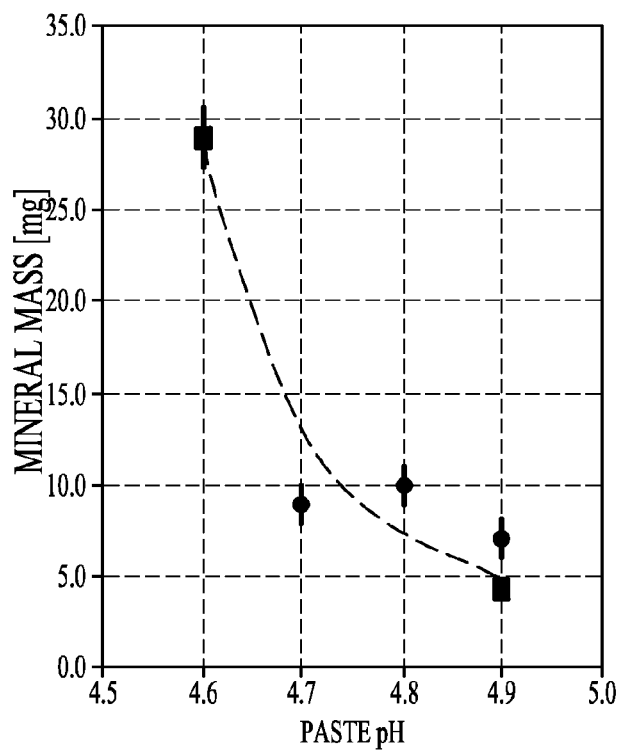
Figure 17:
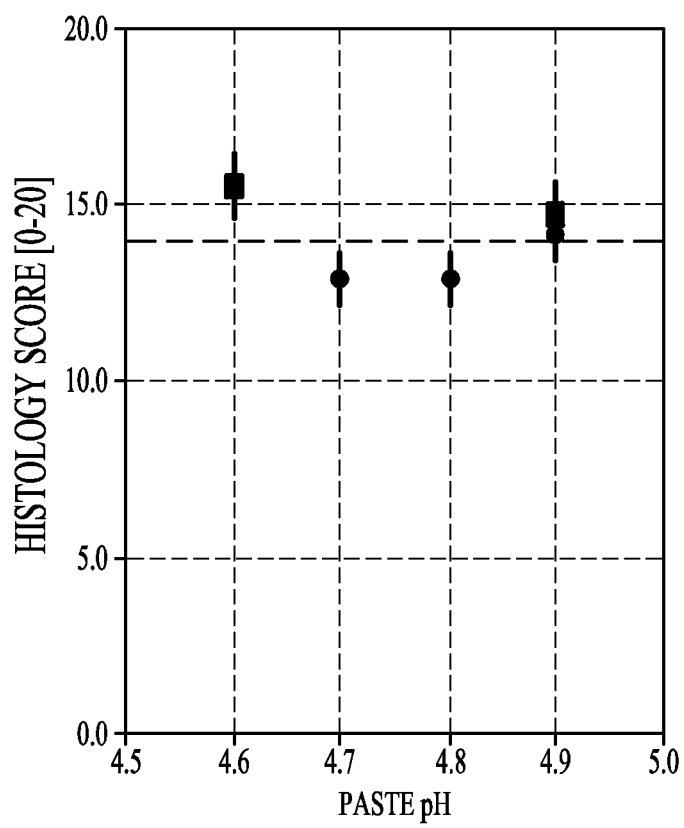
FIG. 17: Influence of temporary pH of the paste of Example 4 on induced bone quality.

The effect of initial pH of the paste on explant mass and mineral mass is shown in FIG. 16. The effect of initial pH of the paste on the histology score is shown in FIG. 17.

The results in FIG. 16 clearly demonstrate that pH has a significant effect on total explant and mineral mass. The results in FIG. 17 also indicate that within the tested range acidic pH values have little influence on histological bone maturity. It should be emphasized when reviewing these results that, in comparison to reference controls with equivalent inductive growth factor doses, the paste formulations yield histologically superior explants with average bone masses around 250 mg, which corresponds to a 400% improvement in bone mass induction.

Figure 5A:
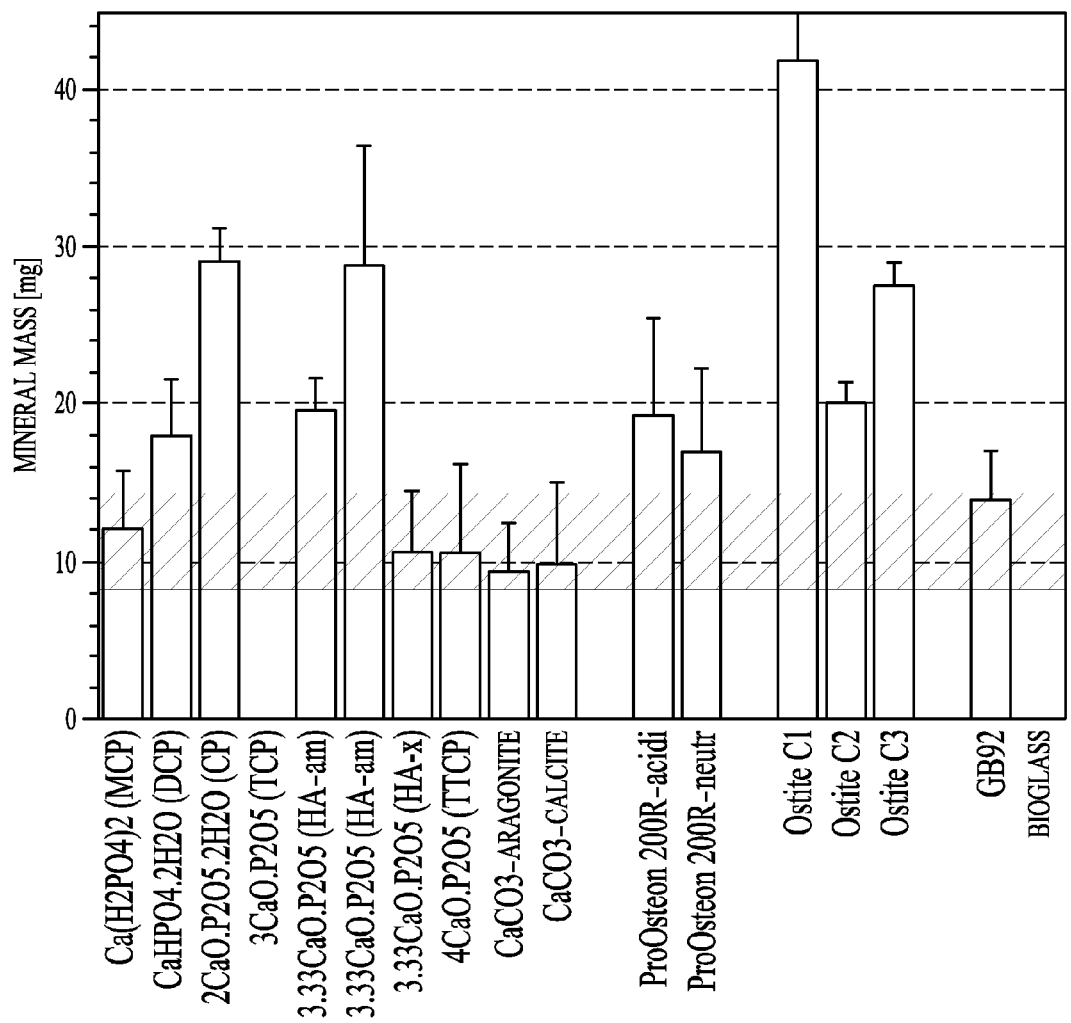
FIG. 5: A. Mineral mass of disks composed of osteoinductive compounds at time of harvest normalized to average value measured against controls containing only collagen and bone proteins.
B. Average and normalized mineral mass at time of harvest.
Figure 6A:
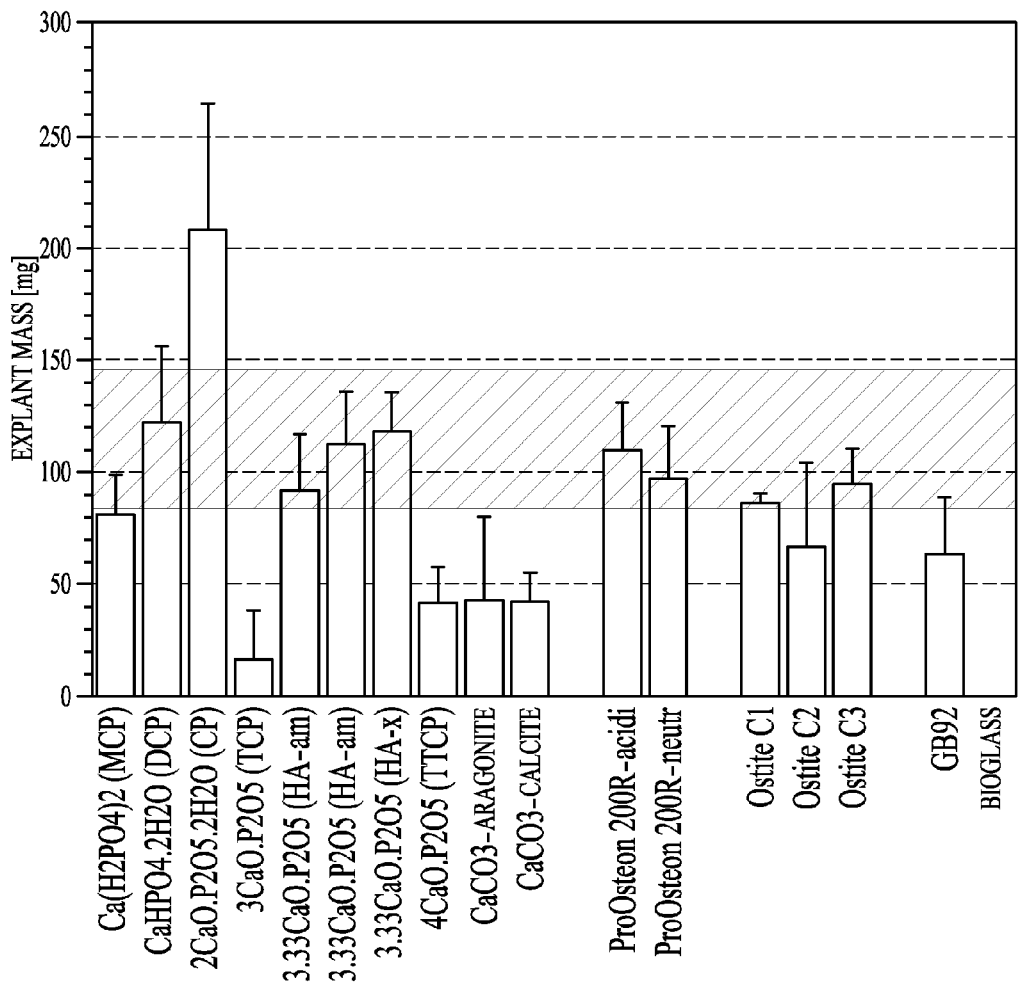
FIG. 6: A. Explant mass of disks composed of osteoinductive compounds at time of harvest normalized to average value measured against controls containing collagen, bone proteins and devitalized bone matrix.
B. Average and normalized values of explant mass at time of harvest.

With respect to FIGS. 2-5, the osteogenic effects of collagen disks containing various calcium phosphate salt compositions and bone growth protein (BMP) were assessed based on explant mass (FIGS. 2A-B), histology score (FIGS. 3A-B), mineral concentration (FIGS. 4A-B) and mineral mass (FIGS. 5A-B). As comparatives, some conventional, commercially available osteoinductive compositions (ProOsteon 200R-acidic, ProOsteon 200R-neutral, Ostite C1-C3, GB9N and Bioglass) were similarly tested. Various osteoinductive compositions (first column in FIGS. 2B-5B) were formed into disks together with collagen and BMP, and tested ("CPB" in FIGS. 2B-5B). A control composition comprising collagen and BMP was also tested with each of the above-described samples, and its performance is reported under the heading "CB" in FIGS. 2B-5B).

Similarly, with respect to FIGS. 6-9, the same CP/collagen/BMP disks were again tested for osteogenic performance ("CPB" in FIGS. 6B-9B) and compared to the performance of control disks containing devitalized bone matrix instead of collagen ("CDB" in FIGS. 6B-9B).

Acidic mineral salts other than calcium phosphate salts can be used to control pH, e.g., sulfate-based buffer, lactic acid, calcium citrate, sodium phosphate, and others (page 13, line 22—page 14, line 9). As shown in FIG. 10, implanting a non-calcium phosphate/collagen/BMP composition of pH ranging from 4.5 to 6.5, supplemented with calcium ion, improved the histology score (~130-135%), compared to the histology score obtained with the unsupplemented composition (100%). On the other hand, a phosphate-supplemented composition of pH ranging from 4.5 to 6.5 did not alter the histology score significantly. Simultaneous supplementation of the composition with both phosphate and calcium ions resulted in significant improvements in bone maturity or histology (FIG. 10) and additional bone mass improvements (FIG. 11).

The in vivo performance of osteogenic proteins is influenced by the presence in the osteogenic composition of essential bone components (collagen, calcium, phosphate) and solution pH. Only acidic calcium phosphate additives, however, produced explants with histological scores equivalent and superior to that observed with the addition of devitalized bone matrix (CDB). Statistically superior improvements in histological score were observed with the monocalcium phosphate-based compositions [$Ca(H_2PO_4)_2$, MCP], calcium hydrogen phosphate dihydrate-based compositions [$CaHPO_4 \cdot 2H_2O$, DCP], and calcium pyrophosphate-based compositions [$2CaO \cdot P_2O_5$, CP]. Statistically significant reductions were observed in histological score for all other salt-based compositions tested. Osteogenic performance is hindered with calcium phosphate salts of high (>2 Ca/P) calcia (CaO) content. The Ca/P ratio in the calcium phosphate salt directly correlated with its pH buffering potential (i.e., pKa), with high ratios being strongly alkaline. Monocalcium phosphate [$Ca(H_2PO_4)_2$] is highly acidic (pH~2). Dicalcium hydrogen phosphate and calcium pyrophosphate are moderately acidic (pH~5.5). The neutral transition point (pH~7) is located with tricalcium phosphate compositions. Hydroxyapatites are moderately alkaline (pH~8). Tetracalcium phosphate and calcium carbonates are highly alkaline (pH~10-11). Osteogenic performance is hindered with neutral and alkaline additives.

In conclusion, regarding the influence of composition pH and soluble ion supplementation on osteogenic bone formation, first, the pH of the composition, and thus temporary local pH control of the initial bone growth environment, could be exploited to significantly increase explant and mineral mass values. Explant mass (FIGS. 2A,B and 6A,B), mineral concentration (FIGS. 4A,B and 8A,B) and mineral mass (FIGS. 5A,B and 9A,B) values were appreciably enhanced with either hydroxyapatite or with CP or DCP-based compositions (i.e., moderately alkaline (pH~8.5) or moderately acidic (pH~4.5-6.5) salt components).

Figure 3A:
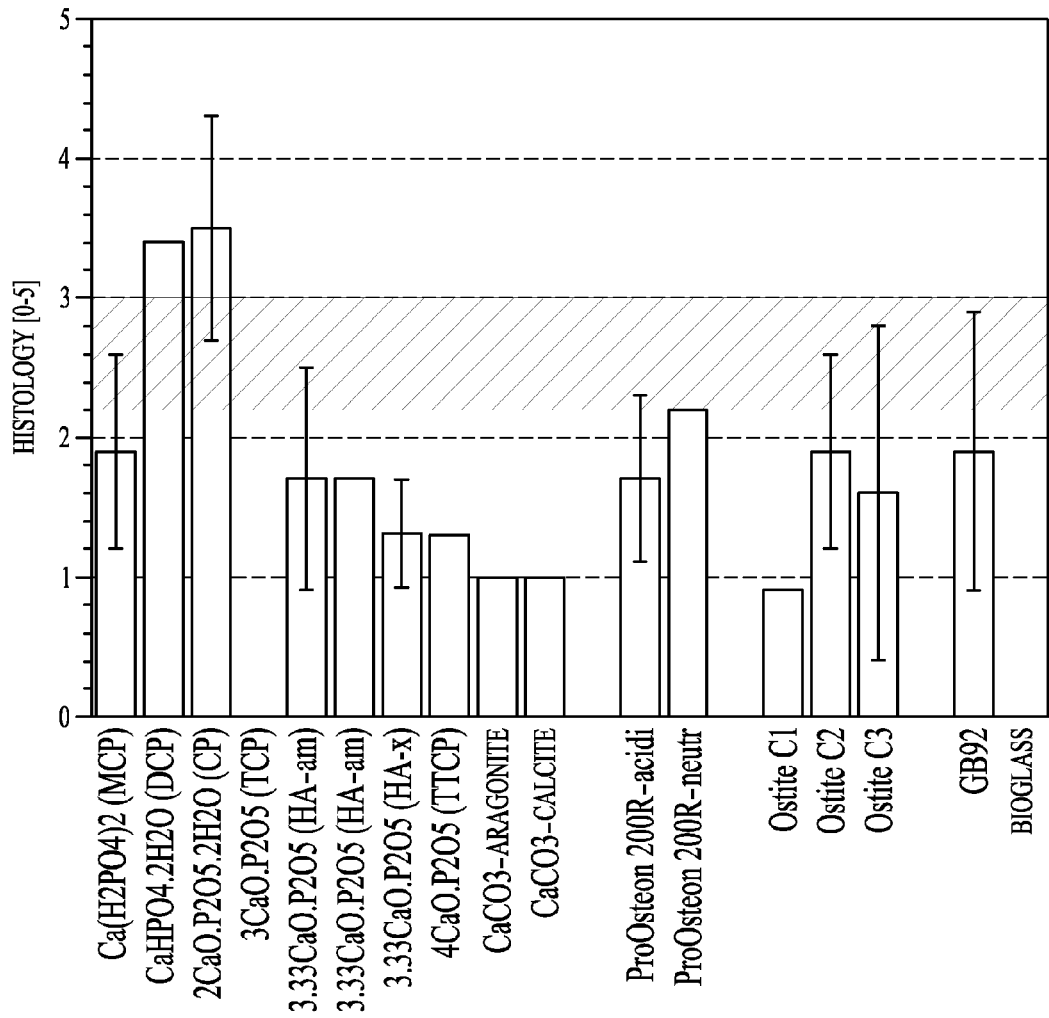
FIG. 3: A. Histology scores of disks composed of osteoinductive compounds at time of harvest normalized to average value measured against controls containing only collagen and bone proteins.
B. Average and normalized histology scores at time of harvest.
Figure 4A:
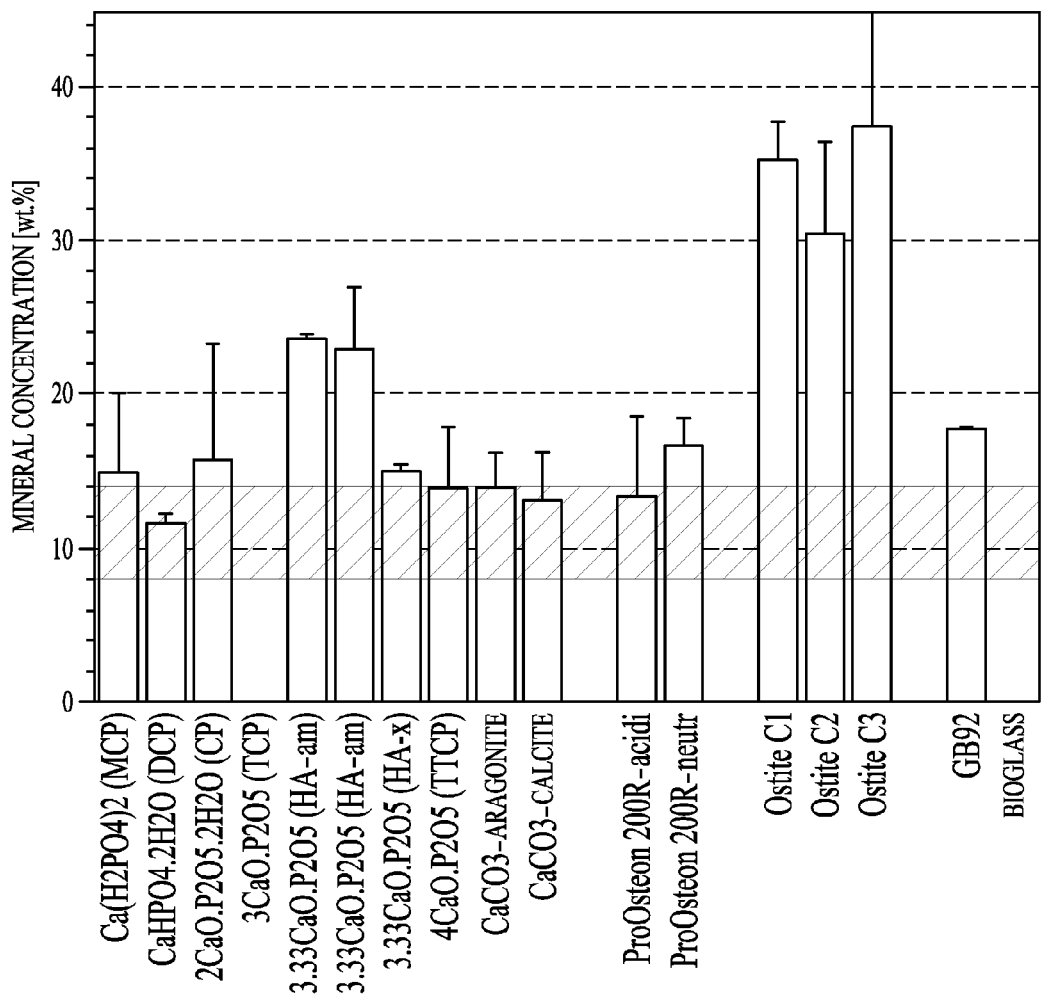
FIG. 4: A. Mineral concentration of disks composed of osteoinductive compounds at time of harvest normalized to average value measured against controls containing only collagen and bone proteins.
B. Average and normalized mineral concentration at time of harvest.
Figure 7A:
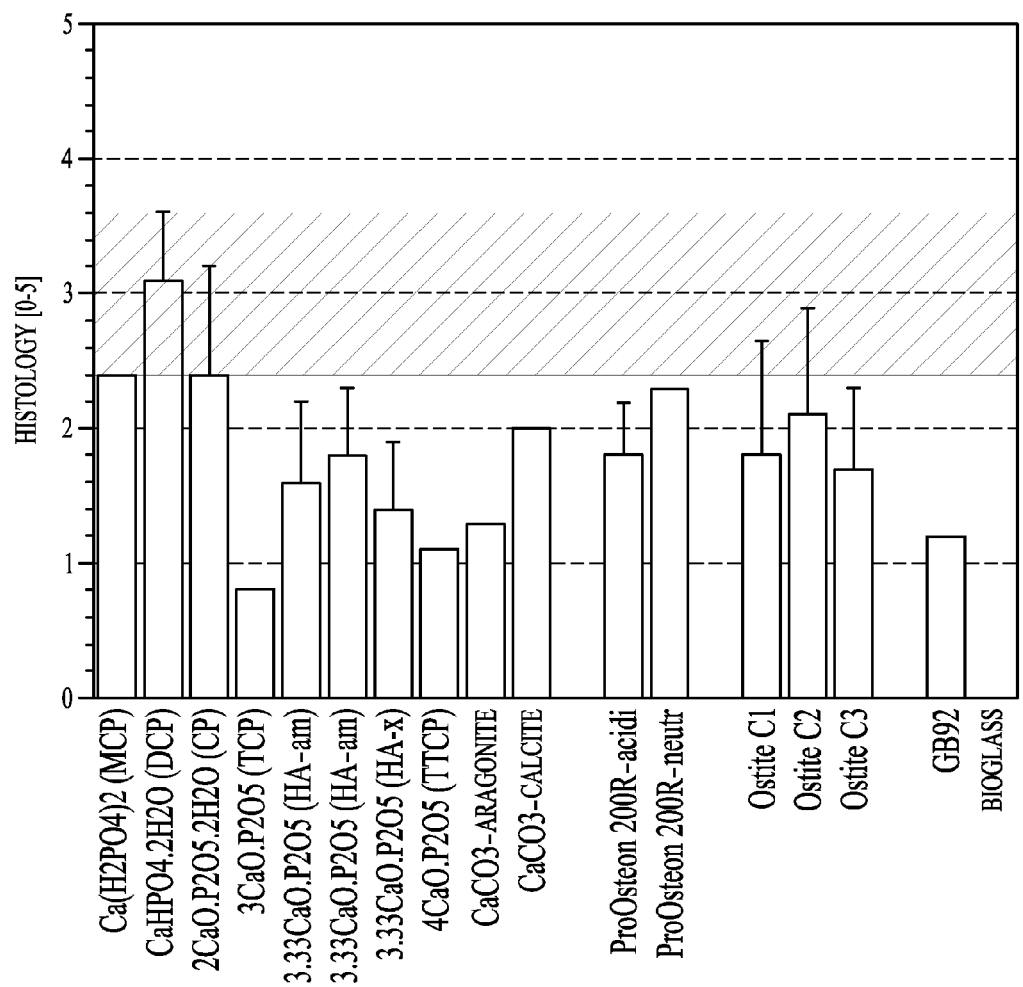
FIG. 7: A. Histology scores of disks composed of osteoinductive compounds at time of harvest normalized to average value measured against controls containing collagen, bone proteins and devitalized bone matrix.
B. Average and normalized histology scores at time of harvest.
Figure 8A:
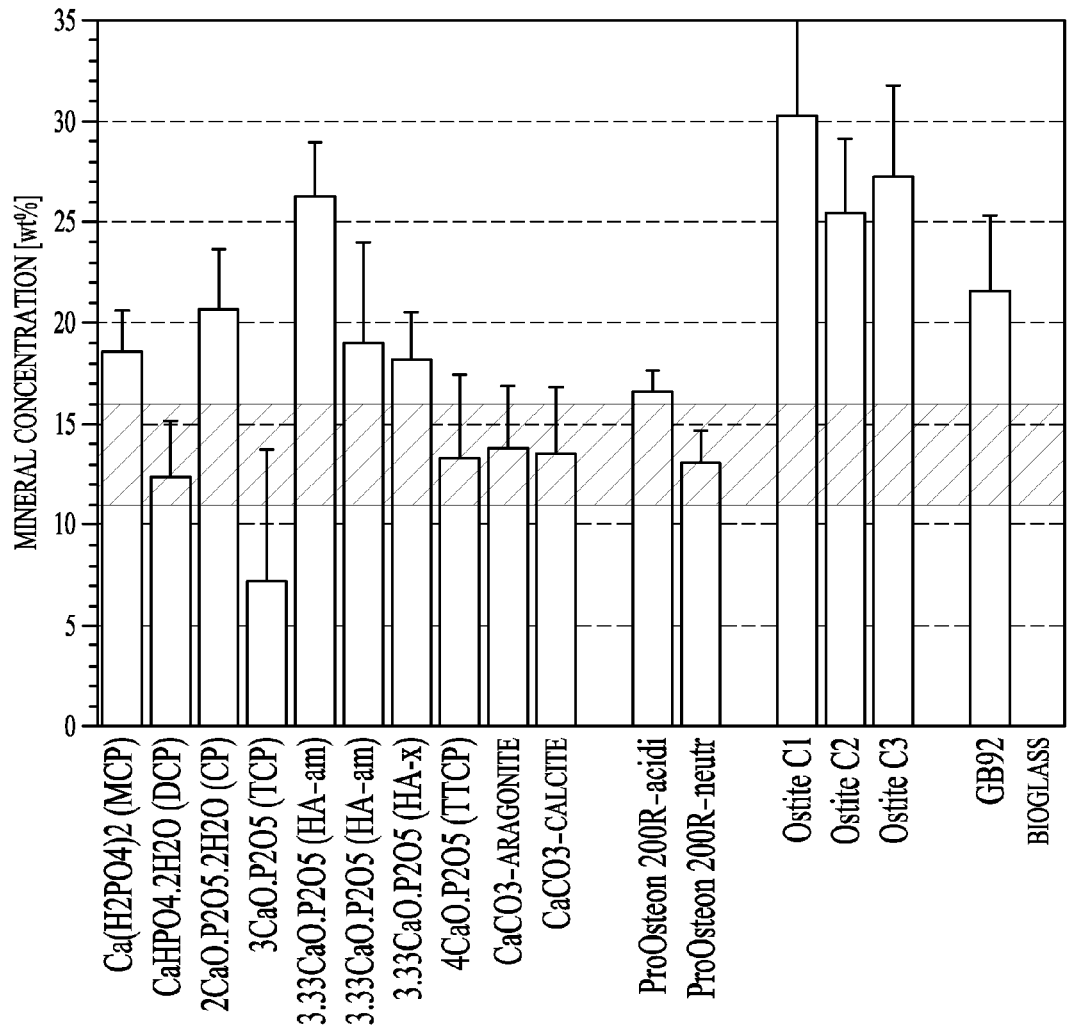
FIG. 8: A. Mineral concentration of disks composed of osteoinductive compounds at time of harvest normalized to average value measured against controls containing collagen, bone proteins and devitalized bone matrix.
B. Average and normalized mineral concentration at time of harvest.
Figure 9A:
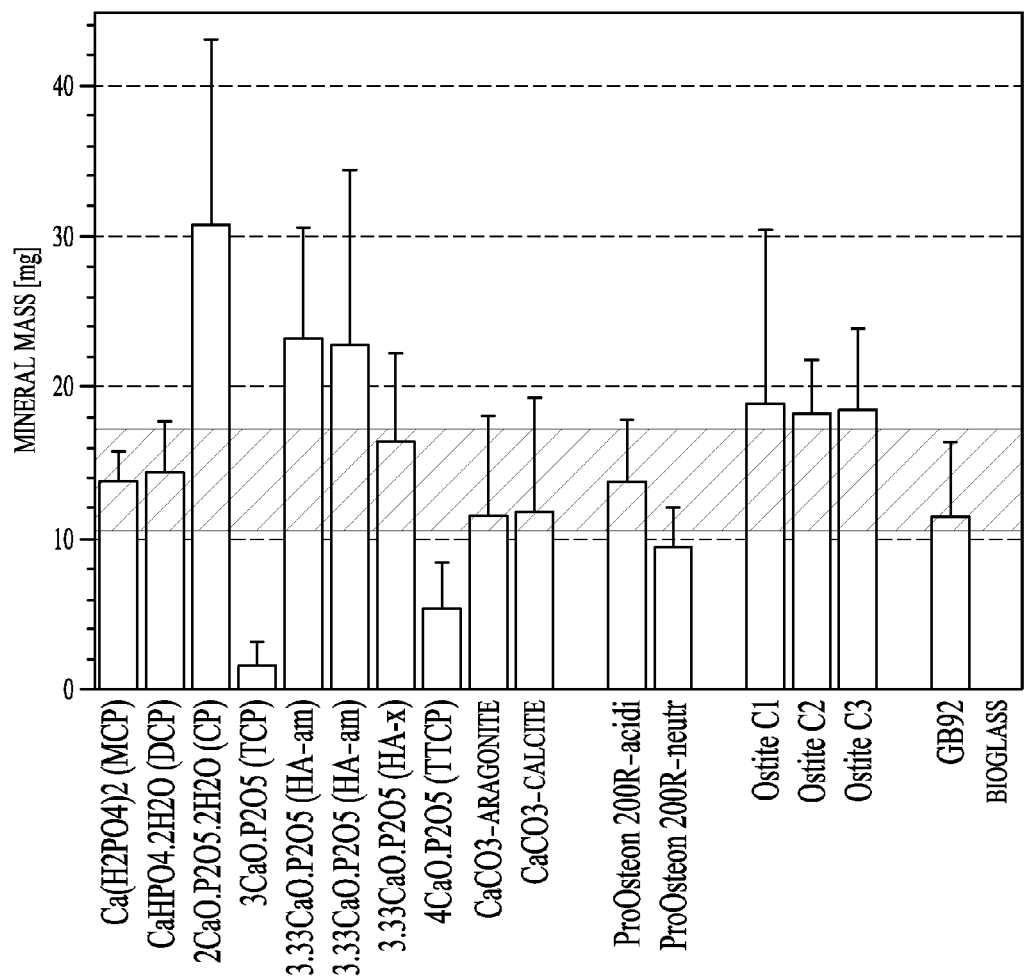
FIG. 9: A. Mineral mass of disks composed of osteoinductive compounds at time of harvest normalized to average value measured against controls containing collagen, bone proteins and devitalized bone matrix.
B. Average and normalized mineral mass at time of harvest.

Second, statistically significant improvements in bone maturity or histology score (FIGS. 3A,B and 7A,B) were realized with the combined use of moderately acidic compositions containing both soluble calcium and phosphate ions and BMP, compared to hydroxyapatite-based compositions with BMP, on either collagen (FIGS. 3A,B) or devitalized bone matrix (FIGS. 7A,B). In contrast, moderately alkaline pH compositions (i.e., the hydroxyapatite-based compositions) hindered bone maturation and significantly reduced cellular activity (FIGS. 3A,B and 7A,B).

Clearly, some of the results are contrary to conventional thinking at the time the subject invention was conceived and reduced to practice. The fact that the majority of the calcium phosphate additives had no effect, or had a negative effect on explant mass contradicts the hypothetical benefits that calcium and phosphate ion supplementation would reasonably have been expected to offer. Based on the available knowledge in this field at the time of the invention, it was originally hypothesized that the clinical performance of osteogenic proteins could be enhanced by supplementing the local availability of essential bone components (collagen, calcium, phosphate). However, if local supplementation were beneficial, one of skill in this field would have expected that improvements in explant mass would have been observed with every calcium phosphate additive that was tested. Furthermore, variations in explant mass improvements would have been expected due to basic solubility, pH and compositional differences [Ca/P ratio]. However, it is shown herein that both acidic composition and $Ca/Pa_4$ ion supplementation can enhance and improve osteoinductive growth factor-induced bone formation independently. It was unexpected that the moderately acidic DCP and CP-based compositions significantly enhanced explant and mineral mass values, compared to the other compositions tested. Our observation that the majority of the calcium phosphate additives had no effect, or had a negative effect on explant mass is contrary to the expected benefits of supplementation with calcium and phosphate ion.

Example 5

A variety of sparingly soluble calcium phosphate salts, [$Ca_x(PO_4)_y$] were used to assess the influence of differences in local, soluble [$Ca^{2+}$] and [$PO_4^{3-}$] ion concentrations and in chemical BMP affinity as demonstrated by bone formation in a small animal model.

Figure 1:
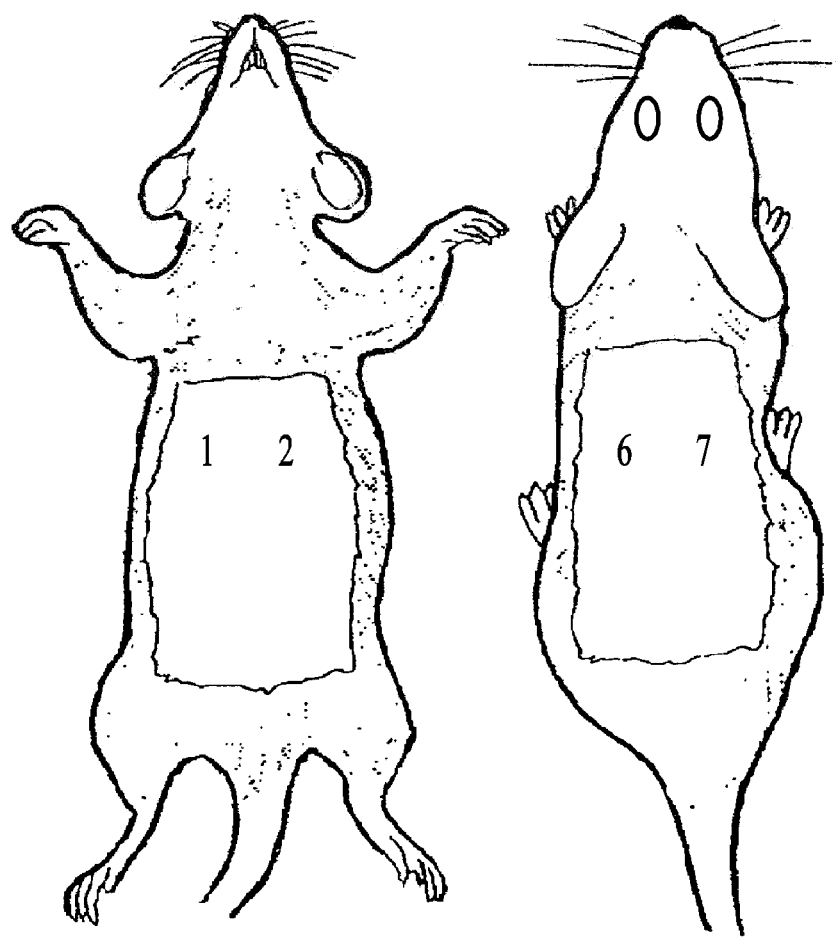
FIG. 1: Indicates location of the subcutaneous implant sites in the upper quadrants of a rat's abdomen and dorsal thorax.
Figure 2A:
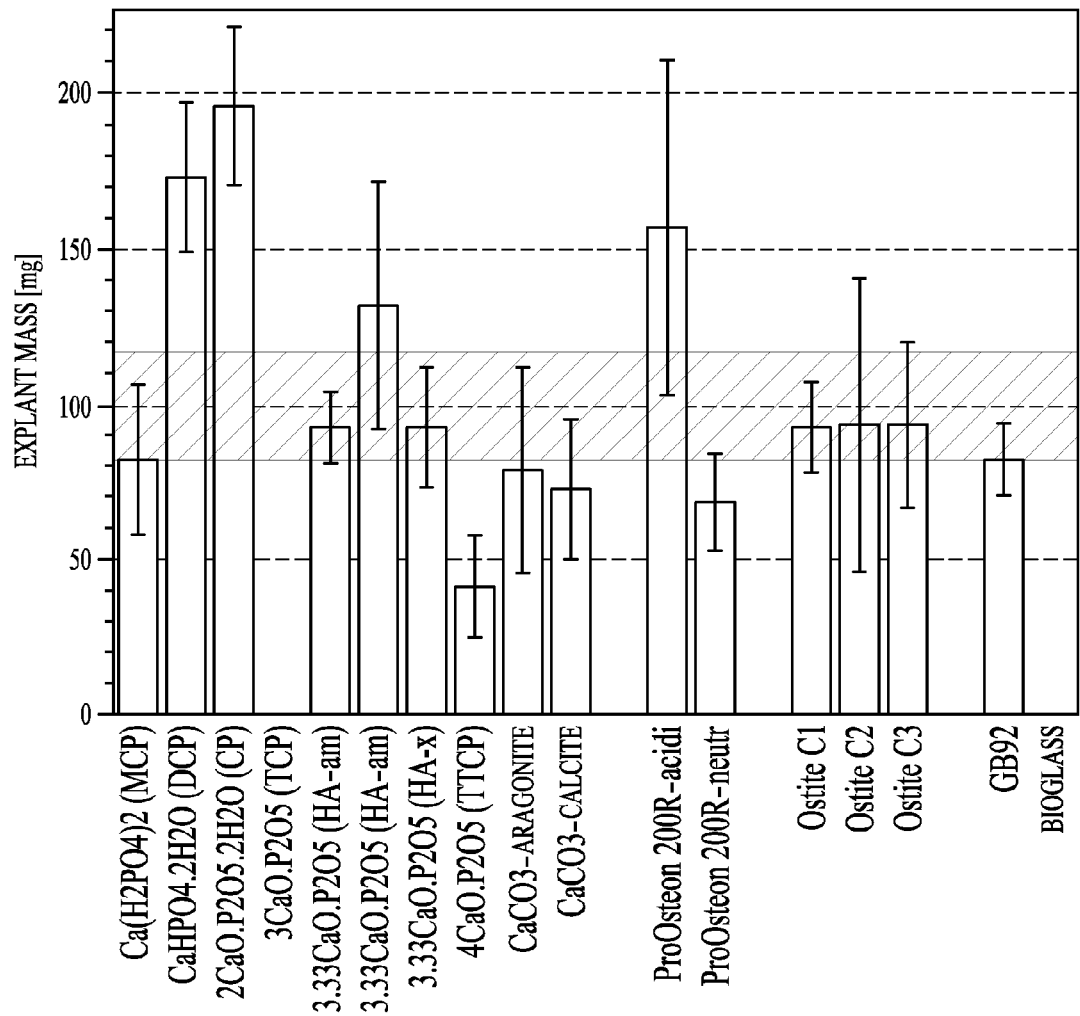
FIG. 2: A. Explant mass of disks composed of osteoinductive compounds at time of harvest, normalized to average value measured against controls containing only collagen and bone proteins.
B. Average and normalized values of explant mass at time of harvest.

The effect of calcium phosphate chemical composition and microstructure (crystal structure) variations on the performance of osteoinductive proteins was evaluated using a subcutaneous rat implant model (FIG. 1). This model has an accelerated rate of bone induction with visible evidence of mineralization appearing in the implant within 1-2 weeks (~10 days), with typical experiments lasting between 14 and 21 days. Osteogenic activity is commonly evaluated using three standard test protocols: histological tissue analysis and mineral composition via x-ray and ash weight analysis.

The testing protocol involved implantation of porous collagen (bovine tendon Type 1, 7 mg, 96 vol. % porosity) samples containing a natural mixture of bovine, osteoinductive proteins (BMPs, 10 µg). A full range of calcium phosphates was evaluated, including: monocalcium phosphate [$Ca(H_2PO_4)_2$], calcium hydrogen phosphate [$CaHPO_4$], calcium pyrophosphate [$2CaO \cdot P_2O_5$], tricalcium phosphate [$\alpha,\beta\text{-}Ca_3(PO_4)_2$], hydroxylapatite [$Ca_5(PO_4)_3(OH)$], tetracalcium phosphate [$Ca_4(PO_4)_2(OH)_2$] or calcium carbonate

[CaCO₃]. The experimental results were used to identify a synthetic additive for collagen to improve its osteoinductive performance.

The effect of variable calcium phosphate compositions on bone quality and maturity is clearly demonstrated in the photomicrograph shown in FIG. 15. The photomicrographs show the bone pattern on the periphery of the explanted material at 2× magnification. Histological sections were selected from samples that matched both the average mass and the average histology score for each test group. The sample and its intra-animal collagen control are presented side-by-side.

In the hematoxylin and eosin stained samples, practically all cytoplasmic structures and intercellular substances are stained various shades of pink. The addition of silver nitrate (Von Kossa technique) stains all mineral black making it simple to detect mineralized tissue. Although this simplifies assessments of mineralization patterns, it does not aid in distinguishing between new bone, mineralized cartilage, residual calcium phosphate additives and calcified carrier. Induced bone is distinguished from other mineralized tissues only by the combined presence of osteoid matrix seams (bright pink) and layered osteoblasts. Mature bone is represented by a continuous and thick cortical rim, lined with a continuous seam of osteoid matrix and active osteoblasts. Marrow quality is also easily assessed with this staining technique since the nuclear structures are stained dark purple or blue. Mature marrow is represented by samples that contain high concentrations of hemopoietic granulocytes (stained dark blue) and fat cells (adipocytes). The location and concentration of fat cells is represented by solubilized white voids.

The toluidine blue tissue stained samples were used to identify cartilage tissue. Cartilage tissue is stained light to deep purple, depending on the local concentration of proteoglycans. Mature cartilage contains a high concentration of proteoglycans. This stain is also useful for visualizing the number and activity of osteoblasts (Ob) and osteocytes (Oc) which are stained dark blue. Bone (B) appears lavender; however residual calcium phosphate salts and other mineralized tissues are equally stained. Marrow elements are difficult to distinguish with this stain.

It is clearly observed that the moderately acidic calcium phosphate salts universally stimulated the amount of bone formation (section diameter) and the depth of bone mineralization (bone staining content). Collagen samples supplemented with calcium hydrogen phosphate dihydrate [CaHPO₄] were the only samples that match the cortical rim bone quality observed in collagen/DVBM controls. The perimeters for samples containing monocalcium phosphate and calcium pyrophosphate were comparatively reduced in maturity. Although improvements in marrow quality were realized with each moderately acidic calcium phosphate additive, the samples supplemented with calcium hydrogen phosphate were the most mature. These samples contained high density concentrations of hemopoeitic granulocytes, red blood cell sinuses, and small adipocyte concentrations characteristic of mature bone.

In contrast, it is observed that the addition of neutral and alkaline calcium phosphate salts significantly inhibits bone formation. The histological quality of the samples supplemented with tricalcium phosphate, hydroxyapatite, tetracalcium phosphate, or calcium carbonate are comparatively reduced. Cellular content and cellular activity correspondingly decreased within samples supplemented with calcium phosphates of increased alkalinity. In the histological sections provided, few areas of active cellular activity are observed. Although the representative sections confirm the experimental observations of increased explant and mineral mass by the differences in sample size and mineral staining, the mineral is of extremely poor quality. The mineral content predominantly includes dystrophically mineralized carrier collagen.

The experimental evidence demonstrates that synthetic bone void fillers supplemented with calcium hydrogen phosphate [CaHPO₄ (DICAL)] enhances both the quantity and histological quality of bone produced. Moderately acidic microenvironments improve protein-stimulated osteoinduction in several different ways. First, an acidic microenvironment can enhance the rates of protein solubilization and protein release from collagen. The resultant increase in local concentration and cellular availability of bone morphogenetic proteins (BMPs) could explain the observed enhancements in bone formation and bone quality. Local pH may also affect protein conformation or cellular activity.

Calcium phosphate compositions with alkaline buffering potentials hinder protein stimulated osteogenic bone formation by two mechanisms. First, bone morphogenetic proteins are insoluble and precipitate in alkaline solutions. The alkaline calcium phosphate additives may precipitate a significant fraction of the inductive proteins and inhibit their osteogenic capabilities. Second and more importantly, alkaline environments initiate the direct precipitation of soluble calcium and phosphate ions. It is likely the alkaline additives cause the serum calcium and phosphate ions to immediately precipitate as apatite onto collagen. If the BMPs simultaneously precipitate within these dystrophic crystals, they would be unavailable to cells until after osteoclastic resorption of the mineralized deposits. The general appearance and lack of cellular activity and the enhanced dystrophic mineral content supports this theory.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A bone graft composition comprising:
   particles of dehydrothermally cross-linked substrate including about 25 wt. % to about 40 wt. % bovine Type I dehydrothermally cross-linked dermal collagen and about 60 wt. % to about 75 wt. % calcium hydrogen phosphate, wherein the particles were prepared from a lyophilized composition of collagen and calcium hydrogen phosphate; and
   a fluid selected from the group consisting of bone marrow aspirate, whole blood or combinations thereof,
   wherein the composition comprises about 2 to about 150 parts by weight of fluid.

2. The bone graft composition of claim 1 wherein the substrate comprises an acidic buffering potential when combined with the fluid.

3. The bone graft composition of claim 2 wherein the acidic buffering potential is between about pH 2 and about pH 5.

4. The bone graft composition of claim 1 wherein the substrate comprises calcium hydrogen phosphate in the form of particles which are about 125 microns to about 5000 microns in average size.

5. The bone graft composition of claim 1 wherein the lyophilized composition comprises a porosity of about 95% to about 98%.

6. The bone graft composition of claim 1 wherein the lyophilized composition is a sponge.

7. The bone graft composition of claim 1 wherein the average particle size is about 125 microns to about 300 microns.

8. The bone graft composition of claim 1 wherein the composition further comprises an acidic calcium phosphate other than calcium hydrogen phosphate.

9. The bone graft composition of claim 8 wherein the acidic calcium phosphate mineral comprises monocalcium phosphate.

10. The bone graft composition of claim 8 wherein the composition comprises about 2 parts by weight to about 15 parts by weight of an acidic calcium phosphate mineral other than calcium hydrogen phosphate.

11. The bone graft composition of claim 1 wherein the composition further comprises a second collagen other than bovine Type I dermal collagen.

12. The bone graft composition of claim 11 wherein the second collagen comprises a soluble collagen.

13. The bone graft composition of claim 11 wherein the composition comprises 1 part by weight to about 20 parts by weight of collagen other than bovine Type I dermal collagen.

14. The bone graft composition of claim 11 wherein the composition comprises about 85 parts by volume to about 95 parts by volume of the substrate and about 5 parts by volume to about 15 parts by volume of the second collagen.

15. The bone graft composition of claim 11 wherein the composition comprises about 3 parts by weight to about 10 parts by weight of the substrate; about 1 part by weight to about 20 parts by weight of collagen other than bovine Type I dermal collagen; and about 2 parts by weight to about 15 parts by weight of an acidic calcium phosphate mineral other than calcium hydrogen phosphate.

16. The bone graft composition of claim 1 wherein the composition is in the form of a putty.

17. The bone graft composition of claim 16, wherein a volume ratio of the fluid to a dry substrate volume is 0.6:1.

18. The bone graft composition of claim 16 wherein a volume ratio of the fluid to a dry substrate volume is 1.3:1.

19. The bone graft composition of claim 1 wherein the composition is in the form of a paste.

20. The bone graft composition of claim 1 wherein the fluid further comprises a fluid selected from the group consisting of platelet-rich-plasma, serum, saline, water, PBS, cell culture media or combinations thereof.

* * * * *